US005648212A

United States Patent [19]
Albertsen et al.

[11] Patent Number: 5,648,212
[45] Date of Patent: Jul. 15, 1997

[54] DETECTION OF INHERITED AND SOMATIC MUTATIONS OF APC GENE IN COLORECTAL CANCER OF HUMANS

[75] Inventors: Hans Albertsen, Salt Lake City, Utah; Rakesh Anand, Cheshire, England; Mary Carlson; Joanna Groden, both of Salt Lake City, Utah; Philip John Hedge, Cheshire, England; Geoff Joslyn, Salt Lake City, Utah; Kenneth Kinzler, Baltimore, Md.; Alexander Markham, Cheshire, England; Yusuke Nakamura, Tokyo, Japan; Andrew Thliveris, Salt Lake City, Utah; Bert Vogelstein, Baltimore, Md.; Raymond L. White, Salt Lake City, Utah

[73] Assignees: The John Hopkins University, Baltimore, Md.; University of Utah, Salt Lake City, Utah; Japanese Foundation for Cancer Research Cancer Institute, Tokyo, Japan; Zeneca Limited, Cheshire, England

[21] Appl. No.: 289,548

[22] Filed: Aug. 12, 1994

Related U.S. Application Data

[62] Division of Ser. No. 741,940, Aug. 8, 1991, Pat. No. 5,352,775.

[30] Foreign Application Priority Data

Jan. 16, 1991 [GB] United Kingdom .................... 9100962
Jan. 16, 1991 [GB] United Kingdom .................... 9100963
Jan. 16, 1991 [GB] United Kingdom .................... 9100974
Jan. 16, 1991 [GB] United Kingdom .................... 9100975

[51] Int. Cl.$^6$ ............... C07H 21/04; C07H 21/02; C12P 19/34; C12Q 1/68
[52] U.S. Cl. .................. 435/6; 435/91.1; 435/91.2; 536/23.5; 536/24.31; 536/24.33; 935/77; 935/78
[58] Field of Search .............. 435/6, 91.1, 91.2; 536/23.5, 24.31, 24.33; 935/77, 78

[56] References Cited

U.S. PATENT DOCUMENTS

5,098,823  3/1992  Bodmer et al. .
5,137,806  8/1992  LeMaistie et al. .

FOREIGN PATENT DOCUMENTS

WO89/01481  8/1988  WIPO .

OTHER PUBLICATIONS

Solomon et al., Nature 328:614–616 Aug. 13, 1987.
Nakamura et al., Am. J. Hum., Genet. 43:638–644 1988.
Vogelstein et al., New England Journal of Medicine 319(9):525–532 Sep. 1, 1988.
Groden, et al., "Identification and Characterization of the Familial Adenomatous Polyposis Coli Gene", *Cell*, 66:589–600 (1991).
Joslyn, et al., "Identification of Delection Mutations and Three New Genes at the Familial Polyposis Locus", *Cell*, 66:601–613 (1991).
Kinzler, et al., "Identification of FAP Locus Genes from Chromsome 5q21", *Science*, 253:661–665 (1991).
Nishisho, et al., "Mutations of Chromosome 5q21 Genes in FAP and Colorectal Cancer Patients", *Science*, 253:665–669 (1991).
Orita, et al., Genomics, vol. 5, pp. 874–879, 1989.
Stanbridge, et al., "Identifying Tumor Suppressor Genes in Human Colorectal Cancer", *Science*, 247:12–13 (1990).

(List continued on next page.)

*Primary Examiner*—Stephanie W. Zitomer
*Assistant Examiner*—Paul B. Tran
*Attorney, Agent, or Firm*—Banner & Witcoff, Ltd.

[57] ABSTRACT

Methods are provided for assessing mutations of the APC gene in human tissues and body samples. APC mutations are found in familial adenomatous polyposis patients as well as in sporadic colorectal cancer patients. APC is expressed in most normal tissues. APC is a tumor suppressor.

36 Claims, 72 Drawing Sheets

OTHER PUBLICATIONS

Fearon et al., "Identification of a Chromosome 18q Gene That is Altered in Colorectal Cancer", *Science*, 247:49–56 (1990).

Baker et al., "Chromosome 17 Deletions and p. 53 Gene Mutations in Colorectal Carcinomas", *Science*, 244:217–221.

Bodmer et al., "Localization of the Gene for Familial Adenomatous Polyposis on Chromosome 5", *Nature*, 328:614–616 (1987).

FIG. 2A

TB1 Amino Acid Sequence

```
VAPVVVGSGR APRHPAPAAM HPRRPDGFDG LGYRGGARDE QGFGGAFPAR SFSTGSDLGH   60
WVTTPPDIPG SRNLHWGEKS PPYGVPTTST PYEGPTEEPF SSGGGGSVQG QSSEQLNRFA  120
GFGIGLASLF TENVLAHPCI VLRRQCQVNY HAQHYHLTPF TVINIMYSFN KTQGPRALWK  180
GMGSTFIVQG VTLGAEGIIS EFTPLPREVL HKWSPKQIGE HLLLKSLTYV VAMPFYSASL  240
IETVQSEIIR DNTGILECVK EGIGRVIGMG VPHSKRLLPL LSLIFPTVLH GVLHYIISSV  300
IQKFVLLILK RKTYNSHLAE STSPVQSMLD AYFPELIANF AASLCSDVIL YPLETVLHRL  360
HIQGIRTIID NTDLGYEVLP INTQYEGMRD CINTIRQEEG VFGFYKGFGA VIIQYTLHAA  420
VLQITKIIYS TLLQ                                                    434
```

FIG. 2B

TB2 Amino Acid Sequence

```
ELRRFDRFLH EKNCMTDLLA KLEAKTGVNR SFIALGVIGL VALYLVFGYG ASLLCNLIGF   60
GYPAYISIKA IESPNKEDDT QWLTYWVYG VFSIAEFFSD IFLSWFPFYY ILKCGFLLWC  120
MAPSPSNGAE LLYKRIIRPF FLKHESQMDS VVKDLKDKAK ETADAITKEA KKATVNLLGE  180
EKKST                                                             185
```

FIG. 3A

```
Met Ala Ala Ser Tyr Asp Gln Leu Leu Lys Gln Val Glu Ala Leu
 1                   5                  10                  15

Lys Met Glu Asn Ser Asn Leu Arg Gln Glu Leu Glu Asp Asn Ser Asn
         20                  25                  30

His Leu Thr Lys Leu Glu Thr Glu Ala Ser Asn Met Lys Glu Val Leu
         35                  40                  45

Lys Gln Leu Gln Gly Ser Ile Glu Asp Glu Ala Met Ala Ser Ser Gly
         50                  55                  60

Gln Ile Asp Leu Leu Glu Arg Leu Lys Glu Leu Asn Leu Asp Ser Ser
 65                  70                  75                  80

Asn Phe Pro Gly Val Lys Leu Arg Ser Lys Met Ser Leu Arg Ser Tyr
         85                  90                  95

Gly Ser Arg Glu Gly Ser Val Ser Ser Arg Ser Gly Glu Cys Ser Pro
         100                 105                 110
```

FIG. 3B

```
Val Pro Met Gly Ser Phe Pro Arg Arg Gly Phe Val Asn Gly Ser Arg
            115                 120                 125

Glu Ser Thr Gly Tyr Leu Glu Leu Glu Lys Glu Arg Ser Leu Leu
            130                 135                 140

Leu Ala Asp Leu Asp Lys Glu Lys Glu Lys Asp Trp Tyr Tyr Ala
            145                 150                 155                 160

Gln Leu Gln Asn Leu Thr Lys Arg Ile Asp Ser Leu Pro Leu Thr Glu
            165                 170                 175

Asn Phe Ser Leu Gln Thr Asp Leu Thr Arg Arg Gln Leu Glu Tyr Glu
            180                 185                 190

Ala Arg Gln Ile Arg Val Ala Met Glu Glu Gln Leu Gly Thr Cys Gln
            195                 200                 205

Asp Met Glu Lys Arg Ala Gln Arg Arg Ile Ala Arg Ile Gln Gln Ile
            210                 215                 220
```

FIG. 3C

```
Glu Lys Asp Ile Leu Arg Ile Arg Gln Leu Leu Gln Ser Gln Ala Thr
225                 230              235             240

Glu Ala Glu Arg Ser Ser Gln Asn Lys His Glu Thr Gly Ser His Asp
                245             250             255

Ala Glu Arg Gln Asn Gly Gln Gly Val Gly Glu Ile Asn Met Ala
                260             265             270

Thr Ser Gly Asn Gly Gln Gly Ser Thr Thr Arg Met Asp His Glu Thr
                275             280             285

Ala Ser Val Leu Ser Ser Ser Ser Thr His Ser Ala Pro Arg Arg Leu
                290             295             300

Thr Ser His Leu Gly Thr Lys Val Glu Met Val Tyr Ser Leu Leu Ser
                305             310             315             320

Met Leu Gly Thr His Asp Lys Asp Lys Asp Asp Met Ser Arg Thr Leu Leu Ala
                325             330             335
```

FIG. 3D

Met Ser Ser Gln Asp Ser Cys Ile Ser Met Arg Gln Ser Gly Cys
340                         345                         350

Leu Pro Leu Ile Gln Leu Leu His Gly Asn Asp Lys Asp Ser Val
        355                         360                         365

Leu Leu Gly Asn Ser Arg Gly Ser Lys Glu Ala Arg Ala Arg Ala Ser
            370                         375                         380

Ala Ala Leu His Asn Ile Ile His Ser Gln Pro Asp Asp Lys Arg Gly
385                         390                         395                         400

Arg Arg Glu Ile Arg Val Leu His Leu Leu Glu Gln Ile Arg Ala Tyr
                    405                         410                         415

Cys Glu Thr Cys Trp Gln Glu Ala His Glu Pro Gly Met Asp
            420                         425                         430

Gln Asp Lys Asn Pro Met Pro Ala Pro Val Glu His Gln Ile Cys Pro
435                         440                         445

FIG. 3E

Ala Val Cys Val Leu Met Lys Leu Ser Phe Asp Glu His Arg His
450                     455                     460

Ala Met Asn Glu Leu Gly Gly Leu Gln Ala Ile Ala Glu Leu Gln
465                     470                     475                     480

Val Asp Cys Glu Met Tyr Gly Leu Thr Asn Asp His Tyr Ser Ile Thr
                        485                     490                     495

Leu Arg Arg Tyr Ala Gly Met Ala Leu Thr Asn Leu Thr Phe Gly Asp
                500                     505                     510

Val Ala Asn Lys Ala Thr Leu Cys Ser Met Lys Gly Cys Met Arg Ala
                515                     520                     525

Leu Val Ala Gln Leu Lys Ser Lys Ser Glu Asp Leu Gln Gln Val Ile
530                     535                     540

Ala Ser Val Leu Arg Asn Leu Ser Trp Arg Ala Asp Val Asn Ser Lys
545                     550                     555                     560

FIG. 3F

Lys Thr Leu Arg Glu Val Gly Ser Val Lys Ala Leu Met Glu Cys Ala
565 570 575

Leu Glu Val Lys Lys Glu Ser Thr Leu Lys Ser Val Leu Ser Ala Leu
580 585 590

Trp Asn Leu Ser Ala His Cys Thr Glu Asn Lys Ala Asp Ile Cys Ala
595 600 605

Val Asp Gly Ala Leu Ala Phe Leu Val Gly Thr Leu Thr Tyr Arg Ser
610 615 620

Gln Thr Asn Thr Leu Ala Ile Ile Glu Ser Gly Gly Gly Ile Leu Arg
625 630 635 640

Asn Val Ser Ser Leu Ile Ala Thr Asn Glu Asp His Arg Gln Ile Leu
645 650 655

Arg Glu Asn Asn Cys Leu Gln Thr Leu Leu Gln His Leu Lys Ser His
660 665 670

FIG. 3G

Ser Leu Thr Ile Val Ser Asn Ala Cys Gly Thr Leu Trp Asn Leu Ser
675                         680                         685

Ala Arg Asn Pro Lys Asp Gln Glu Ala Leu Trp Asp Met Gly Ala Val
        690                         695                         700

Ser Met Leu Lys Asn Leu Ile His Ser Lys Met Ile Ala Met
705                         710                         715                     720

Gly Ser Ala Ala Leu Arg Asn Leu Met Ala Asn Arg Pro Ala Lys
            725                         730                         735

Tyr Lys Asp Ala Asn Ile Met Ser Pro Gly Ser Ser Leu Pro Ser Leu
        740                         745                         750

His Val Arg Lys Gln Lys Ala Leu Glu Ala Leu Asp Ala Gln His
755                         760                         765

Leu Ser Glu Thr Phe Asp Asn Ile Asp Asn Leu Ser Pro Lys Ala Ser
        770                         775                         780

FIG. 3H

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
    805                 810                 815

Gly Asn Met Thr Val Leu Ser Pro Tyr Leu Asn Thr Thr Val Leu Pro
            820                 825                 830

Ser Ser Ser Ser Arg Gly Ser Leu Asp Ser Ser Arg Ser Arg Ser Glu Lys
835                 840                 845

Asp Arg Ser Leu Glu Arg Glu Arg Gly Ile Gly Leu Gly Leu Gly Asn Tyr His
        850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
            885                 890                 895

FIG. 3I

Ile His Thr Ser Gln Glu Asp Arg Ser Ser Gly Ser Thr Thr Glu Leu
                900                 905                 910

His Cys Val Thr Asp Glu Arg Asn Ala Leu Arg Arg Ser Ser Ala Ala
            915                 920                 925

His Thr His Ser Asn Thr Tyr Asn Phe Thr Lys Ser Glu Asn Ser Asn
            930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Asn Asp Gly Tyr Gly Lys Arg
            965                 970                 975

Gly Gln Met Lys Pro Ser Ile Glu Ser Tyr Ser Glu Asp Asp Glu Ser
            980                 985                 990

Lys Phe Cys Ser Tyr Gly Gln Tyr Pro Ala Asp Leu Ala His Lys Ile
995                 1000                1005

FIG. 3J

His Ser Ala Asn His Met Asp Asp Asn Asp Gly Glu Leu Asp Thr Pro
1010                         1015                1020

Ile Asn Tyr Ser Leu Lys Tyr Ser Asp Glu Gln Leu Asn Ser Gly Arg
1025                         1030                1035                1040

Gln Ser Pro Ser Gln Asn Glu Arg Trp Ala Arg Pro Lys His Ile Ile
1045                         1050                1055

Glu Asp Glu Ile Lys Gln Ser Glu Gln Arg Gln Ser Arg Asn Gln Ser
1060                         1065                1070

Thr Thr Tyr Pro Val Tyr Thr Glu Ser Thr Asp Asp Lys His Leu Lys
1075                         1080                1085

Phe Gln Pro His Phe Gly Gln Gln Glu Cys Val Ser Pro Tyr Arg Ser
1090                         1095                1100

Arg Gly Ala Asn Gly Ser Glu Thr Asn Arg Val Gly Ser Asn His Gly
1105                         1110                1115                1120

FIG. 3K

Ile Asn Gln Asn Val Ser Gln Ser Leu Cys Gln Ser Glu Asp Asp Tyr Glu
1125                                        1130                1135

Asp Asp Lys Pro Thr Asn Tyr Ser Glu Arg Tyr Ser Glu Glu Gln
1140                            1145                1150

His Glu Glu Arg Pro Thr Asn Tyr Ser Ile Lys Tyr Asn Glu
1155                            1160                1165

Glu Lys Arg His Val Asp Gln Pro Ile Asp Tyr Ser Leu Lys Tyr Ala
1170                            1175                1180

Thr Asp Ile Pro Ser Ser Gln Lys Gln Ser Phe Ser Lys Ser
1185                            1190                1195                1200

Ser Ser Gly Gln Ser Ser Lys Thr Glu His Met Ser Ser Ser Glu
1205                            1210                1215

Asn Thr Ser Thr Pro Ser Ser Asn Ala Lys Arg Gln Asn Gln Leu His
1220                            1225                1230

FIG. 3L

Pro Ser Ser Ala Gln Ser Arg Ser Gly Gln Pro Gln Lys Ala Ala Thr
1235                         1240                        1245

Cys Lys Val Ser Ser Ile Asn Gln Glu Thr Ile Gln Thr Tyr Cys Val
        1250                        1255                        1260

Glu Asp Thr Pro Ile Cys Phe Ser Arg Cys Ser Ser Leu Ser Ser Leu
1265                        1270                        1275                1280

Ser Ser Ala Glu Asp Glu Ile Gly Cys Asn Gln Thr Thr Gln Glu Ala
                1285                        1290                        1295

Asp Ser Ala Asn Thr Leu Gln Ile Ala Glu Ile Lys Gly Lys Ile Gly
            1300                        1305                        1310

Thr Arg Ser Ala Glu Asp Pro Val Ser Glu Val Pro Ala Val Ser Gln
1315                        1320                        1325

His Pro Arg Thr Lys Ser Ser Arg Leu Gln Gly Ser Ser Leu Ser Ser
        1330                        1335                        1340

FIG. 3M

```
Glu Ser Ala Arg His Lys Ala Val Glu Phe Pro Ser Gly Ala Lys Ser
1345                          1350                         1355                        1360
Pro Ser Lys Ser Gly Ala Gln Thr Pro Lys Ser Pro Pro Glu His Tyr
                1365                         1370                        1375
Val Gln Glu Thr Pro Leu Met Phe Ser Arg Cys Thr Ser Val Ser Ser
                               1380                         1385                 1390
Leu Asp Ser Phe Glu Ser Arg Ser Ile Ala Ser Ser Val Gln Ser Glu
                1395                         1400                        1405
Pro Cys Ser Gly Met Val Ser Gly Ile Ile Ser Pro Ser Asp Leu Pro
1410                          1415                        1420
Asp Ser Pro Gly Gln Thr Met Pro Pro Ser Arg Ser Lys Thr Pro Pro
1425                          1430                        1435                         1440
Pro Pro Pro Gln Thr Ala Gln Thr Lys Arg Glu Val Pro Lys Asn Lys
                1445                        1450                         1455
```

FIG. 3N

Ala Pro Thr Ala Glu Lys Arg Glu Ser Gly Pro Lys Gln Ala Ala Val
1460                        1465                        1470

Asn Ala Ala Val Gln Arg Val Gln Val Leu Pro Asp Ala Asp Thr Leu
1475                        1480                        1485

Leu His Phe Ala Thr Glu Ser Thr Pro Asp Gly Phe Ser Cys Ser Ser
1490                        1495                        1500

Ser Leu Ser Ala Leu Ser Leu Asp Glu Pro Phe Ile Gln Lys Asp Val
1505                        1510                        1515                        1520

Glu Leu Arg Ile Met Pro Pro Val Gln Glu Asn Asp Asn Gly Asn Glu
1525                        1530                        1535

Thr Glu Ser Glu Gln Pro Lys Glu Ser Asn Glu Asn Gln Glu Lys Glu
1540                        1545                        1550

Ala Glu Lys Thr Ile Asp Ser Glu Lys Asp Leu Leu Asp Asp Ser Asp
1555                        1560                        1565

FIG. 30

Asp Asp Ile Glu Ile Leu Glu Glu Cys Ile Ile Ser Ala Met Pro
1570                    1575                    1580

Thr Lys Ser Ser Arg Lys Gly Lys Lys Pro Ala Gln Thr Ala Ser Lys
1585                    1590                    1595                    1600

Leu Pro Pro Val Ala Arg Lys Pro Ser Gln Leu Pro Val Tyr Lys
1605                    1610                    1615

Leu Leu Pro Ser Gln Asn Arg Leu Gln Pro Gln Lys His Val Ser Phe
1620                    1625                    1630

Thr Pro Gly Asp Asp Met Pro Arg Val Tyr Cys Val Glu Gly Thr Pro
1635                    1640                    1645

Ile Asn Phe Ser Thr Ala Thr Ser Leu Ser Asp Leu Thr Ile Glu Ser
1650                    1655                    1660

Pro Pro Asn Glu Leu Ala Ala Gly Glu Gly Val Arg Gly Gly Ala Gln
1665                    1670                    1675                    1680

FIG. 3P

Ser Gly Glu Phe Glu Lys Arg Asp Thr Ile Pro Thr Glu Gly Arg Ser
                1685                1690                1695

Thr Asp Glu Ala Gln Gly Gly Lys Thr Ser Ser Val Thr Ile Pro Glu
                1700                1705                1710

Leu Asp Asp Asn Lys Ala Glu Glu Gly Asp Ile Leu Ala Glu Cys Ile
                1715                1720                1725

Asn Ser Ala Met Pro Lys Gly Lys Ser His Lys Pro Phe Arg Val Lys
                1730                1735                1740

Lys Ile Met Asp Gln Val Gln Gln Ala Ser Ala Ser Ser Ser Ala Pro
                1745                1750                1755                1760

Asn Lys Asn Gln Leu Asp Gly Lys Lys Lys Pro Thr Ser Pro Val
                1765                1770                1775

Lys Pro Ile Pro Gln Asn Thr Glu Tyr Arg Thr Arg Val Arg Lys Asn
                1780                1785                1790

FIG. 3Q

```
Ala Asp Ser Lys Asn Asn Leu Asn Ala Glu Arg Val Phe Ser Asp Asn
1795                1800                1805
Lys Asp Ser Lys Lys Gln Asn Leu Lys Asn Asn Ser Lys Asp Phe Asn
     1810                1815                1820
Asp Lys Leu Pro Asn Asn Glu Asp Arg Val Arg Gly Ser Phe Ala Phe
          1825                1830                1835     1840
Asp Ser Pro His His Tyr Thr Pro Ile Glu Gly Thr Pro Tyr Cys Phe
               1845                1850                1855
Ser Arg Asn Asp Ser Leu Ser Ser Leu Asp Phe Asp Asp Asp Asp Val
                    1860                1865                1870
Asp Leu Ser Arg Glu Lys Ala Glu Leu Arg Lys Ala Lys Glu Asn Lys
     1875                1880                1885
Glu Ser Glu Ala Lys Val Thr Ser His Thr Glu Leu Thr Ser Asn Gln
          1890                1895                1900
```

FIG. 3R

Gln Ser Ala Asn Lys Thr Gln Ala Ile Ala Lys Gln Pro Ile Asn Arg
1905                          1910                         1915                         1920

Gly Gln Pro Lys Pro Ile Leu Gln Lys Gln Ser Thr Phe Pro Gln Ser
         1925                         1930                         1935

Ser Lys Asp Ile Pro Asp Arg Gly Ala Ala Thr Asp Glu Lys Leu Gln
         1940                         1945                         1950

Asn Phe Ala Ile Glu Asn Thr Pro Val Cys Phe Ser His Asn Ser Ser
         1955                         1960                         1965

Leu Ser Ser Leu Ser Asp Ile Asp Gln Glu Asn Asn Lys Glu Asn
         1970                         1975                         1980

Glu Pro Ile Lys Glu Thr Glu Pro Pro Asp Ser Gln Gly Glu Pro Ser
         1985                         1990                         1995                         2000

Lys Pro Gln Ala Ser Gly Tyr Ala Pro Lys Ser Phe His Val Glu Asp
         2005                         2010                         2015

FIG. 3S

Thr Pro Val Cys Phe Ser Arg Asn Ser Ser Leu Ser Ile
2020                    2025                    2030

Asp Ser Glu Asp Asp Leu Leu Gln Glu Cys Ile Ser Ala Met Pro
2035                    2040                    2045

Lys Lys Lys Pro Ser Arg Leu Lys Gly Asp Asn Glu Lys His Ser
2050                    2055                    2060

Pro Arg Asn Met Gly Gly Ile Leu Gly Glu Asp Leu Thr Leu Asp Leu
2065                    2070                    2075                    2080

Lys Asp Ile Gln Arg Pro Asp Ser Glu His Gly Leu Ser Pro Asp Ser
2085                    2090                    2095

Glu Asn Phe Asp Trp Lys Ala Ile Gln Glu Gly Ala Asn Ser Ile Val
2100                    2105                    2110

Ser Ser Leu His Gln Ala Ala Ala Ala Ala Cys Leu Ser Arg Gln Ala
2115                    2120                    2125

FIG. 3T

Ser Ser Asp Ser Asp Ser Ile Leu Ser Leu Lys Ser Gly Ile Ser Leu
2130                     2135                    2140

Gly Ser Pro Phe His Leu Thr Pro Asp Gln Glu Glu Lys Pro Phe Thr
2145                    2150                    2155                    2160

Ser Asn Lys Gly Pro Arg Ile Leu Lys Pro Gly Glu Lys Ser Thr Leu
                    2165                    2170                    2175

Glu Thr Lys Lys Ile Glu Ser Glu Ser Lys Gly Ile Lys Gly Gly Lys
        2180                    2185                    2190

Lys Val Tyr Lys Ser Leu Ile Thr Gly Lys Val Arg Ser Asn Ser Glu
            2195                    2200                    2205

Ile Ser Gly Gln Met Lys Gln Pro Leu Gln Ala Asn Met Pro Ser Ile
    2210                    2215                    2220

Ser Arg Gly Arg Thr Met Ile His Ile Pro Gly Val Arg Asn Ser Ser
2225                    2230                    2235                    2240

FIG. 3U

Ser Ser Thr Ser Pro Val Ser Lys Lys Gly Pro Pro Leu Lys Thr Pro
                    2245                2250                2255

Ala Ser Lys Ser Pro Ser Glu Gly Gln Thr Ala Thr Thr Ser Pro Arg
                2260                2265                2270

Gly Ala Lys Pro Ser Val Lys Ser Glu Leu Ser Pro Val Ala Arg Gln
                2275                2280                2285

Thr Ser Gln Ile Gly Gly Ser Ser Lys Ala Pro Ser Arg Ser Gly Ser
                2290                2295                2300

Arg Asp Ser Thr Pro Ser Arg Pro Ala Gln Gln Pro Leu Ser Arg Pro
                2305                2310                2315                2320

Ile Gln Ser Pro Gly Arg Asn Ser Ile Ser Pro Gly Arg Asn Gly Ile
                2325                2330                2335

Ser Pro Pro Asn Lys Leu Ser Gln Leu Pro Arg Thr Ser Ser Pro Ser
                2340                2345                2350

FIG. 3V

Thr Ala Ser Thr Lys Ser Ser Ser Gly Ser Gly Lys Met Ser Tyr Thr Ser
                2355                    2360                    2365

Pro Gly Arg Gln Met Ser Gln Gln Asn Leu Thr Lys Gln Thr Gly Leu
        2370                    2375                    2380

Ser Lys Asn Ala Ser Ser Ile Pro Arg Ser Glu Ser Ala Ser Lys Gly
        2385                    2390                    2395                2400

Leu Asn Gln Met Asn Asn Gly Ala Asn Lys Lys Val Glu Leu
                2405                    2410                    2415

Ser Arg Met Ser Ser Thr Lys Ser Ser Gly Ser Glu Ser Asp Arg Ser
                2420                    2425                    2430

Glu Arg Pro Val Leu Val Arg Gln Ser Thr Phe Ile Lys Glu Ala Pro
                2435                    2440                    2445

Ser Pro Thr Leu Arg Arg Lys Leu Glu Glu Ser Ala Ser Phe Glu Ser
        2450                    2455                    2460

FIG. 3W

Leu Ser Pro Ser Ser Arg Pro Ala Ser Pro Thr Arg Ser Gln Ala Gln
2465                          2470                          2475                          2480

Thr Pro Val Leu Ser Pro Ser Leu Pro Asp Met Ser Leu Ser Thr His
            2485                          2490                          2495

Ser Ser Val Gln Ala Gly Gly Trp Arg Lys Leu Pro Pro Asn Leu Ser
            2500                          2505                          2510

Pro Thr Ile Glu Tyr Asn Asp Gly Arg Pro Ala Lys Arg His Asp Ile
            2515                          2520                          2525

Ala Arg Ser His Ser Glu Ser Pro Ser Arg Leu Pro Ile Asn Arg Ser
            2530                          2535                          2540

Gly Thr Trp Lys Arg Glu His Ser Lys His Ser Ser Ser Leu Pro Arg
            2545                          2550                          2555                          2560

Val Ser Thr Trp Arg Arg Thr Gly Ser Ser Ser Ser Ile Leu Ser Ala
            2565                          2570                          2575

FIG. 3X

Ser Ser Glu Ser Ser Glu Lys Ala Lys Ser Glu Asp Glu Lys His Val
                2580                    2585                    2590

Asn Ser Ile Ser Gly Thr Lys Gln Ser Lys Glu Asn Gln Val Ser Ala
                2595                    2600                    2605

Lys Gly Thr Trp Arg Lys Ile Lys Glu Asn Glu Phe Ser Pro Thr Asn
                2610                    2615                    2620

Ser Thr Ser Gln Thr Val Ser Ser Gly Ala Thr Asn Gly Ala Glu Ser
                2625                    2630                    2635                    2640

Lys Thr Leu Ile Tyr Gln Met Ala Pro Ala Val Ser Lys Thr Glu Asp
                2645                    2650                    2655

Val Trp Val Arg Ile Glu Asp Cys Pro Ile Asn Asn Pro Arg Ser Gly
                2660                    2665                    2670

Arg Ser Pro Thr Gly Asn Thr Pro Pro Val Ile Asp Ser Val Ser Glu
                2675                    2680                    2685

FIG. 3Y

Lys Ala Asn Pro Asn Ile Lys Asp Ser Lys Asp Asn Gln Ala Lys Gln
2690                          2695                          2700

Asn Val Gly Asn Gly Ser Val Pro Met Arg Thr Val Gly Leu Glu Asn
2705                          2710                          2715                     2720

Arg Leu Thr Ser Phe Ile Gln Val Asp Ala Pro Asp Gln Lys Gly Thr
                    2725                          2730                          2735

Glu Ile Lys Pro Gly Gln Asn Asn Pro Val Pro Val Ser Glu Thr Asn
                    2740                          2745                          2750

Glu Ser Pro Ile Val Glu Arg Thr Pro Phe Ser Ser Ser Ser Ser Ser
2755                          2760                          2765

Lys His Ser Ser Pro Ser Gly Thr Val Ala Ala Arg Val Thr Pro Phe
2770                          2775                          2780

Asn Tyr Asn Pro Ser Pro Arg Lys Ser Ser Ala Asp Ser Thr Ser Ala
2785                          2790                          2795                     2800

FIG. 3Z

Arg Pro Ser Gln Ile Pro Thr Pro Val Asn Asn Asn Thr Lys Lys Arg
2805 2810 2815

Asp Ser Lys Thr Asp Ser Ser Thr Glu Ser Ser Gly Thr Gln Ser Pro Lys
2820 2825 2830

Arg His Ser Gly Ser Tyr Leu Val Thr Ser Val
2835 2840

FIG. 4A

```
APC    203  LGTCQDMEKRAQRRIARIQQIEKDILRIRQL  233
                ::  ::  ||||||  :|    |     |
RAL2   576  LTGAKGLQLRALRRIARIEQGGTAISPTSPL  606
```

FIG. 4B

```
APC      453  MKLSFDEEHRHAMNELGGLQAIAELLQVD       481
                :    :   ||:||||   :  :
M3 MAChR 249  LYWRIYKETEKRTKELAGLQASGTEAETE       277
              ||  :    :  |:   |||||
MCC      220  LYPNLAEERSRWEKELAGLREENESLTAM       248
                :    :   ||:||   |   |
APC      453  MKLSFDEEHRHAMNELGGLQAIAELLQVD       481
```

FIG. 6A

```
                                                                          55
GCA GTC GCC GCT CCA GTC TAT CCG GCA CTA GGA ACA GCC CCG GGN GGC GAG ACG
Ala Val Ala Ala Pro Val Tyr Pro Ala Leu Gly Thr Ala Pro Gly Gly Glu Thr
 28                                                                      109

GTC CCC GCC ATG TCT GCG GCC ATG GAG AGG TTC GAC CGG TTC CTG CAC GAG
Val Pro Ala MET Ser Ala Ala MET Glu Arg Phe Asp Arg Phe Leu His Glu
 82                                                                      163

AAG AAC TGC ATG ACT GAC CTT CTG GCC AAG CTC GAG GCC AAA ACC GGC GTG AAC
Lys Asn Cys MET Thr Asp Leu Leu Ala Lys Leu Glu Ala Lys Thr Gly Val Asn
136                                                                      217

AGG AGC TTC ATC GCT CTT GGT GTC ATC GGA CTG GTG GCC TTG TAC CTG GTG TTC
Arg Ser Phe Ile Ala Leu Gly Val Ile Gly Leu Val Ala Leu Tyr Leu Val Phe
190                                                                      271

GGT TAT GGA GCC TCT CTC TGC AAC CTG ATA GGA TTT GGC TAC CCA GCC TAC
Gly Tyr Gly Ala Ser Leu Cys Asn Leu Ile Gly Phe Gly Tyr Pro Ala Tyr
244                                                                      325

ATC TCA ATT AAA GCT ATA GAG AGT CCC AAC AAA GAA GAT GAT ACC CAG TGG CTG
Ile Ser Ile Lys Ala Ile Glu Ser Pro Asn Lys Glu Asp Asp Thr Gln Trp Leu
298                                                                      379

ACC TAC TGG GTA GTG TAT GGT GTG TTC TTC GAA ATT GCT CTG TTC TCT GAT ATC
Thr Tyr Trp Val Val Tyr Gly Val Phe Phe Glu Ile Ala Leu Phe Ser Asp Ile
352                                                                      433

TTC CTG TCA TGG CCG TTC CCC TTC TAC ATG TAC CTG AAG TGT CTC CTG CTG TGG
Phe Leu Ser Trp Pro Phe Pro Phe Tyr MET Tyr Leu Lys Cys Leu Leu Leu Trp
406                                                                      487

TGC ATG GCC CCG AGC TCT AAT GGG GCT GAA CTG CTC TAC AAG CGC ATC ATC
Cys MET Ala Pro Ser Ser Asn Gly Ala Glu Leu Leu Tyr Lys Arg Ile Ile
460                                                                      541

CGT CCT TTC TTC CTG AAG CAC GAG TCC CAG ATG GAC AGT GTG GTC AAG GAC CTT
Arg Pro Phe Phe Leu Lys His Glu Ser Gln MET Asp Ser Val Val Lys Asp Leu
514
```

FIG. 6B

```
                                                   568                                   595
AAA GAC AAG TCC AAA GAG ACT GCA GAT GCC ATC ACT AAA GAA GCG AAG AAA GCT
Lys Asp Lys Ser Lys Glu Thr Ala Asp Ala Ile Thr Lys Glu Ala Lys Lys Ala
                                                                     622

ACC GTG AAT TTA CTG GGT GAA GAA AAG AGC ACC TAA ACC AGA
Thr Val Asn Leu Leu Gly Glu Glu Lys Ser Thr
         640                 650                 660                 670                 680                 690                 700
CTAAACCAGA CTGGATGGAA ACTTCCTGCC CTCTCTGTAC CTTCCTACTG GAGCTTGATG TTATATTAGG
         710                 720                 730                 740                 750                 760                 770
GACTGTGGTA TAATTATTTT AATAATGTTG CCTTGGAAAC ATTTTTGAGA TATTAAAGAT TGGAATGTGT
         780                 790                 800                 810                 820                 830                 840
TGTAAGTTTC TTTGCTTACT TTTACTGTCT ATATATATAG GGAGCACTTT AAACTTAATG CAGTGGGCAG
         850                 860                 870                 880                 890                 900                 910
TGTCCACGTT TTTGGAAAAT GTATTTTGCC TCTGGGTAGG AAAAGATGTA TGTTGCTATC CTGCAGGAAA
         920                 930                 940                 950                 960                 970                 980
TATAAACTTA AAATAAAATT ATATACCCCA CAGGCTGTGT ACTTTACTGG GCTCTCCCTG CACGSATTTT
         990                1000                1010                1020                1030                1040                1050
CTCTGTAGTT ACATTTAGGR TAATCTTTAT GGTCTACTT CCTRTAATGT ACAATTTTAT ATAATTCNGR
        1060                1070                1080                1090                1100                1110                1120
AATGTTTTTA ATGTATTTGT GCACATGTAC ATATGGAAAT GTTACTGTCT GACTACANCA TGCATCATGC
        1130                1140                1150                1160                1170                1180                1190
TCATGGGGAG GGAGCAGGGG AAGGTTGTAT GTGTCATTTA TAACTTCTGT ACAGTAAGAC CACCTGCCAA
        1200                1210                1220                1230                1240                1250                1260
AAGCTGGAGG AACCATTGTG CTGGTGTGGT CTACTAAATA ATACTTTAGG AAATACGTGA TTAATATGCA
        1270                1280                1290                1300                1310                1320                1330
AGTGAACAAA GTGAGAAATG AAATCGAATG GAGATTGGCC TGGTTGTTTC CGTAGTATAT GGCATATGAA
        1340                1350                1360                1370                1380                1390                1400
```

FIG. 6C

```
TACCAGGATA GCTTTATAAA GCAGTTAGTT AGTTAGTTAC TCACTCTAGT GATAAATCGG GAAATTTACA
    1410       1420       1430       1440       1450       1460       1470
CACACACACA CACACACACA CACACACACA CACACACACA CACACACACA GAGTACCCTG TAACTCTCAA
    1480       1490       1500       1510       1520       1530       1540
TTCCCTGAAA AACTAGTAAT ACTGTCTTAT CTGCTATAAA CTTTACATAT TTGTCTATTG TCAAGATGCT
    1550       1560       1570       1580       1590       1600       1610
ACANTGGAMN CCATTTCTGG TTTTATCTTC ANAGSGGAGA NACATGTTGA TTTAGTCTTC TTTCCCAATC
    1620       1630       1640       1650       1660       1670       1680
TTCTTTTTTA AMCCAGTTTN AGGMNCTTCT GRAGATTTGY CCACCTCTGA TTACATGTAT GTTCTYGTTT
    1690       1700       1710       1720       1730       1740       1750
GTATCATKAG CAACAACATG CTAATGRCGA CACCTAGCTC TRAGMGCAAT TCTGGGAGAN TGARAGGNWG
    1760       1770       1780       1790       1800       1810       1820
TATARAGTMN CCCATAAATC GCTTGGCAAT AGTTAAGTCA ATCTATCTTC AGTTTTTCTC TGGCCTTTAA
    1830       1840       1850       1860       1870       1880       1890
GGTCAAACAC AAGAGGCTTC CCTAGTTTAC AAGTCAGAGT CACTTGTAGT CCATTAAAAT GCCCTCATCC
    1900       1910       1920       1930       1940       1950       1960
GTATTCTTTG TGTTGATAAG CTGCACAKGA CTACATAGTA AGTACAGANC AGTAAAGTTA ANNCGGATGT
    1970       1980       1990       2000       2010       2020       2030
CTCCATTGAT CTGCQAANTC GNTATAGAGA GCAATTGTC  TGGACTAGAA AATCTGAGTT TTACACCATA
    2040       2050       2060       2070       2080       2090       2100
CTGTTAAGAG TCCTTTTGAA TTAAACTAGA CTAAAACAAG TGTATAACTA AACTAACAAG ATTAAATATC
    2110       2120       2130       2140       2150       2160       2170
CAGCCAGTAC AGTATTTTTT AAGGCAAATA AAGATGATTA GCTCACCTTG AGNTAACAAT CAGGTAAGAT
    2180       2190       2200       2210       2220       2230       2240
CATNACAATG TCTCATGATG TNAANAATAT TAAAGATATC AATACTAAGT GACAGTATCA CNNCTAATAT
```

FIG. 6D

```
2250  2260        2270        2280        2290        2300        2310
      AGAGCATTTA  TTTTGGGGAG  GAAAACAGTG  GTGATTACCG  GCATTTTATT  AAACTTAAAA
AATATGGATC
2320  2330        2340        2350        2360        2370        2380
CTTGTAGAA  AGCAAACAAA  ATTGTTCTTG  GGAGAAAATC  AACTTTTAGA  TTAAAAAAT  TTTAAGTAWC
2390  2400        2410        2420        2430        2440        2450
TAGGAGTATT  TAAATCCTTT  TCCCATAAAT  AAAAGTACAG  TTTTCTTGGT  GGCAGAATGA  AAATCAGCAA
2460  2470        2480        2490        2500        2510        2520
CNTCTAGCAT  ATAGACTATA  TAATCAGATT  GACAGCATAT  AGAATATATT  ATCAGACAAG  ATGAGGAGGT
2530  2540        2550        2560        2570        2580        2590
ACAAAAGTTA  CTATTGCTCA  TAATGACTTA  CAGGCTAAAA  NTAGNTNTAA  AATACTATAT  TAAATTCTGA
2600  2610        2620        2630        2640        2650        2660
ATGCAATTT  TTTTTGTTCC  CTTGAGACCA  AAATTTAAGT  TAACTGTTGC  TGGCAGTCTA  AGTGTAAATG
2670  2680        2690        2700        2710        2720        2730
TTAACAGCAG  GAGAAGTTAA  GAATTGAGCA  GTTCTGTTGC  ATGATTTCCC  AAATGAAATA  CTGCCTTGGC
2740  2750        2760        2770        2780        2790        2800
TAGAGTTTGA  AAAACTAATT  GAGCCTGTGC  CTGGCTAGAA  AACAAGCGTT  TATTTGAATG  TGAATAGTGT
2810  2820        2830        2840        2850        2860        2870
TTCAAAGGTA  TGTAGTTACA  GAATTCCTAC  CAAACAGCTT  AAATTCTTCA  AGAAAGAATT  CCTGCAGCAG
2880  2890        2900        2910        2920        2930        2940
TTATTCCCTT  ACCTGAAGGC  TTCAATCATT  TGGATCAACA  ACTGCTACTC  TCGGGAAGAC  TCCTCTACTC
2950  2960        2970        2980        2990        3000        3010
ACAGCTGAAG  AAAATGAGCA  CACCCTTCAC  ACTGTTATCA  CCTATCCTGA  AGATGTGATA  CACTGAATGG
3020  3030        3040        3050        3060        3070        3080
AAATAAATAG  ATGTAAATAA  AATTGAGWTC  TCATTTAAAA  AAAACCATGT  GCCCAATGGG  AAAATGACCT
3090  3100        3110        3120        3130        3140        3150
CATGTTGTGG  TTTAAACAGC  AACTGCACCC  ACTAGCACAG  CCCATTGAGC  TANCCTATAT  ATACATCTCT
3160
GTCAGTGCCC  CTC
```

FIG. 7A

```
                                                        27                                            54
GGA CTC GGA AAT GAG GTC CAA GGG TAG CCA AGG ATG GCT GCA TCA TAT GAT
Gly Leu Gly Asn Glu Val Gln Gly Pro Arg MET Ala Ala Ser Tyr Asp 81                                           108
CAG TTG TTA AAG CAA GTT GAG GCA CTG AAG ATG GAG AAC TCA AAT CTT CGA CAA
Gln Leu Leu Lys Gln Val Glu Ala Leu Lys MET Glu Asn Ser Asn Leu Arg Gln 135                                           162
GAG CTA GAA GAT AAT TCC AAT CAT CTT ACA AAA CTG GAA ACT GAG GCA TCT AAT
Glu Leu Glu Asp Asn Ser Asn His Leu Thr Lys Leu Glu Thr Glu Ala Ser Asn 189                                           216
ATG AAG GAA GTA CTT AAA CAA CTA GAA AGT ATT GAA GAT GAA GCT ATG GCT
MET Lys Glu Val Leu Lys Gln Leu Glu Ser Ile Glu Asp Glu Ala MET Ala 243                                           270
TCT TCT GGA CAG ATT GAT TTA TTA CGT CTT AAA GAG CTT AAC TTA GAT AGC
Ser Ser Gly Gln Ile Asp Leu Leu Arg Leu Lys Glu Leu Asn Leu Asp Ser 297                                           324
AGT AAT TTC CCT GGA GTA AAA CTG CGG TCA AAA ATG TCC CTC CGT TCT TAT GGA
Ser Asn Phe Pro Gly Val Lys Leu Arg Ser Lys MET Ser Leu Arg Ser Tyr Gly
```

FIG. 7B

```
AGT AAT TTC CCT GGA GTA AAA CTG CGG TCA AAA ATG TCC CTC CGT TCT TAT GGA
Ser Asn Phe Pro Gly Val Lys Leu Arg Ser Lys MET Ser Leu Arg Ser Tyr Gly
                    297                                              324

AGC CGG GAA GGA TCT GTA TCA AGC CGT TCT GGA GAG TGC AGT CCT GTT CCT ATG
Ser Arg Glu Gly Ser Val Ser Ser Arg Ser Gly Glu Cys Ser Pro Val Pro MET
                    351                                              378

GGT TCA TTT CCA AGA AGA GGG TTT GTA AAT GGA AGC AGA GAA AGT ACT GGA TAT
Gly Ser Phe Pro Arg Arg Gly Phe Val Asn Gly Ser Arg Glu Ser Thr Gly Tyr
                    405                                              432

TTA GAA GAA CTT GAG AAA GAG AGG TCA TTG CTT CTT GCT GAT CTT GAC AAA GAA
Leu Glu Glu Leu Glu Lys Glu Arg Ser Leu Leu Leu Ala Asp Leu Asp Lys Glu
                    459                                              486

GAA AAG GAA AAA GAC TGG TAT TAC TYR GCT CAA CTT CAG AAT CTC ACT AAA AGA ATA
Glu Lys Glu Lys Asp Trp Tyr Tyr Ala Gln Leu Gln Asn Leu Thr Lys Arg Ile
                    513                                              540

```
GAT AGT CTT CCT TTA ACT GAA AAT TTT TCC TTA CAA ACA GAT TTG ACC AGA AGG
Asp Ser Leu Pro Leu Thr Glu Asn Phe Ser Leu Gln Thr Asp Leu Thr Arg Arg
                                                                        648
CAA TTG GAA TAT GAA GCA AGG CAA ATC AGA GTT GCG ATG GAA GAA CAA CTA GGT
Gln Leu Glu Tyr Glu Ala Arg Gln Ile Arg Val Ala MET Glu Glu Gln Leu Gly
                                                                        702
ACC TGC CAG GAT ATG GAA AAA CGA GCA CAG CGA AGA ATA GCC AGA ATT CAG CAA
Thr Cys Gln Asp MET Glu Lys Arg Ala Gln Arg Arg Ile Ala Arg Ile Gln Gln
                                                                        756
ATC GAA AAG GAC ATA CTT CGT ATA CGA CAG CTT TTA CAG TCC CAA GCA ACA GAA
Ile Glu Lys Asp Ile Leu Arg Ile Arg Gln Leu Leu Gln Ser Gln Ala Thr Glu
                                                                        810
GCA GAG AGG TCA TCT CAG AAC AAG CAT GAA ACC GGC TCA CAT GAT GCT GAG CGG
Ala Glu Arg Ser Ser Gln Asn Lys His Glu Thr Gly Ser His Asp Ala Glu Arg
                                                                        864
CAG AAT GAA GGT CAA GGA GTG GGA GAA ATC AAC ATG GCA ACT TCT GGT AAT GGT
Gln Asn Glu Gly Gln Gly Val Gly Glu Ile Asn MET Ala Thr Ser Gly Asn Gly
```

FIG. 7D

```
                                                                    918
CAG GGT TCA ACT ACA CGA ATG GAC CAT GAA ACA GCC AGT GTT TTG AGT TCT AGT
Gln Gly Ser Thr Thr Arg MET Asp His Glu Thr Ala Ser Val Leu Ser Ser Ser

972
AGC ACA CAC TCT GCA CCT CGA AGG CTG ACA AGT CAT CTG GGA ACC AAG GTG GAA
Ser Thr His Ser Ala Pro Arg Arg Leu Thr Ser His Leu Gly Thr Lys Val Glu

1026
ATG GTG TAT TCA TTG TTG TCA ATG CTT GGT ACT CAT GAT AAG GAT GAT ATG TCG
MET Val Tyr Ser Leu Leu Ser MET Leu Gly Thr His Asp Lys Asp Asp MET Ser

1080
CGA ACT TTG CTA GCT ATG TCT AGC TCC CAA GAC AGC TGT ATA TCC ATG CGA CAG
Arg Thr Leu Leu Ala MET Ser Ser Ser Gln Asp Ser Cys Ile Ser MET Arg Gln

1134
TCT GGA TGT CTT CCT CTC ATC CAG CTT TTA CAT GGC AAT GAC AAA GAC TCT
Ser Gly Cys Leu Pro Leu Ile Gln Leu Leu His Gly Asn Asp Lys Asp Ser

1188
GTA TTG TTG GGA AAT TCC CGG GGC AGT AAA GAG GCT CGG GCC AGG GCC AGT GCA
```

FIG. 7E

Val Leu Leu Gly Asn Ser Arg Gly Ser Lys Glu Ala Arg Ala Ser Ala 1215                                          1242
GCA CTC CAC AAC ATC ATT CAC TCA CAG CCT GAT GAC AAG AGA GGC AGG CGT GAA
Ala Leu His Asn Ile Ile His Ser Gln Pro Asp Asp Lys Arg Gly Arg Arg Glu 1269                                          1296
ATC CGA GTC CTT CAT CTT TTG GAA CAG ATA CGC GCT TAC TGT GAA ACC TGT TGG
Ile Arg Val Leu His Leu Leu Glu Gln Ile Arg Ala Tyr Cys Glu Thr Cys Trp 1323                                          1350
GAG TGG CAG GAA GCT CAT GAA CCA GGC ATG GAC CAG CAG GAC AAA AAT CCA ATG CCA
Glu Trp Gln Glu Ala His Glu Pro Gly MET Asp Gln Gln Asp Lys Asn Pro MET Pro 1377                                          1404
GCT CCT GTT GAA CAT CAG ATC TGT CCT GCT GTG TGT GTT CTA ATG AAA CTT TCA
Ala Pro Val Glu His Gln Ile Cys Pro Ala Val Cys Val Leu MET Lys Leu Ser 1431                                          1458
TTT GAT GAA GAG CAT AGA CAT GCA ATG AAT GAA CTA GGG GGA CTA CAG GCC ATT
Phe Asp Glu Glu His Arg His Ala MET Asn Glu Leu Gly Gly Leu Gln Ala Ile

FIG. 7F

```
                                                                            1512
      1485
GCA GAA TTA CAA GTG GAC TGT GAA ATG TAT GGG CTT ACT AAT GAC CAC TAC
Ala Glu Leu Gln Val Asp Cys Glu MET Tyr Gly Leu Thr Asn Asp His Tyr 1566
      1539
AGT ATT ACA CTA AGA CGA TAT GCT GGA ATG GCT TTG ACA AAC TTG ACT TTT GGA
Ser Ile Thr Leu Arg Arg Tyr Ala Gly MET Ala Leu Thr Asn Leu Thr Phe Gly 1620
      1593
GAT GTA GCC AAC AAG GCT ACG CTA TGC TCT ATG AAA GGC TGC ATG AGA GCA CTT
Asp Val Ala Asn Lys Ala Thr Leu Cys Ser MET Lys Gly Cys MET Arg Ala Leu 1674
      1647
GTG GCC CAA CTA AAA TCT GAA AGT GAA GAC TTA CAG CAG GTT ATT GCA AGT GTT
Val Ala Gln Leu Lys Ser Glu Ser Glu Asp Leu Gln Gln Val Ile Ala Ser Val 1728
      1701
TTG AGG AAT TTG TCT TGG CGA GCA GAT GTA AAT AGT AAA AAG ACG TTG CGA GAA
Leu Arg Asn Leu Ser Trp Arg Ala Asp Val Asn Ser Lys Lys Thr Leu Arg Glu 1782
      1755
GTT GGA AGT GTG AAA GCA TTG ATG GAA TGT GCT TTA GAA GTT AAA AAG GAA TCA
Val Gly Ser Val Lys Ala Leu MET Glu Cys Ala Leu Glu Val Lys Lys Glu Ser
```

FIG. 7G

```
                                                                              1836
ACC CTC AAA AGC GTA TTG AGT GCC TTA TGG AAT TTG TCA GCA CAT TGC ACT GAG
Thr Leu Lys Ser Val Leu Ser Ala Leu Trp Asn Leu Ser Ala His Cys Thr Glu

1890
AAT AAA GCT GAT ATA TGT GCT GTA GAT GGT GCA CTT GCA TTT TTG GTT GGC ACT
Asn Lys Ala Asp Ile Cys Ala Val Asp Gly Ala Leu Ala Phe Leu Val Gly Thr

1944
CTT ACT TAC CGG AGC CAG ACA AAC ACT TTA GCC ATT ATT GAA AGT GGA GGT GGG
Leu Thr Tyr Arg Ser Gln Thr Asn Thr Leu Ala Ile Ile Glu Ser Gly Gly Gly

1998
ATA TTA CGG AAT GTG TCC AGC TTG ATA GCT ACA AAT GAG GAC CAC AGG CAA ATC
Ile Leu Arg Asn Val Ser Ser Leu Ile Ala Thr Asn Glu Asp His Arg Gln Ile

2052
CTA AGA GAG AAC AAC TGT CTA CAA ACT TTA TTA CAA CAC TTA AAA TCT CAT AGT
Leu Arg Glu Asn Asn Cys Leu Gln Thr Leu Leu Gln His Leu Lys Ser His Ser

2106
TTG ACA ATA GTC AGT AAT GCA TGT GGA ACT TTG TGG AAT CTC TCA GCA AGA AAT
Leu Thr Ile Val Ser Asn Ala Cys Gly Thr Leu Trp Asn Leu Ser Ala Arg Asn
```

FIG. 7H

```
                                                              2160
CCT AAA GAC CAG GAA GCA TTA TGG GAC ATG GGG GCA GTT AGC ATG CTC AAG AAC
Pro Lys Asp Gln Glu Ala Leu Trp Asp MET Gly Ala Val Ser MET Leu Lys Asn

2214
CTC ATT CAT TCA AAG CAC AAA ATG ATT GCT ATG GGA AGT GCT GCA GCT TTA AGG
Leu Ile His Ser Lys His Lys MET Ile Ala MET Gly Ser Ala Ala Ala Leu Arg

2268
AAT CTC ATG GCA AAT AGG CCT GCG AAG TAC AAG GAT GCC AAT ATT ATG TCT CCT
Asn Leu MET Ala Asn Arg Pro Ala Lys Tyr Lys Asp Ala Asn Ile MET Ser Pro

2322
GGC TCA AGC TTG CCA TCT CTT CAT GTT AGG AAA CAA AAA GCC CTA GAA GCA GAA
Gly Ser Ser Leu Pro Ser Leu His Val Arg Lys Gln Lys Ala Leu Glu Ala Glu

2376
TTA GAT GCT CAG CAC TTA TCA GAA ACT TTT GAC AAT ATA GAC AAT TTA AGT CCC
Leu Asp Ala Gln His Leu Ser Glu Thr Phe Asp Asn Ile Asp Asn Leu Ser Pro
```

FIG. 71

```
                              2403                                              2430
AAG GCA TCT CAT CGT AGT AAG CAG AGA CAC AAG CAA AGT CTC TAT GGT GAT TAT
Lys Ala Ser His Arg Ser Lys Gln Arg His Lys Gln Ser Leu Tyr Gly Asp Tyr 2457                                              2484
GTT TTT GAC ACC AAT CGA CAT GAT AAT AGG TCA GAC AAT TTT AAT ACT GGC
Val Phe Asp Thr Asn Arg His Asp Asn Arg Ser Asp Asn Phe Asn Thr Gly 2511                                              2538
AAC ATG ACT GTC CTT TCA CCA TAT TTG AAT ACT ACA GTG TTA CCC AGC TCC TCT
Asn MET Thr Val Leu Ser Pro Tyr Leu Asn Thr Thr Val Leu Pro Ser Ser Ser 2565                                              2592
TCA AGA GGA AGC TTA GAT AGT TCT CGT TCT GAA AAA GAT AGA AGT TTG GAG
Ser Arg Gly Ser Leu Asp Ser Ser Arg Ser Glu Lys Asp Arg Ser Leu Glu 2619                                              2646
AGA GAA CGC GGA ATT GGT CTA GGC AAC TAC CAT CCA GCA ACA GAA AAT CCA GGA
Arg Glu Arg Gly Ile Gly Leu Gly Asn Tyr His Pro Ala Thr Glu Asn Pro Gly 2673                                              2700
ACT TCT TCA AAG CGA GGT TTG CAG ATC TCC ACC ACT GCA GCC CAG ATT GCC AAA
Thr Ser Ser Lys Arg Gly Leu Gln Ile Ser Thr Thr Ala Ala Gln Ile Ala Lys
```

FIG. 7J

```
              2727                                                         2754
GTC ATG GAA GAA GTG TCA GCC ATT CAT ACC TCT CAG GAA GAC AGA AGT TCT GGG
Val MET Glu Glu Val Ser Ala Ile His Thr Ser Gln Glu Asp Arg Ser Ser Gly 2781                                                         2808
TCT ACC ACT GAA TTA CAT TGT GTG ACA GAT GAG AGA AAT GCA CTT AGA AGA AGC
Ser Thr Thr Glu Leu His Cys Val Thr Asp Glu Arg Asn Ala Leu Arg Arg Ser 2835                                                         2862
TCT GCT GCC CAT ACA CAT TCA AAC ACT TAC AAT TTC ACT AAG TCG GAA AAT TCA
Ser Ala Ala His Thr His Ser Asn Thr Tyr Asn Phe Thr Lys Ser Glu Asn Ser 2889                                                         2916
AAT AGG ACA TGT TCT ATG CCT TAT GCC AAA TTA GAA TAC AAG AGA TCT TCA AAT
Asn Arg Thr Cys Ser MET Pro Tyr Ala Lys Leu Glu Tyr Lys Arg Ser Ser Asn 2943                                                         2970
GAT AGT AGT GTC AGT AGT TTA AAT GAT GGT TAT GGT AAA AGA GGT CAA ATG
Asp Ser Ser Val Ser Ser Leu Asn Asp Gly Tyr Gly Lys Arg Gly Gln MET
```

FIG. 7K

```
      2997                                                    3024
AAA CCC TCG ATT GAA TCC TAT GAT GAA AGT AAG TTT TGC AGT TAT
Lys Pro Ser Ile Glu Ser Tyr Asp Glu Ser Lys Phe Cys Ser Tyr 3051                                                    3078
GGT CAA TAC CCA GCC GAC CTA GCC CAT AAA ATA CAT AGT GCA AAT CAT ATG GAT
Gly Gln Tyr Pro Ala Asp Leu Ala His Lys Ile His Ser Ala Asn His MET Asp 3105                                                    3132
GAT AAT GAT GGA GAA CTA GAT ACA CCA ATA AAT TAT AGT CTT AAA TAT TCA GAT
Asp Asn Asp Gly Glu Leu Asp Thr Pro Ile Asn Tyr Ser Leu Lys Tyr Ser Asp 3159                                                    3186
GAG CAG TTG AAC TCT GGA AGG CAA AGT CCT TCA CAG AAT GAA AGA TGG GCA AGA
Glu Gln Leu Asn Ser Gly Arg Gln Ser Pro Ser Gln Asn Glu Arg Trp Ala Arg 3213                                                    3240
CCC AAA CAC ATA ATA GAA GAT ATA AAA CAA AGT GAG CAA AGA CAA TCA AGG
Pro Lys His Ile Ile Glu Asp Ile Lys Gln Ser Glu Gln Arg Gln Ser Arg 3267                                                    3294
AAT CAA AGT ACA ACT TAT CCT GTT TAT ACT GAG AGC ACT GAT GAT AAA CAC CTC
Asn Gln Ser Thr Thr Tyr Pro Val Tyr Thr Glu Ser Thr Asp Asp Lys His Leu
```

FIG. 7L

```
                3321                                                                    3348
AAG TTC CAA CCA CAT TTT GGA CAG CAG GAA TGT GTT TCT CCA TAC AGG TCA CGG
Lys Phe Gln Pro His Phe Gly Gln Gln Glu Cys Val Ser Pro Tyr Arg Ser Arg 3375                                                                    3402
GGA GCC AAT GGT TCA GAA ACA AAT CGA GTG GGT TCT AAT CAT GGA ATT AAT CAA
Gly Ala Asn Gly Ser Glu Thr Asn Arg Val Gly Ser Asn His Gly Ile Asn Gln 3429                                                                    3456
AAT GTA AGC CAG TCT TTG TGT CAA GAA GAT GAC TAT GAA GAT GAT AAG CCT ACC
Asn Val Ser Gln Ser Leu Cys Gln Glu Asp Asp Tyr Glu Asp Asp Lys Pro Thr 3483                                                                    3510
AAT TAT AGT GAA CGT TAC TCT GAA GAA GAA CAG CAT GAA GAA GAG AGA CCA
Asn Tyr Ser Glu Arg Tyr Ser Glu Glu Glu Gln His Glu Glu Glu Arg Pro 3537                                                                    3564
ACA AAT TAT AGC ATA AAA TAT GAA GAG AAA CGT CAT GTG GAT CAG CCT ATT
Thr Asn Tyr Ser Ile Lys Tyr Asn Glu Lys Arg His Val Asp Gln Pro Ile 3591                                                                    3618
```

FIG. 7M

```
GAT TAT AGT TTA AAA TAT GCC ACA GAT ATT CCT TCA TCA CAG AAA CAG TCA TTT
Asp Tyr Ser Leu Lys Tyr Ala Thr Asp Ile Pro Ser Ser Gln Lys Gln Ser Phe
                                                                            3645
TCA TTC TCA AAG AGT TCA TCT GGA CAA AGC AGT AAA ACC GAA CAT ATG TCT TCA
Ser Phe Ser Lys Ser Ser Ser Gly Gln Ser Ser Lys Thr Glu His MET Ser Ser
                                                                            3672                                      3699
AGC AGT GAG AAT ACG TCC ACA TCT AAT GCC AAG AGG CAG AAT CAG CTC
Ser Ser Glu Asn Thr Ser Thr Pro Ser Asn Ala Lys Arg Gln Asn Gln Leu
                                                                            3726                                      3753
CAT CCA AGT TCT GCA CAG AGT AGT GGT CAG CCT CAA AAG GCT GCC ACT TGC
His Pro Ser Ser Ala Gln Ser Arg Ser Gly Gln Pro Gln Lys Ala Ala Thr Cys
                                                                            3780
AAA GTT TCT TCT ATT AAC CAA GAA ACA ATA CAG ACT TAT TGT GTA GAA GAT ACT
Lys Val Ser Ser Ile Asn Gln Glu Thr Ile Gln Thr Tyr Cys Val Glu Asp Thr
                                                                            3807                                      3834
CCA ATA TGT TTT TCA AGA TGT AGT TCA TTA TCA TCT TTG TCA TCA GCT GAA GAT
Pro Ile Cys Phe Ser Arg Cys Ser Ser Leu Ser Ser Leu Ser Ser Ala Glu Asp
                                                                            3861                                      3888
```

FIG. 7N

```
                                                            3942
GAA ATA GGA TGT AAT CAG ACG ACA CAG GAA GCA GAT TCT GCT AAT ACC CTG CAA
Glu Ile Gly Cys Asn Gln Thr Thr Gln Glu Ala Asp Ser Ala Asn Thr Leu Gln
                            3915
                                                            3996
ATA GCA GAA ATA AAA GGA AAG ATT GGA ACT AGG TCA GCT GAA GAT CCT GTG AGC
Ile Ala Glu Ile Lys Gly Lys Ile Gly Thr Arg Ser Ala Glu Asp Pro Val Ser
                            3969
                                                            4050
GAA GTT CCA GCA GTG TCA CAG CAC CCT AGA ACC AAA TCC AGC AGA CTG CAG GGT
Glu Val Pro Ala Val Ser Gln His Pro Arg Thr Lys Ser Ser Arg Leu Gln Gly
                            4023
                                                            4104
TCT AGT TTA TCT TCA GAA TCA GCC AGG CAC AAA GCT GTT GAA TTT CCT TCA GGA
Ser Ser Leu Ser Ser Glu Ser Ala Arg His Lys Ala Val Glu Phe Pro Ser Gly
                            4077
                                                            4158
GCG AAA TCT CCC TCC AAA AGT GGT GCT CAG ACA CCC AAA AGT CCA CCT GAA CAC
Ala Lys Ser Pro Ser Lys Ser Gly Ala Gln Thr Pro Lys Ser Pro Pro Glu His
                            4131
                                                            4212
TAT GTT CAG GAG ACC CCA CTC ATG TTT AGC AGA TGT ACT TCT GTC AGT TCA CTT
Tyr Val Gln Glu Thr Pro Leu Met Phe Ser Arg Cys Thr Ser Val Ser Ser Leu
                            4185
```

FIG. 70

```
Tyr Val Gln Glu Thr Pro Leu MET Phe Ser Arg Cys Thr Ser Val Ser Ser Leu
                                                                            4266
GAT AGT TTT GAG AGT CGT TCG ATT GCC AGC TCC GTT CAG AGT GAA CCA TGC AGT
Asp Ser Phe Glu Ser Arg Ser Ile Ala Ser Ser Val Gln Ser Glu Pro Cys Ser
                                                                            4320
GGA ATG GTA AGT GGC ATT ATA AGC CCC AGT GAT CTT CCA GAT AGC CCT GGA CAA
Gly MET Val Ser Gly Ile Ile Ser Pro Ser Asp Leu Pro Asp Ser Pro Gly Gln
                                                                            4374
ACC ATG CCA CCA AGC AGA AGT AAA ACA CCT CCA CCT CCT CAA ACA GCT CAA
Thr MET Pro Pro Ser Arg Ser Lys Thr Pro Pro Pro Pro Gln Thr Ala Gln
                                                                            4428
ACC AAG CGA GAA GTA CCT AAA AAT GCA CCT ACT GCT GAA AAG AGA GAG AGT
Thr Lys Arg Glu Val Pro Lys Asn Ala Pro Thr Ala Glu Lys Arg Glu Ser
                                                                            4482
GGA CCT AAG CAA GCT GCA GTA AAT GCT GCA GTT CAG AGG GTC CAG GTT CTT CCA
Gly Pro Lys Gln Ala Ala Val Asn Ala Ala Val Gln Arg Val Gln Val Leu Pro
```

FIG. 7P

```
                                                                    4536
GAT GCT GAT ACT TTA CAT TTT GCC ACA GAA AGT ACT CCA GAT GGA TTT TCT
Asp Ala Asp Thr Leu His Phe Ala Thr Glu Ser Thr Pro Asp Gly Phe Ser
                                                                    4590
TGT TCA TCC AGC CTG AGT GCT CTG AGC CTC GAT GAG CCA TTT ATA CAG AAA GAT
Cys Ser Ser Ser Leu Ser Ala Leu Ser Leu Asp Glu Pro Phe Ile Gln Lys Asp
                                                                    4644
GTG GAA TTA AGA ATA ATG CCT CCA GTT CAG GAA AAT GAC AAT GGG AAT GAA ACA
Val Glu Leu Arg Ile MET Pro Pro Val Gln Glu Asn Asp Asn Gly Asn Glu Thr
                                                                    4698
GAA TCA GAG CAG CCT AAA GAA TCA AAT GAA AAC CAA GAG AAA GCA GAA AAA
Glu Ser Glu Gln Pro Lys Glu Ser Asn Glu Asn Gln Glu Lys Ala Glu Lys
                                                                    4752
ACT ATT GAT TCT GAA AAG GAC CTA TTA GAT GAT TCA GAT GAT GAT ATT GAA
Thr Ile Asp Ser Glu Lys Asp Leu Leu Asp Asp Ser Asp Asp Asp Ile Glu
                                                                    4806
ATA CTA GAA GAA TGT ATT ATT TCT GCC ATG CCA ACA AAG TCA TCA CGT AAA GGC
Ile Leu Glu Glu Cys Ile Ile Ser Ala MET Pro Thr Lys Ser Ser Arg Lys Gly
```

FIG. 70

```
                                                                                4860
AAA AAG CCA GCC CAG ACT GCT TCA AAA TTA CCT CCA CCT GTG GCA AGG AAA CCA
Lys Lys Pro Ala Gln Thr Ala Ser Lys Leu Pro Pro Pro Val Ala Arg Lys Pro

4914
AGT CAG CTG CCT GTG TAC AAA CTT CTA CCA TCA CAA AAC AGG TTG CAA CCC CAA
Ser Gln Leu Pro Val Tyr Lys Leu Leu Pro Ser Gln Asn Arg Leu Gln Pro Gln

4968
AAG CAT GTT AGT TTT ACA CCG GGG GAT GAT ATG CCA CGG GTG TAT TGT GTT GAA
Lys His Val Ser Phe Thr Pro Gly Asp Asp MET Pro Arg Val Tyr Cys Val Glu

5022
GGG ACA CCT ATA AAC TTT TCC ACA GCT ACA TCT CTA AGT GAT CTA ACA ATC GAA
Gly Thr Pro Ile Asn Phe Ser Thr Ala Thr Ser Leu Ser Asp Leu Thr Ile Glu

5076
TCC CCT CCA AAT GAG TTA GCT GCT GGA GAA GGA GTT AGA GGA GCA CAG TCA
Ser Pro Pro Asn Glu Leu Ala Ala Gly Glu Gly Val Arg Gly Ala Gln Ser

5130
GGT GAA TTT GAA AAA CGA GAT ACC ATT CCT ACA GAA GGC AGA AGT ACA GAT GAG
Gly Glu Phe Glu Lys Arg Asp Thr Ile Pro Thr Glu Gly Arg Ser Thr Asp Glu
```

FIG. 7R

```
                                                       5157                                                                 5184
GCT CAA GGA GGA AAA ACC TCA TCT GTA ACC ATA CCT GAA TTG GAT GAC AAT AAA
Ala Gln Gly Gly Lys Thr Ser Ser Val Thr Ile Pro Glu Leu Asp Asp Asn Lys 5211                                                                 5238
GCA GAG GAA GGT GAT ATT CTT GCA GAA TGC ATT AAT TCT GCT ATG CCC AAA GGG
Ala Glu Glu Gly Asp Ile Leu Ala Glu Cys Ile Asn Ser Ala MET Pro Lys Gly 5265                                                                 5292
AAA AGT CAC AAG CCT TTC CGT GTG AAA AAG ATA ATG GAC CAG GTC CAG CAA GCA
Lys Ser His Lys Pro Phe Arg Val Lys Lys Ile MET Asp Gln Val Gln Gln Ala 5319                                                                 5346
TCT GCG TCT TCT GCA CCC AAC AAT CAG TTA GAT GGT AAG AAA AAG AAG
Ser Ala Ser Ser Ala Pro Asn Asn Gln Leu Asp Gly Lys Lys Lys Lys 5373                                                                 5400
CCA ACT TCA CCA GTA AAA CCT ATA CCA CAA AAT ACT GAA TAT AGG ACA CGT GTA
Pro Thr Ser Pro Val Lys Pro Ile Pro Gln Asn Thr Glu Tyr Arg Thr Arg Val
```

FIG. 7S

```
                                                                      5454
AGA AAA AAT GCA GAC TCA AAA AAT AAT TTA AAT GCT GAG AGA GTT TTC TCA GAC
Arg Lys Asn Ala Asp Ser Lys Asn Asn Leu Asn Ala Glu Arg Val Phe Ser Asp

5508
AAC AAA GAT TCA AAG AAA CAG AAT TTG AAA AAT AAT TCC AAG GAC TTC AAT GAT
Asn Lys Asp Ser Lys Lys Gln Asn Leu Lys Asn Asn Ser Lys Asp Phe Asn Asp

5562
AAG CTC CCA AAT AAT GAA GAT AGA GTC AGA GGA AGT TTT GCT TTT GAT TCA CCT
Lys Leu Pro Asn Asn Glu Asp Arg Val Arg Gly Ser Phe Ala Phe Asp Ser Pro

5616
CAT CAT TAC ACG CCT ATT GAA GGA ACT CCT TAC TGT TTT TCA CGA AAT GAT TCT
His His Tyr Thr Pro Ile Glu Gly Thr Pro Tyr Cys Phe Ser Arg Asn Asp Ser

5670
TTG AGT TCT CTA GAT TTT GAT GAT GAT GTT GAC CTT TCC AGG GAA AAG GCT
Leu Ser Ser Leu Asp Phe Asp Asp Asp Val Asp Leu Ser Arg Glu Lys Ala

5724
GAA TTA AGA AAG GCA AAA GAA TCA GAG GCT AAA GTT ACC AGC CAC
Glu Leu Arg Lys Ala Lys Glu Asn Lys Glu Ser Glu Ala Lys Val Thr Ser His
```

FIG. 7T

```
                                                           5778
ACA GAA CTA ACC TCC AAC CAA CAA TCA GCT AAT AAG ACA CAA GCT ATT GCA AAG
Thr Glu Leu Thr Ser Asn Gln Gln Ser Ala Asn Lys Thr Gln Ala Ile Ala Lys
                                                           5832
CAG CCA ATA AAT CGA GGT CAG CCT AAA CCC ATA CTT CAG AAA CAA TCC ACT TTT
Gln Pro Ile Asn Arg Gly Gln Pro Lys Pro Ile Leu Gln Lys Gln Ser Thr Phe
                                                           5886
CCC CAG TCA TCC AAA GAC ATA CCA GAC AGA GGG GCA GCA ACT GAT GAA AAG TTA
Pro Gln Ser Ser Lys Asp Ile Pro Asp Arg Gly Ala Ala Thr Asp Glu Lys Leu
                                                           5940
CAG AAT TTT GCT ATT GAA AAT ACT CCA GTT TGC TTT TCT CAT AAT TCC TCT CTG
Gln Asn Phe Ala Ile Glu Asn Thr Pro Val Cys Phe Ser His Asn Ser Ser Leu
                                                           5994
AGT TCT CTC AGT GAC ATT GAC CAA GAA AAC AAT AAA GAA AAT GAA CCT ATC
Ser Ser Leu Ser Asp Ile Asp Gln Glu Asn Asn Lys Glu Asn Glu Pro Ile
```

FIG. 7U

```
AAA GAG ACT GAG CCC CCT GAC TCA CAG GGA GAA CCA AGT AAA CCT CAA GCA TCA
Lys Glu Thr Glu Pro Pro Asp Ser Gln Gly Glu Pro Ser Lys Pro Gln Ala Ser
6021                                                                    6048

GGC TAT GCT CCT AAA TCA TTT CAT GTT GAA GAT ACC CCA GTT TGT TTC TCA AGA
Gly Tyr Ala Pro Lys Ser Phe His Val Glu Asp Thr Pro Val Cys Phe Ser Arg
6075                                                                    6102

AAC AGT TCT CTC AGT TCT CTT AGT ATT GAC TCT GAA GAT GAC CTG TTG CAG GAA
Asn Ser Ser Leu Ser Ser Leu Ser Ile Asp Ser Glu Asp Asp Leu Leu Gln Glu
6129                                                                    6156

TGT ATA AGC TCC GCA ATG CCA AAA AAG CCT TCA AGA CTC AAG GGT GAT
Cys Ile Ser Ser Ala MET Pro Lys Lys Lys Pro Ser Arg Leu Lys Gly Asp
6183                                                                    6210

AAT GAA AAA CAT AGT CCC AGA AAT ATG GGT GGC ATA TTA GGT GAA GAT CTG ACA
Asn Glu Lys His Ser Pro Arg Asn MET Gly Gly Ile Leu Gly Glu Asp Leu Thr
6237                                                                    6264

CTT GAT TTG AAA GAT ATA CAG AGA CCA GAT TCA GAA CAT GGT CTA TCC CCT GAT
Leu Asp Leu Lys Asp Ile Gln Arg Pro Asp Ser Glu His Gly Leu Ser Pro Asp
6291                                                                    6318
```

FIG. 7V

```
TCA GAA AAT TTT GAT TGG AAA GCT ATT CAG GAA GGT GCA AAT TCC ATA GTA AGT
Ser Glu Asn Phe Asp Trp Lys Ala Ile Gln Glu Gly Ala Asn Ser Ile Val Ser
                                                                        6372

AGT TTA CAT CAA GCT GCT GCT GCA TGT TTA TCT AGA CAA GCT TCG TCT GAT
Ser Leu His Gln Ala Ala Ala Ala Cys Leu Ser Arg Gln Ala Ser Ser Asp
                                                                    6426

TCA GAT TCC ATC CTT TCC CTG AAA TCA GGA ATC TCT CTG GGA TCA CCA TTT CAT
Ser Asp Ser Ile Leu Ser Leu Lys Ser Gly Ile Ser Leu Gly Ser Pro Phe His
                                                                        6480

CTT ACA CCT GAT CAA GAA GAA AAA CCC TTT ACA AGT AAT AAA GGC CCA CGA ATT
Leu Thr Pro Asp Gln Glu Glu Lys Pro Phe Thr Ser Asn Lys Gly Pro Arg Ile
                                                                        6534

CTA AAA CCA GGG GAG AAA AGT ACA TTG GAA ACT AAA AAG ATA AAA TCT GAA AGT
Leu Lys Pro Gly Glu Lys Ser Thr Leu Glu Thr Lys Lys Ile Lys Glu Ser Ser
                                                                        6588

```
AAA ATC AAA GGA GGA AAA AAA GTT TAT AAA AGT TTG ATT ACT GGA AAA GTT
Lys Ile Lys Gly Gly Lys Lys Val Tyr Lys Ser Leu Ile Thr Gly Lys Val
                                                                    6696

CGA TCT AAT TCA GAA ATT TCA GGC CAA ATG AAA CAG CCC CTT CAA GCA AAC ATG
Arg Ser Asn Ser Glu Ile Ser Gly Gln MET Lys Gln Pro Leu Gln Ala Asn MET
                                                                    6750

CCT TCA ATC TCT CGA GGC AGG ACA ATG ATT CAT ATT CCA GGA GTT CGA AAT AGC
Pro Ser Ile Ser Arg Gly Arg Thr MET Ile His Ile Pro Gly Val Arg Asn Ser
                                                                    6804

TCC TCA AGT ACA AGT CCT GTT TCT AAA AAA GGC CCA CCC CTT AAG ACT CCA GCC
Ser Ser Ser Thr Ser Pro Val Ser Lys Lys Gly Pro Pro Leu Lys Thr Pro Ala
                                                                    6858

TCC AAA AGC CCT AGT GAA GGT CAA ACA GCC ACC ACT TCT CCT AGA GGA GCC AAG
Ser Lys Ser Pro Ser Glu Gly Gln Thr Ala Thr Thr Ser Pro Arg Gly Ala Lys
                                                                    6912

CCA TCT GTG AAA TCA GAA TTA AGC CCT GTT GCC AGG CAG ACA TCC CAA ATA GGT
Pro Ser Val Lys Ser Glu Leu Ser Pro Val Ala Arg Gln Thr Ser Gln Ile Gly
```

FIG. 7X

```
     GGG TCA AGT AAA GCA CCT TCT AGA TCA GGA TCT AGA GAT TCG ACC CCT TCA AGA    6966
     Gly Ser Ser Lys Ala Pro Ser Arg Ser Gly Ser Arg Asp Ser Thr Pro Ser Arg

6939

CCT GCC CAG CAA CCA TTA AGT AGA CCT ATA CAG TCT CCT GGC CGA AAC TCA ATT    7020
     Pro Ala Gln Gln Pro Leu Ser Arg Pro Ile Gln Ser Pro Gly Arg Asn Ser Ile

6993

TCC CCT GGT AGA AAT GGA ATA AGT CCT AAC AAA TTA TCT CAA CTT CCA AGG         7074
     Ser Pro Gly Arg Asn Gly Ile Ser Pro Asn Lys Leu Ser Gln Leu Pro Arg

7047

ACA TCA TCC CCT AGT ACT GCT TCA ACT AAG TCC TCA GGT TCT GGA AAA ATG TCA    7128
     Thr Ser Ser Pro Ser Thr Ala Ser Thr Lys Ser Ser Gly Ser Gly Lys MET Ser

7101

TAT ACA TCT CCA GGT AGA CAG ATG AGC CAA CAG AAC CTT ACC AAA CAA ACA GGT    7182
     Tyr Thr Ser Pro Gly Arg Gln MET Ser Gln Gln Asn Leu Thr Lys Gln Thr Gly

7155

TTA TCC AAG AAT GCC AGT AGT ATT CCA AGA AGT GAG TCT GCC TCC AAA GGA CTA    7236

Leu Ser Lys Asn Ala Ser Ser Ile Pro Arg Ser Glu Ser Ala Ser Lys Gly Leu

```
                                                                          7290
AAT CAG ATG AAT AAT GGT AAT GCC AAT AAA AAG GTA GAA CTT TCT AGA ATG
Asn Gln MET Asn Asn Gly Asn Ala Asn Lys Lys Val Glu Leu Ser Arg MET

7344
TCT TCA ACT AAA TCA AGT GGA AGT GAA TCT GAT AGA TCA GAA AGA CCT GTA TTA
Ser Ser Thr Lys Ser Ser Gly Ser Glu Ser Asp Arg Ser Glu Arg Pro Val Leu

7398
GTA CGC CAG TCA ACT TTC ATC AAA GAA GCT CCA AGC CCA ACC TTA AGA AGA AAA
Val Arg Gln Ser Thr Phe Ile Lys Glu Ala Pro Ser Pro Thr Leu Arg Arg Lys

7452
TTG GAG GAA TCT GCT TCA TTT GAA TCT CTT TCT CCA TCA TCT AGA CCA GCT TCT
Leu Glu Glu Ser Ala Ser Phe Glu Ser Leu Ser Pro Ser Ser Arg Pro Ala Ser

7506
CCC ACT AGG TCC CAG GCA CAA ACT CCA GTT TTA AGT CCT TCC CTT CCT GAT ATG
Pro Thr Arg Ser Gln Ala Gln Thr Pro Val Leu Ser Pro Ser Leu Pro Asp MET
```

FIG. 72

```
     7533
TCT CTA TCC ACA CAT TCG TCT GTT CAG GCT GGT GGA TGG CGA AAA CTC CCA CCT
Ser Leu Ser Thr His Ser Ser Val Gln Ala Gly Gly Trp Arg Lys Leu Pro Pro
                                                                    7560

7587
AAT CTC AGT CCC ACT ATA GAG TAT AAT GAT GGA AGA CCA GCA AAG CGC CAT GAT
Asn Leu Ser Pro Thr Ile Glu Tyr Asn Asp Gly Arg Pro Ala Lys Arg His Asp
                                                                    7614

7641
ATT GCA CGG TCT CAT TCT GAA AGT CCT TCT AGA CTT CCA ATC AAT AGG TCA GGA
Ile Ala Arg Ser His Ser Glu Ser Pro Ser Arg Leu Pro Ile Asn Arg Ser Gly
                                                                    7668

7695
ACC TGG AAA CGT GAG CAC AGC AAA CAT TCA TCC CTT CCT CGA GTA AGC ACT
Thr Trp Lys Arg Glu His Ser Lys His Ser Ser Leu Pro Arg Val Ser Thr
                                                                    7722

7749
TGG AGA AGA ACT GGA AGT TCA TCT ATT CTT TCT GCT TCA GAA TCC AGT
Trp Arg Arg Thr Gly Ser Ser Ser Ile Leu Ser Ala Ser Glu Ser Ser
                                                                    7776

7803
GAA AAA GCA AAA AGT GAG GAT GAA AAA CAT GTG AAC TCT ATT TCA GGA ACC AAA
Glu Lys Ala Lys Ser Glu Asp Glu Lys His Val Asn Ser Ile Ser Gly Thr Lys
                                                                    7830
```

FIG. 7A-1

```
        7857                                                    7884
CAA AGT AAA GAA AAC CAA GTA TCC GCA AAA GGA ACA TGG AGA AAA ATA AAA GAA
Gln Ser Lys Glu Asn Gln Val Ser Ala Lys Gly Thr Trp Arg Lys Ile Lys Glu 7911                                                    7938
AAT GAA TTT TCT CCC ACA AAT AGT ACT TCT CAG ACC GTT TCC TCA GGT GCT ACA
Asn Glu Phe Ser Pro Thr Asn Ser Thr Ser Gln Thr Val Ser Ser Gly Ala Thr 7965                                                    7992
AAT GGT GCT GAA TCA AAG ACT CTA ATT TAT CAA ATG GCA CCT GCT GTT TCT AAA
Asn Gly Ala Glu Ser Lys Thr Leu Ile Tyr Gln MET Ala Pro Ala Val Ser Lys 8019                                                    8046
ACA GAG GAT GTT TGG GTG AGA ATT GAG GAC TGT CCC ATT AAC AAT CCT AGA TCT
Thr Glu Asp Val Trp Val Arg Ile Glu Asp Cys Pro Ile Asn Asn Pro Arg Ser 8073                                                    8100
GGA AGA TCT CCC ACA GGT AAT ACT CCC CCG GTG ATT GAC AGT GTT TCA GAA AAG
Gly Arg Ser Pro Thr Gly Asn Thr Pro Pro Val Ile Asp Ser Val Ser Glu Lys 8127                                                    8154
GCA AAT CCA AAC ATT AAA GAT TCA AAA GAT AAT CAG GCA AAA CAA AAT GTG GGT
Ala Asn Pro Asn Ile Lys Asp Ser Lys Asp Asn Gln Ala Lys Gln Asn Val Gly
```

FIG. 7B-1

```
                                                                    8208
      8181                                    GAA AAT CGC CTG ACC TCC TTT
AAT GGC AGT GTT CCC ATG CGT ACC GTG GGT TTG   Glu Asn Arg Leu Thr Ser Phe
Asn Gly Ser Val Pro MET Arg Thr Val Gly Leu 8262
      8235                                    GAG ATA AAA CCA GGA CAA AAT
ATT CAG GTG GAT GCC CCT GAC CAA AAA GGA ACT   Glu Ile Lys Pro Gly Gln Asn
Ile Gln Val Asp Ala Pro Asp Gln Lys Gly Thr 8316
      8289                                    CCT ATA GTG GAA CGT ACC CCA
AAT CCT GTC CCT GTA TCA GAG ACT AAT GAA AGT   Pro Ile Val Glu Arg Thr Pro
Asn Pro Val Pro Val Ser Glu Thr Asn Glu Ser 8370
      8343                                    CCT AGT GGG ACT GTT GCT GCC
TTC AGT TCT AGC AGC AAA CAC AGT TCA           Pro Ser Gly Thr Val Ala Ala
Phe Ser Ser Ser Ser Lys His Ser Ser 8424
      8397                                    AGC CCT AGG AAA AGC AGC GCA GAT AGC
AGA GTG ACT CCT TTT AAT TAC AAC CCA           Ser Pro Arg Lys Ser Ser Ala Asp Ser
Arg Val Thr Pro Phe Asn Tyr Asn Pro
```

FIG. 7C-1

```
                                                                        8478
ACT TCA GCT CGG CCA TCT CAG ATC CCA ACT CCA GTG AAT AAC ACA AAG AAG
Thr Ser Ala Arg Pro Ser Gln Ile Pro Thr Pro Val Asn Asn Thr Lys Lys

8532
CGA GAT TCC AAA ACT GAC AGC ACA GAA TCC AGT GGA ACC CAA AGT CCT AAG CGC
Arg Asp Ser Lys Thr Asp Ser Thr Glu Ser Ser Gly Thr Gln Ser Pro Lys Arg

8559
CAT TCT GGG TCT TAC CTT GTG ACA TCT GTT TAA .
His Ser Gly Ser Tyr Leu Val Thr Ser Val 8570       8580       8590       8600       8610
AAGAG AGGAAGAATG AAACTAAGAA AATTCTATGT TAATTACAAC 8620       8630       8640       8650       8660       8670       8680
TGCTATATAG ACATTTGTT TCAAATGAAA CTTTAAAAGA CTGAAAAATT TTGTAAATAG GTTTGATTCT 8690       8700       8710       8720       8730       8740       8750
TGTTAGAGGG TTTTTGTTCT GGAAGCCATA TTTGATAGTA TACTTTGTCT TCACTGGTCT TATTTTGGGA 8760       8770       8780       8790       8800       8810       8820
GGCACTCTTG ATGGTTAGGS AAAAAAATAGK AAAGCCAAGT ATGTTTGTAC AGTATGTTTT ACATGTATTT 8830       8840       8850       8860       8870       8880       8890
AAAGTAGCAT CCCATCCCAA CTTCCYTTAA TTATTGCTTG TCYTAAAATA ATGAACACTA CAGATAGGAA
```

FIG. 7D-I

```
        8900        8910        8920        8930        8940        8950        8960
  ATATGATATA  TTGCTGTTAT  CAATCATTTC  TAGATTATAA  ACTGACTAAA  CTTACATCAG  GGGAAAATTG 8970        8980        8990        9000        9010        9020        9030
  GTATTTATGC  AAAAAAAAAA  TGTTTTTGTC  CTTGTGAGTC  CATCTAACAT  CATAATTAAT  CATGTGGCTG 9040        9050        9060        9070        9080        9090        9100
  TGAAATTCAC  AGTAATATGG  TTCCCGATGA  ACAAGTTTAC  CCAGCCTGCT  TTGCTTNACT  GCATGAATGA 9110        9120        9130        9140        9150        9160        9170
  AACTGATGGT  TCAATTTCAG  AAGTAAATGAT  TAACAGTTAT  GTGGTCACAT  GATGTGCATA  GAGATAGCTA 9180        9190        9200        9210        9220        9230        9240
  CAGTGTAATA  ATTTACACTA  TTTTGTGCTC  CAAACAAAAC  AAAAATCTGT  GTAACTGTAA  AACATTGAAT 9250        9260        9270        9280        9290        9300        9310
  GAAACTATTT  TACCTGAACT  AGATTTTATC  TGAAAGTAGG  TAGAATTTTT  GCTATGCTGT  AATTTGTTGT 9320        9330        9340        9350        9360        9370        9380
  ATATTCTGGT  ATTTGAGGTG  AGATGGCTGC  TCTTTKATTA  ATGAGACATG  AATTGTGTCT  CAACAGAAAC 9390        9400        9410        9420        9430        9440        9450
  TAAATGAACA  TTTCAGAATA  AATTATTGCT  GTATGTAAAC  TGTTACTGAA  ATTGGTATTT  GTTTGAAGGG 9460        9470        9480        9490        9500        9510        9520
  TSTTGTTTCA  CATTTGTATT  AATTAAATGT  TTAAAATGCC  TCTTTTAAAA  GCTTATATAA  ATTTTTTNCT
```

FIG. 7E-1

```
9530       9540       9550       9560       9570       9580       9590
TCAGCTTCTA TGCATTAAGA GTAAAATTCC TCTTACTGTA ATAAAAACAR TTGAAGAAGA CTGTTGCCAC 9600       9610       9620       9630       9640       9650       9660
TTAACCATTC CATGCGTTGG CACTTATCTA TTCCTGAAAT TTCTTTTATG TGATTAGCTC ATCTTGATTT 9670       9680       9690       9700       9710       9720       9730
TWAAYATTTT TCCACTTAAA CTTTTTTTTC TTACTCCACT GGAGCTCAGT AAAAGTAAAT TCATGTAATA 9740       9750       9760       9770       9780       9790       9800
GCAATGCAAG CAGCCTAGCA ATTGAGCATA ATAGGCCCAC ATAATTTCCT CTTTCTTAAT 9810       9820       9830       9840       9850       9860       9870
AWTATAGAAT TCTGTACTTG AAATTRATTC TTAGACATTG CAGTCTCTTC GAGGCTTTAC AGTGTAAACT 9880       9890       9900       9910       9920       9930       9940
GTCTTGCCCC TTCATCTTCT TGTTGCAACT GGGTCTGACA TGAACACTTT TTATCACCCT GTATGTTAGG 9950       9960       9970       9980       9990       10000      10010
GCAAGATCTC AGCAGTGAAG TATAATCAGC ACTTTGCCAT GCTCANRAAA TTCAAATCAC ATGGAACTTT
```

FIG. 7F-1

| | | | | | | |
|---|---|---|---|---|---|---|
| 10020 | 10030 | 10040 | 10050 | 10060 | 10070 | 10080 |
| AGAGGTAGAT | TTAATACGAT | TAAGATATTC | AGAAGTATAT | TTTAGAATCC | CTGCCTGTTA | AGGAAACTTT |
| 10090 | 10100 | 10110 | 10120 | 10130 | 10140 | 10150 |
| ATTTGTGGTA | GGTACAGTTC | TGGGGTACAT | GTTAAGTGTC | CCCTTATACA | GTGGAGGGAA | GTCTTCCTTC |
| 10160 | 10170 | 10180 | 10190 | 10200 | 10210 | 10220 |
| CTGAAGGRAA | ATAAACTGAC | ACTTATTAAC | TAAGATAATT | TACTTAATAT | ATCTYCCCTG | ATTTGTTTTA |
| 10230 | 10240 | 10250 | 10260 | 10270 | 10280 | 10290 |
| AAAGATCAGA | GGGTGACTGA | TGATACATGC | ATACATATTT | GTTGAATAAA | TTTTTAGTTA | TTTTTAGTGA |
| 10300 | 10310 | 10320 | 10330 | 10340 | 10350 | 10360 |
| TAAGANTCAT | ACACTCTGTA | TTTGGGGAGR | GAAAACCTTT | TTAAGCATGG | TGGGGCACTC | AGATAGGNGT |
| 10370 | 10380 | | | | | |
| NAATACACCT | ACCTGGGTGGT | CAT | | | | |

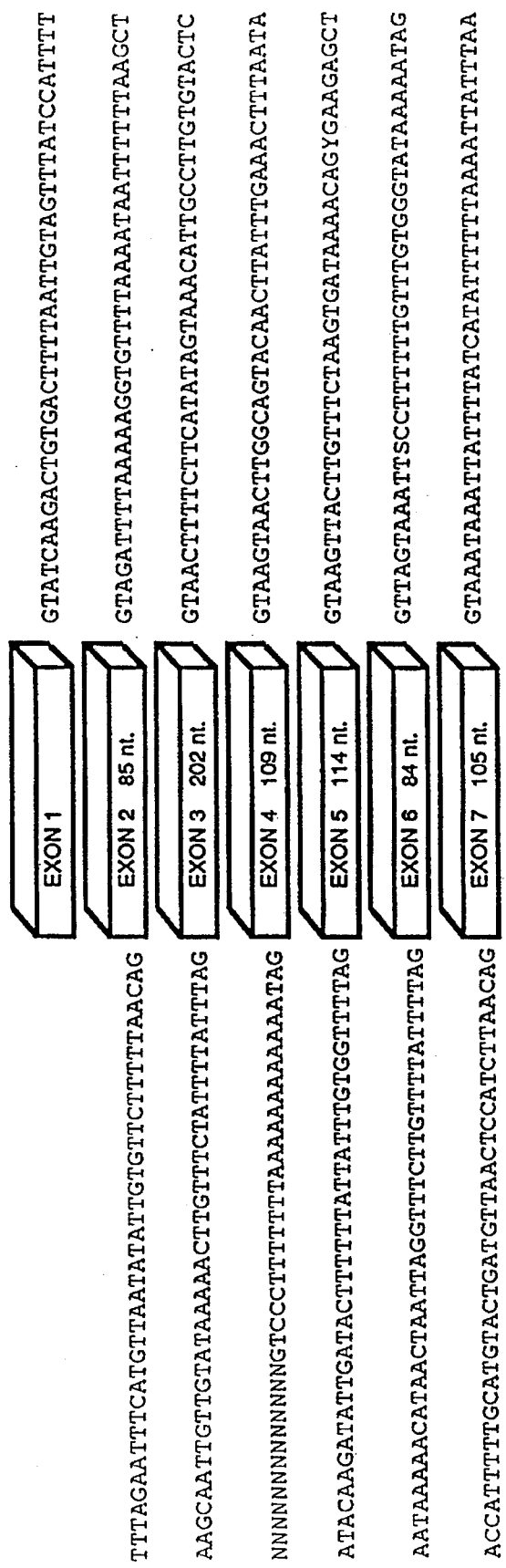

DETECTION OF INHERITED AND SOMATIC MUTATIONS OF APC GENE IN COLORECTAL CANCER OF HUMANS

This application is a division of application Ser. No. 07/741,940, filed Aug. 8, 1991, which issued as U.S. Pat. No. 5,352,775.

The U.S. Government has a paid-up license in this invention and the right in limited circumstances to require the patent owner to license others on reasonable terms as provided for by the terms of grants awarded by the National Institutes of Health.

TECHNICAL AREA OF THE INVENTION

The invention relates to the area of cancer diagnostics and therapeutics. More particularly, the invention relates to detection of the germline and somatic alterations of wild-type APC genes. In addition, it relates to therapeutic intervention to restore-the function of APC (*adenomatous Poliposis Coli*) gene product.

BACKGROUND OF THE INVENTION

According to the model of Knudson for tumorigenesis (Cancer Research, Vol. 45, p. 1482, 1985), there are tumor suppressor genes in all normal cells which, when they become non-functional due to mutation, cause neoplastic development. Evidence for this model has been found in the cases of retinoblastoma and colorectal tumors. The implicated suppressor genes in those tumors, RB (retinoblastoma), p53 (protein having a molecular weight of 53 kDa), (deleted in colorectal cancer) and MCC (mutated in colorectal cancer), were found to be deleted or altered in many cases of the tumors studied. (Hansen and Cavenee, Cancer Research, Vol. 47, pp. 5518–5527 (1987); Baker et al., Science, Vol. 244, p. 217 (1989); Fearon et al., Science, Vol. 247, p. 49 (1990); Kinzler et al. Science Vol. 251. p. 1366 (1991).)

In order to fully understand the pathogenesis of tumors, it will be necessary to identify the other suppressor genes that play a role in the tumorigenesis process. Prominent among these is the one(s) presumptively located at 5q21. Cytogenetic (Herrera et al., *Am J. Med. Genet.*, Vol. 25, p. 473 (1986) and linkage (Leppert et al., Science, Vol. 238, p. 1411 (1987); Bodmer et al., Nature, Vol. 328, p. 614 (1987)) studies have shown that this chromosome region harbors the gene responsible for familial adenomatous polyposis (FAP) and Gardner's Syndrome (GS). FAP is an autosomal-dominant, inherited disease in which affected individuals develop hundreds to thousands of adenomatous polyps, some of which progress to malignancy. GS is a variant of FAP in which desmoid tumors, osteomas and other soft tissue tumors occur together with multiple adenomas of the colon and rectum. A less severe form of polyposis has been identified in which only a few (2–40) polyps develop. This condition also is familial and is linked to the same chromosomal markers as FAP and GS (Leppert et al., New England Journal of Medicine, Vol. 322, pp. 904–908, 1990.) Additionally, this chromosomal region is often deleted from the adenomas (Vogelstein et al., N. Engl. J. Med., Vol. 319, p. 525 (1988)) and carcinomas (Vogelstein et al., N. Engl. J. Med., Vol. 319, p. 525 (1988); Solomon et al., Nature, Vol. 328, p. 616 (1987); Sasaki et al., Cancer Research, Vol. 49, p. 4402 (1989); Delattre et al., Lancet, Vol. 2, p. 353 (1989); and Ashton-Rickardt et al., Oncogene, Vol. 4, p. 1169 (1989)) of patients without FAP (sporadic tumors). Thus, a putative suppressor gene on chromosome 5q21 appears to play a role in the early stages of colorectal neoplasia in both sporadic and familial tumors.

Although the MCC gene has been identified on 5q21 as a candidate suppressor gene, it does not appear to be altered in FAP or GS patients. Thus there is a need in the art for investigations of this chromosomal region to identify genes and to determine if any of such genes are associated with FAP and/or GS and the process of tumorigenesis.

SUMMARY OF THE INVENTION

It is an object of the present invention to provide a method for diagnosing and prognosing a neoplastic tissue of a human.

It is another object of the invention to provide a method of detecting genetic predisposition to cancer.

It is another object of the invention to provide a method of supplying wild-type APC gene function to a cell which has lost said gene function.

It is yet another object of the invention to provide a kit for determination of the nucleotide sequence of APC alleles by the polymerase chain reaction.

It is still another object of the invention to provide nucleic acid probes for detection of mutations in the human APC gene.

It is still another object of the invention to provide a cDNA molecule encoding the APC gene product.

It is yet another object of the invention to provide a preparation of the human APC protein.

It is another object of the invention to provide a method of screening for genetic predisposition to cancer.

It is an object of the invention to provide methods of testing therapeutic agents for the ability to suppress neoplasia.

It is still another object of the invention to provide animals carrying mutant APC alleles.

These and other objects of the invention are provided by one or more of the embodiments which are described below. In one embodiment of the present invention a method of diagnosing or prognosing a neoplastic tissue of a human is provided comprising: detecting somatic alteration of wild-type APC genes or their expression products in a sporadic colorectal cancer tissue, said alteration indicating neoplasia of the tissue.

In yet another embodiment a method is provided of detecting genetic predisposition to cancer in a human including familial adenomatous polyposis (FAP) and Gardner's Syndrome (GS), comprising: isolating a human sample selected from the group consisting of blood and fetal tissue; detecting alteration of wild-type APC gene coding sequences or their expression products from the sample, said alteration indicating genetic predisposition to cancer.

In another embodiment of the present invention a method is provided for supplying wild-type APC gene function to a cell which has lost said gene function by virtue of a mutation in the APC gene, comprising: introducing a wild-type APC gene into a cell which has lost said gene function such that said wild-type gene is expressed in the cell.

In another embodiment a method of supplying wild-type APC gene function to a cell is provided comprising: introducing a portion of a wild-type APC gene into a cell which has lost said gene function such that said portion is expressed in the cell, said portion encoding a part of the APC protein which is required for non-neoplastic growth of said cell. APC protein can also be applied to cells or administered to animals to remediate for mutant APC genes. Synthetic peptides or drugs can also be used to mimic APC function in cells which have altered APC expression.

In yet another embodiment a pair of single stranded primers is provided for determination of the nucleotide sequence of the APC gene by polymerase chain reaction. The sequence of said pair of single stranded DNA primers is derived from chromosome 5q band 21, said pair of primers allowing synthesis of APC gene coding sequences.

In still another embodiment of the invention a nucleic acid probe is provided which is complementary to human wild-type APC gene coding sequences and which can form mismatches with mutant APC genes, thereby allowing their detection by enzymatic or chemical cleavage or by shifts in electrophoretic mobility.

In another embodiment of the invention a method is provided for detecting the presence of a neoplastic tissue in a human. The method comprises isolating a body sample from a human; detecting in said sample alteration of a wild-type APC gene sequence or wild-type APC expression product, said alteration indicating the presence of a neoplastic tissue in the human.

In still another embodiment a cDNA molecule is provided which comprises the coding sequence of the APC gene.

In even another embodiment a preparation of the human APC protein is provided which is substantially free of other human proteins. The amino acid sequence of the protein is shown in FIG. 3 or 7 (SEQ ID NO: 2).

In yet another embodiment of the invention a method is provided for screening for genetic predisposition to cancer, including familial adenomatous polyposis (FAP) and Gardner's Syndrome (GS), in a human. The method comprises: detecting among kindred persons the presence of a DNA polymorphism which is linked to a mutant APC allele in an individual having a genetic predisposition to cancer, said kindred being genetically related to the individual, the presence of said polymorphism suggesting a predisposition to cancer.

In another embodiment of the invention a method of testing therapeutic agents for the ability to suppress a neoplastically transformed phenotype is provided. The method comprises: applying a test substance to a cultured epithelial cell which carries a mutation in an APC allele; and determining whether said test substance suppresses the neoplastically transformed phenotype of the cell.

In another embodiment of the invention a method of testing therapeutic agents for the ability to suppress a neoplastically transformed phenotype is provided. The method comprises: administering a test substance to an animal which carries a mutant APC allele; and determining whether said test substance prevents or suppresses the growth of tumors.

In still other embodiments of the invention transgenic animals are provided. The animals carry a mutant APC allele from a second animal species or have been genetically engineered to contain an insertion mutation which disrupts an APC allele.

The present invention provides the art with the information that the APC gene, a heretofore unknown gene is, in fact, a target of mutational alterations on chromosome 5q21 and that these alterations are associated with the process of tumorigenesis. This information allows highly specific assays to be performed to assess the neoplastic status of a particular tissue or the predisposition to cancer of an individual. This invention has applicability to Familial Adenomatous Polyposis, sporadic colorectal cancers, Gardner's Syndrome, as well as the less severe familial polyposis discusses above.

The cDNA sequence of the TB2 gene was determined from the YS-39 clone derived as described in the text. This clone consisted of 2300 bp and defined an ORF of 185 amino acids beginning at nucleotide 1. Only the predicted amino acids are shown. The carboxy terminal end of the ORF has apparently been identified, but the 5' end of the TB2 transcript has not been precisely determined.

Figure 1A:
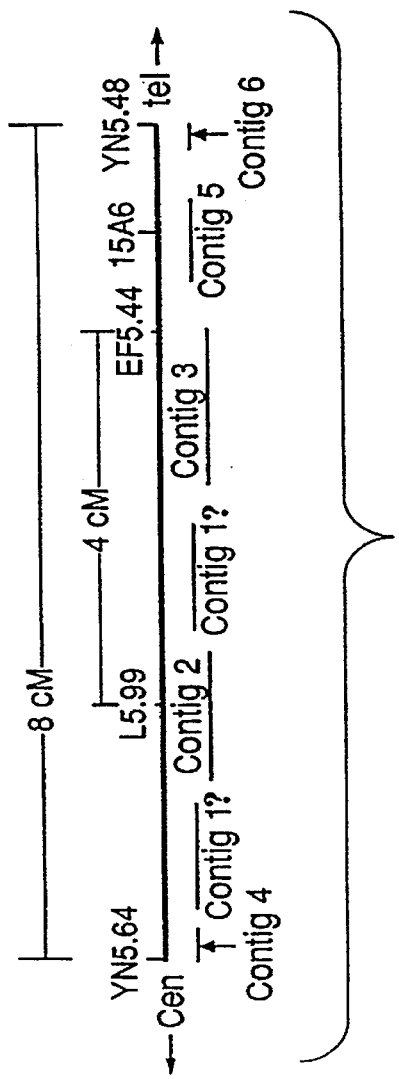
FIG. 1A shows an overview of yeast artificial chromosome (YAC) contigs (contiguous stretches of sequence). Genetic distances between selected RFLP markers from within the contigs are shown in centiMorgans.
Figures 1, 1B:
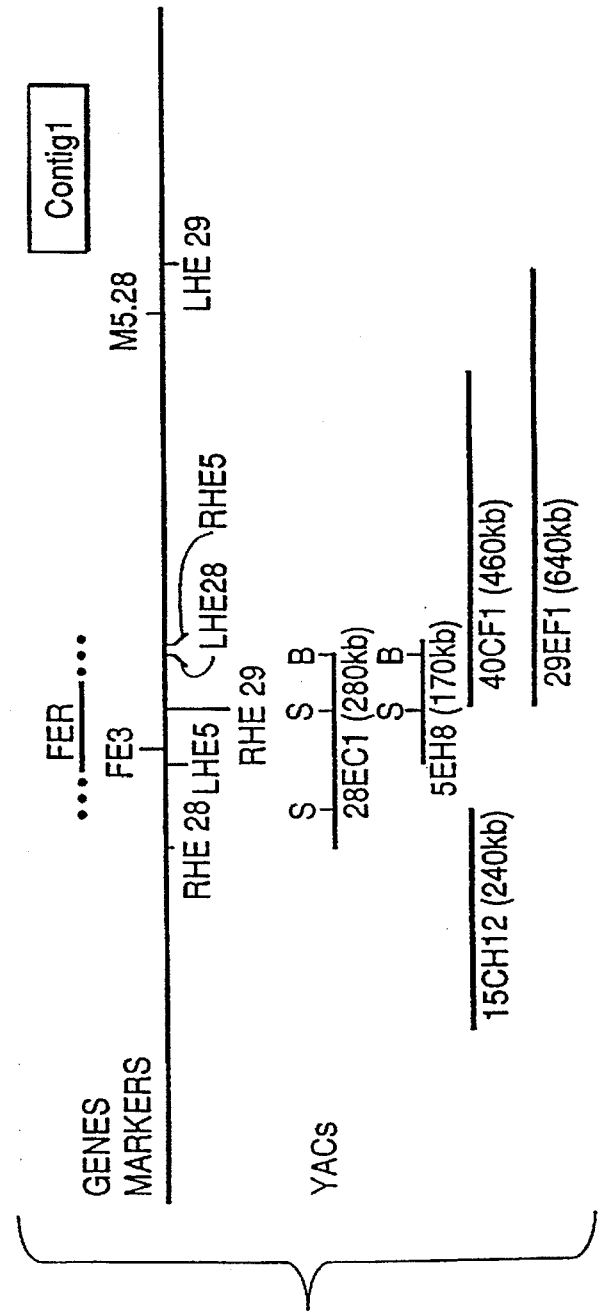
FIG. 1B shows a detailed map of the three central contigs. The position of the six identified genes from within the FAP region is shown; the 5' and 3' ends of the transcripts from these genes have in general not yet been isolated, as indicated by the string of dots surrounding the bars denoting the genes' positions. Selected restriction endonuclease recognition sites are indicated. B, BssH2; S, SstII; M, MluI; N, NruI.
Figures 1, 1B, 2:
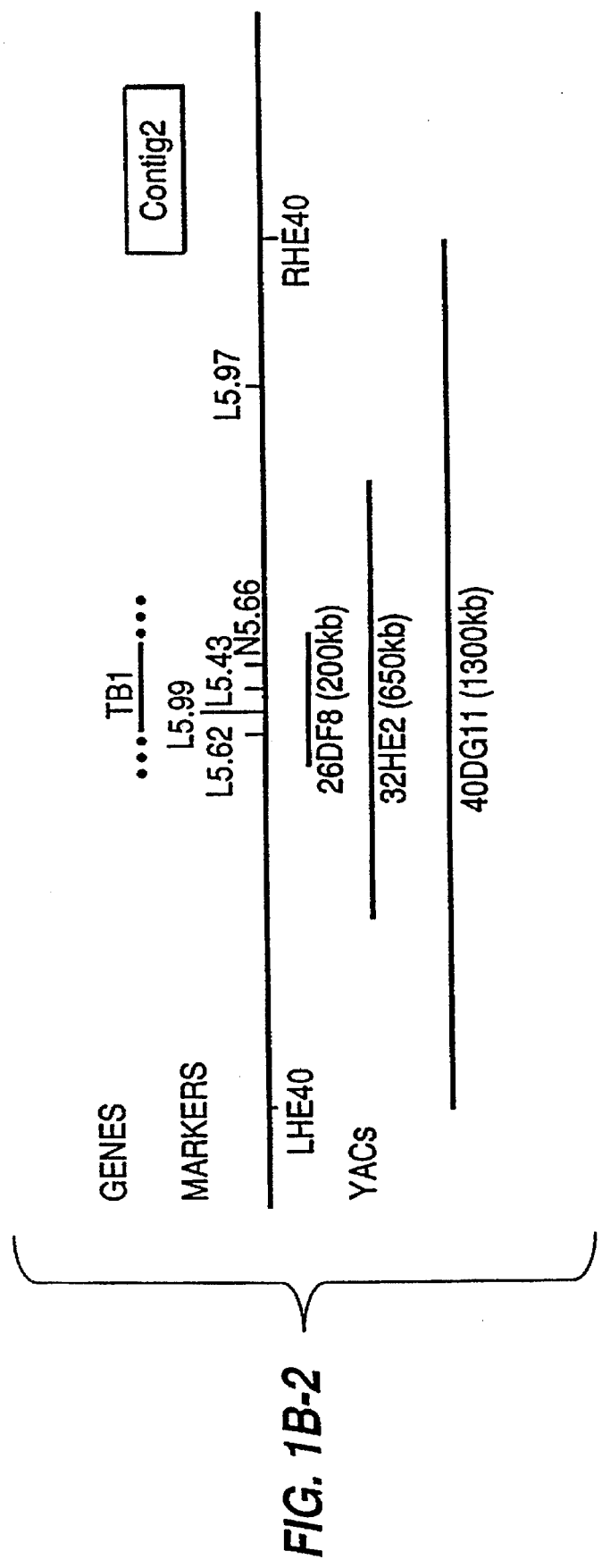
Figures 1, 1B, 2, 3:
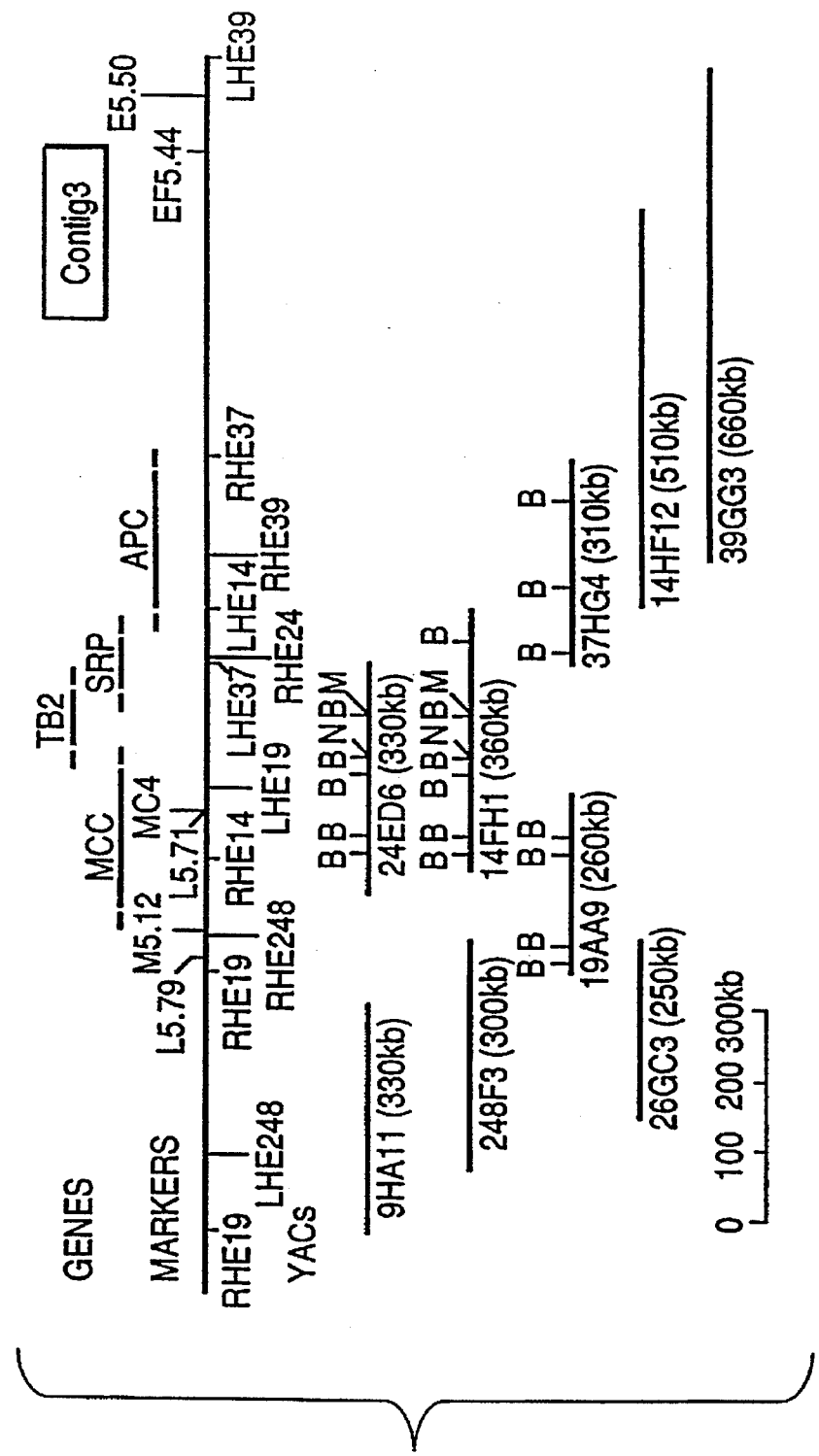

FIG. 3 shows the sequence of the APC gene product (SEQ ID NO: 2). The cDNA sequence was determined through the analysis of 87 cDNA clones derived from normal colon, liver, and brain. A total of 8973 bp were contained within overlapping cDNA clones, defining an ORF of 2842 amino acids. In frame stop codons surrounded this ORF, as described in the text, suggesting that the entire APC gene product was represented in the ORF illustrated. Only the predicted amino acids are shown.

FIGS. 4A and 4B shows the local similarity between human APC (SEQ ID NO: 2) and ral2 (SEQ ID NO: 8) of yeast. Local similarity among the APC (SEQ ID NO: 2) and MCC genes (SEQ ID NO: 5) and the m3 muscarinic acetylcholine receptor is shown. The region of the mAChR shown corresponds to that responsible for coupling the receptor to G proteins. The connecting lines indicate identities; dots indicate related amino acids residues.

Figure 5:
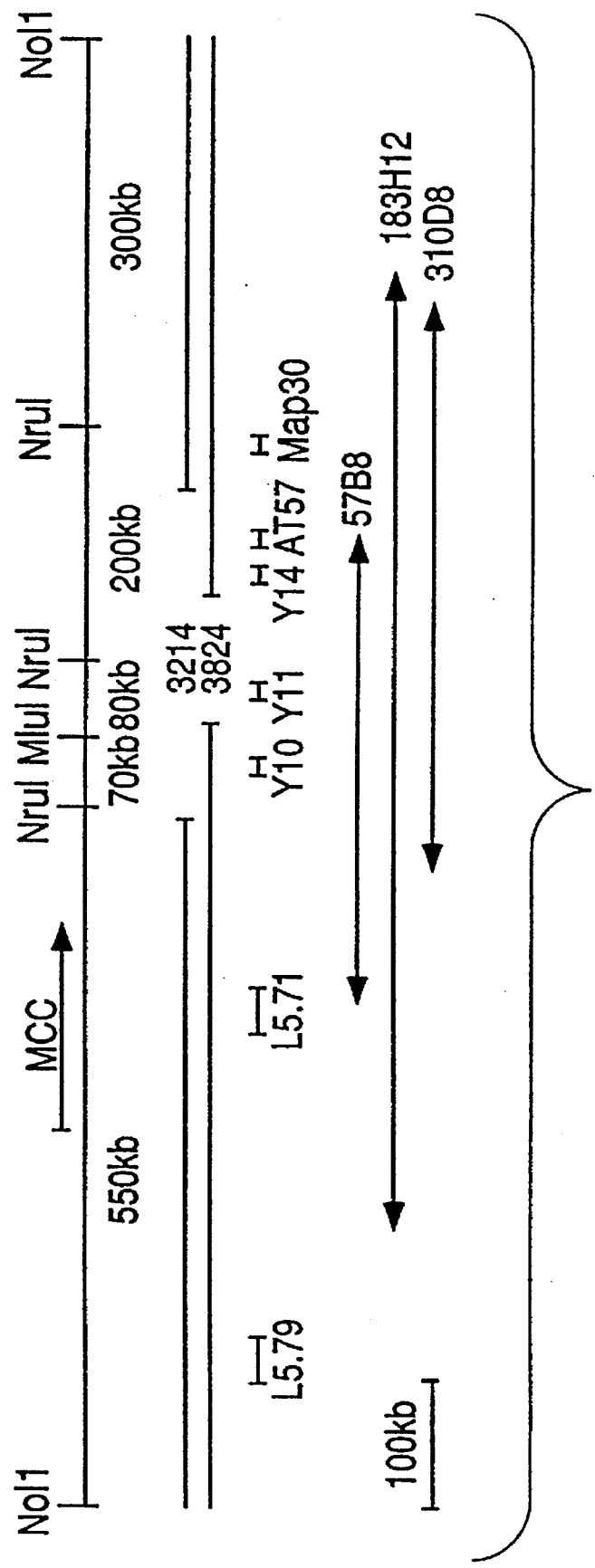

FIG. 5 shows the genomic map of the 1200 kb NotI fragment at the FAP locus. The NotI fragment is shown as a bold line. Relevant parts of the deletion chromosomes from patients 3214 and 3824 are shown as stippled lines. Probes used to characterize the NotI fragment and the deletions, and three YACs from which subclones were obtained, are shown below the restriction map. The chimeric end of YAC 183H12 is indicated by a dotted line. The orientation and approximate position of MCC are indicated above the map.

FIG. 6 shows the DNA sequence (SEQ ID NO: 3) and predicted amino acid sequence of DP1 (TB2) (SEQ ID NO: 4). The nucleotide numbering begins at the most 5' nucleotide isolated. A proposed initiation methionine (base 77) is indicated in bold type. The entire coding sequence is presented.

FIG. 7 shows the cDNA (SEQ ID NO: 1) and predicted amino acid sequence of DP2.5 (APC) (SEQ ID NO: 2). The nucleotide numbering begins at the proposed initiation methionine. The nucleotides and amino acids of the alternatively spliced exon (exon 9; nucleotide positions 934–1236) are presented in lower case letters. At the 3' end, a poly(A) addition signal occurs at 9530, and one cDNA clone has a poly(A) at 9563. Other cDNA clones extend beyond 9563, however, and their consensus sequence is included here.

Figure 8A:
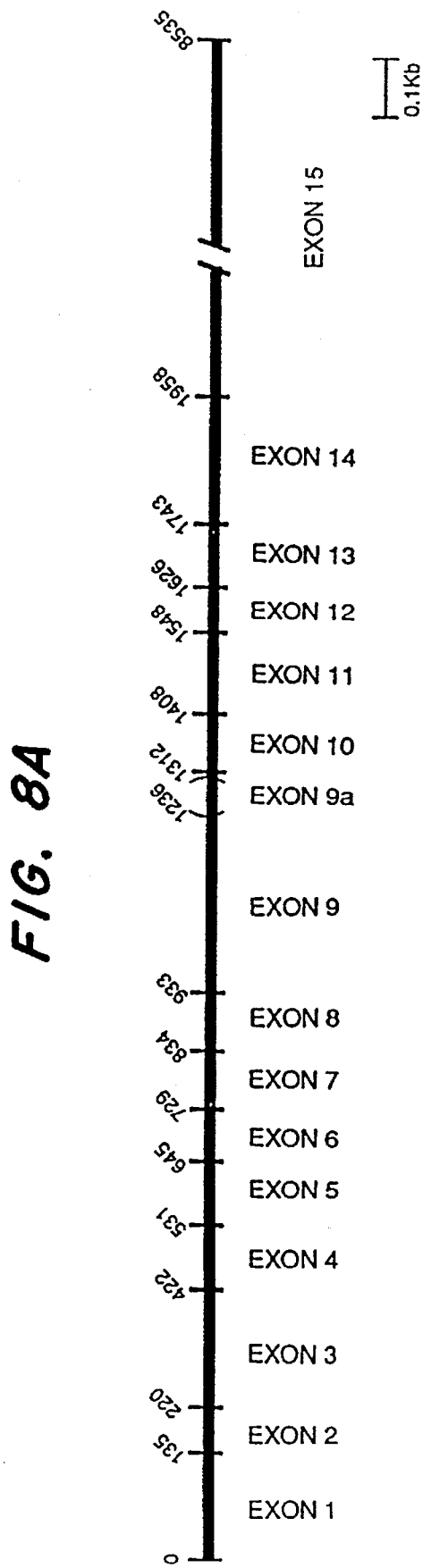
Figures 2, 8B:
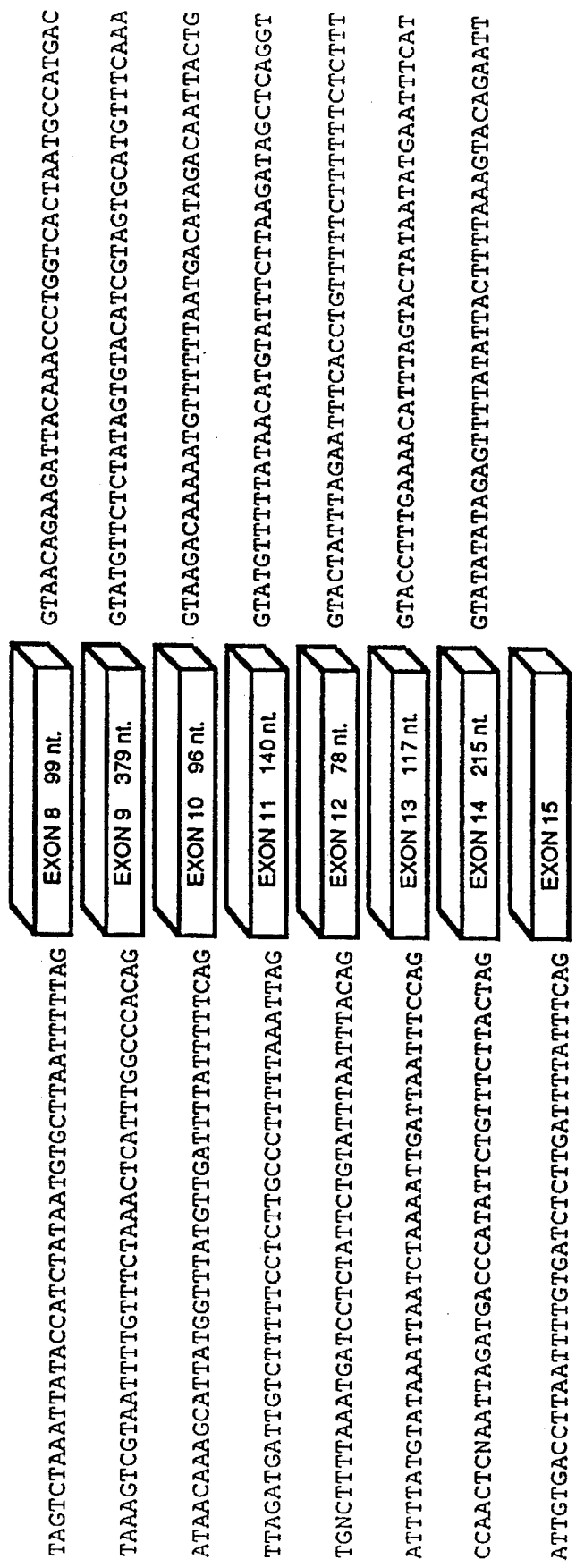
FIGS. 2A and 2B shows the sequence of TB1 (SEQ ID NO: 5) and TB2 (SEQ ID NO: 6) genes. The cDNA sequence of the TB1 gene was determined from the analysis of 11 cDNA clones derived from normal colon and liver, as described in the text. A total of 2314 bp were contained within the overlapping cDNA clones, defining an ORF of 424 amino acids beginning at nucleotide 1. Only the predicted amino acids from the ORF are shown. The carboxy-terminal end of the ORF has apparently been identified, but the 5' end of the TB1 transcript has not yet been precisely determined.

FIGS. 8A and 8B shows the arrangement of exons in DP2.5 (APC). (A) Exon 9 corresponds to nucleotides 933–1312; exon 9a corresponds to nucleotides 1236–1312. The stop codon in the cDNA is at nucleotide 8535. (B) Partial intronic sequence surrounding each exon is shown (SEQ ID NO: 11–38). 5' intron sequences of exons 2, 3, 4, 5, 6, 7, 8, 9, 10, 11, 12, 13, 14, and 15 are shown in SEQ ID NOS: 12, 14, 16, 18, 20, 22, 24, 26, 28, 30, 32, 34, 36, 38, respectively. 3' intron sequences of exons 1, 2, 3, 4, 5, 6, 7, 8, 9, 10, 11, 12, 13, and 14 are shown in SEQ ID NOS: 11, 13, 15, 17, 19, 21, 23, 25, 27, 29, 31, 33, 35, 37, respectively.

DETAILED DESCRIPTION

It is a discovery of the present invention that mutational events associated with tumorigenesis occur in a previously unknown gene on chromosome 5q named here the APC (*Adenomatous Polyposis Coli*) gene. Although it was previously known that deletion of alleles on chromosome 5q were common in certain types of cancers, it was not known that a target gene of these deletions was the APC gene. Further it was not known that other types of mutational events in the APC gene are also associated with cancers. The mutations of the APC gene can involve gross rearrangements, such as insertions and deletions. Point mutations have also been observed.

According to the diagnostic and prognostic method of the present invention, alteration of the wild-type APC gene is detected. "Alteration of a wild-type gene" according to the present invention encompasses all forms of mutations—including deletions. The alteration may be due to either rearrangements such as insertions, inversions, and deletions, or to point mutations. Deletions may be of the entire gene or only a portion of the gene. Somatic mutations are those which occur only in certain tissues, e.g., in the tumor tissue, and are not inherited in the germline. Germline mutations can be found in any of a body's tissues. If only a single allele is somatically mutated, an early neoplastic state is indicated. However, if both alleles are mutated then a late neoplastic state is indicated. The finding of APC mutations thus provides both diagnostic and prognostic information. An APC allele which is not deleted (e.g., that on the sister chromosome to a chromosome carrying an APC deletion) can be screened for other mutations, such as insertions, small deletions, and point mutations. It is believed that many mutations found in tumor tissues will be those leading to decreased expression of the APC gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the APC gene product.

In order to detect the alteration of the wild-type APC gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. If the tumor tissue is highly contaminated with normal cells, detection of mutations is more difficult.

Detection of point mutations may be accomplished by molecular cloning of the APC allele (or alleles) and sequencing that allele(s) using techniques well known in the art. Alternatively, the polymerase chain reaction (PCR) can be used to amplify gene sequences directly from a genomic DNA preparation from the tumor tissue. The DNA sequence of the amplified sequences can then be determined. The polymerase chain reaction itself is well known in the art. See, e.g., Saiki et al., Science, Vol. 239, p. 487, 1988; U.S. Pat. Nos. 4,683,203; and 4,683,195. Specific primers which can be used in order to amplify the gene will be discussed in more detail below. The ligase chain reaction, which is known in the art, can also be used to amplify APC sequences. See Wu et al., *Genomics*, Vol. 4, pp. 560–569 (1989). In addition, a technique known as allele specific PCR can be used. (See Ruano and Kidd, Nucleic Acids Research, Vol. 17, p. 8392, 1989.) According to this technique, primers are used which hybridize at their 3' ends to a particular APC mutation. If the particular APC mutation is not present, an amplification product is not observed. Amplification Refractory Mutation System (ARMS) can also be used as disclosed in European Patent Application Publication No. 0332435 and in Newton et al., Nucleic Acids Research, Vol. 17, p.7, 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening among kindred persons of an affected individual for the presence of the APC mutation found in that individual. Single stranded conformation polymorphism (SSCP) analysis can also be used to detect base change variants of an allele. (Orita et al., Proc. Natl. Acad. Sci. USA Vol. 86, pp. 2766–2770, 1989, and Genomics, Vol. 5, pp. 874–879, 1989.) Other techniques for detecting insertions and deletions as are known in the art can be used.

Alteration of wild-type genes can also be detected on the basis of the alteration of a wild-type expression product of the gene. Such expression products include both the APC mRNA as well as the APC protein product. The sequences of these products are shown in FIGS. 3 and 7. Point mutations may be detected by amplifying and sequencing the mRNA or via molecular cloning of cDNA made from the mRNA. The sequence of the cloned cDNA can be determined using DNA sequencing techniques which are well known in the art. The cDNA can also be sequenced via the polymerase chain reaction (PCR) which will be discussed in more detail below.

Mismatches, according to the present invention are hybridized nucleic acid duplexes which are not 100% homologous. The lack of total homology may be due to deletions, insertions, inversions, substitutions or frameshift mutations. Mismatch detection can be used to detect point mutations in the gene or its mRNA product. While these techniques are less sensitive than sequencing, they are simpler to perform on a large number of tumor samples. An example of a mismatch cleavage technique is the RNase protection method, which is described in detail in Winter et al., Proc. Natl. Acad. Sci. USA, Vol. 82, p. 7575, 1985 and Meyers et al., Science, Vol. 230, p. 1242, 1985. In the practice of the present invention the method involves the use of a labeled riboprobe which is complementary to the human wild-type APC gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the APC mRNA or gene but can be a segment of either. If the riboprobe comprises only a segment of the APC mRNA or gene it will be desirable to use a number of these probes to screen the whole mRNA sequence for mismatches.

In similar fashion, DNA probes can be used to detect mismatches, through enzymatic or chemical cleavage. See, e.g., Cotton et al., Proc. Natl. Acad. Sci. USA, Vol. 85, 4397, 1988; and Shenk et al., Proc. Natl. Acad. Sci. USA, Vol. 72, p. 989, 1975. Alternatively, mismatches can be detected by shifts in the electrophoretic mobility of mismatched duplexes relative to matched duplexes. See, e.g., Cariello, Human Genetics, Vol. 42, p. 726, 1988. With either riboprobes or DNA probes, the cellular mRNA or DNA which might contain a mutation can be amplified using PCR (see below) before hybridization. Changes in DNA of the APC gene can also be detected using Southern hybridization, especially if the changes are gross rearrangements, such as deletions and insertions.

DNA sequences of the APC gene which have been amplified by use of polymerase chain reaction may also be screened using allele-specific probes. These probes are nucleic acid oligomers, each of which contains a region of the APC gene sequence harboring a known mutation. For example, one oligomer may be about 30 nucleotides in length, corresponding to a portion of the APC gene sequence. By use of a battery of such allele-specific probes, PCR amplification products can be screened to identify the presence of a previously identified mutation in the APC gene. Hybridization of allele-specific probes with amplified APC sequences can be performed, for example, on a nylon filter. Hybridization to a particular probe under stringent hybridization conditions indicates the presence of the same mutation in the tumor tissue as in the allele-specific probe.

Alteration of APC mRNA expression can be detected by any technique known in the art. These include Northern blot analysis, PCR amplification and RNase protection. Diminished mRNA expression indicates an alteration of the wild-type APC gene.

Alteration of wild-type APC genes can also be detected by screening for alteration of wild-type APC protein. For example, monoclonal antibodies immunoreactive with APC can be used to screen a tissue. Lack of cognate antigen would indicate an APC mutation. Antibodies specific for products of mutant alleles could also be used to detect mutant APC gene product. Such immunological assays can be done in any convenient format known in the art. These include Western blots, immunohistochemical assays and ELISA assays. Any means for detecting an altered APC protein can be used to detect alteration of wild-type APC genes. Functional assays can be used, such as protein binding determinations. For example, it is believed that APC protein oligomerizes to itself and/or MCC protein or binds to a G protein. Thus, an assay for the ability to bind to wild type APC or MCC protein or that G protein can be employed. In addition, assays can be used which detect APC biochemical function. It is believed that APC is involved in phospholipid metabolism. Thus, assaying the enzymatic products of the involved phospholipid metabolic pathway can be used to determine APC activity. Finding a mutant APC gene product indicates alteration of a wild-type APC gene.

Mutant APC genes or gene products can also be detected in other human body samples, such as, serum, stool, urine and sputum. The same techniques discussed above for detection of mutant APC genes or gene products in tissues can be applied to other body samples. Cancer cells are sloughed off from tumors and appear in such body samples. In addition, the APC gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant APC genes or gene products.

The methods of diagnosis of the present invention are applicable to any tumor in which APC has a role in tumorigenesis. Deletions of chromosome arm 5q have been observed in tumors of lung, breast, colon, rectum, bladder, liver, sarcomas, stomach and prostate, as well as in leukemias and lymphomas. Thus these are likely to be tumors in which APC has a role. The diagnostic method of the present invention is useful for clinicians so that they can decide upon an appropriate course of treatment. For example, a tumor displaying alteration of both APC alleles might suggest a more aggressive therapeutic regimen than a tumor displaying alteration of only one APC allele.

The primer pairs of the present invention are useful for determination of the nucleotide sequence of a particular APC allele using the polymerase chain reaction. The pairs of single stranded DNA primers can be annealed to sequences within or surrounding the APC gene on chromosome 5q in order to prime amplifying DNA synthesis of the APC gene itself. A complete set of these primers allows synthesis of all of the nucleotides of the APC gene coding sequences, i.e., the exons. The set of primers preferably allows synthesis of both intron and exon sequences. Allele specific primers can also be used. Such primers anneal only to particular APC mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from APC sequences or sequences adjacent to APC except the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of the APC open reading frame shown in FIG. 7 (SEQ ID NO: 1), design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the APC gene or mRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids. These techniques are known in the art. See, Cotton, supra, Shenk, supra, Myers, supra, Winter, supra, and Novack et al., Proc. Natl. Acad. Sci. USA, Vol. 83, p. 586, 1986. Generally, the probes are complementary to APC gene coding sequences, although probes to certain introns are also contemplated. An entire battery of nucleic acid probes is used to compose a kit for detecting alteration of wild-type APC genes. The kit allows for hybridization to the entire APC gene. The probes may overlap with each other or be contiguous.

If a riboprobe is used to detect mismatches with mRNA, it is complementary to the mRNA of the human wild-type APC gene. The riboprobe thus is an anti-sense probe in that it does not code for the APC protein because it is of the opposite polarity to the sense strand. The riboprobe generally will be labeled with a radioactive, colorimetric, or fluorometric material, which can be accomplished by any means known in the art. If the riboprobe is used to detect mismatches with DNA it can be of either polarity, sense or anti-sense. Similarly, DNA probes also may be used to detect mismatches.

Nucleic acid probes may also be complementary to mutant alleles of the APC gene. These are useful to detect similar mutations in other patients on the basis of hybridization rather than mismatches. These are discussed above and referred to as allele-specific probes. As mentioned above, the APC probes can also be used in Southern hybridizations to genomic DNA to detect gross chromosomal changes such as deletions and insertions. The probes can also be used to select cDNA clones of APC genes from tumor and normal tissues. In addition, the probes can be used to detect APC mRNA in tissues to determine if expression is diminished as a result of alteration of wild-type APC genes. Provided with the APC coding sequence shown in FIG. 7 (SEQ ID NO: 1), design of particular probes is well within the skill of the ordinary artisan.

According to the present invention a method is also provided of supplying wild-type APC function to a cell which carries mutant APC alleles. Supplying such function should suppress neoplastic growth of the recipient cells. The wild-type APC gene or a part of the gene may be introduced into the cell in a vector such that the gene remains extrachromosomal. In such a situation the gene will be expressed by the cell from the extrachromosomal location. If a gene portion is introduced and expressed in a cell carrying a mutant APC allele, the gene portion should encode a part of the APC protein which is required for non-neoplastic growth of the cell. More preferred is the situation where the wild-type APC gene or a part of it is introduced into the mutant cell in such a way that it recombines with the endogenous mutant APC gene present in the cell. Such recombination requires a double recombination event which results in the correction of the APC gene mutation. Vectors for introduction of genes both for recombination and for extrachromosomal maintenance are known in the art and any suitable vector may be used. Methods for introducing DNA into cells such as electroporation, calcium phosphate co-precipitation and viral transduction are known in the art and the choice of method is within the competence of the routineer. Cells transformed with the wild-type APC gene can be used as model systems to study cancer remission and drug treatments which promote such remission.

Similarly, cells and animals which carry a mutant APC allele can be used as model systems to study and test for substances which have potential as therapeutic agents. The cells are typically cultured epithelial cells. These may be isolated from individuals with APC mutations, either somatic or germline. Alternatively, the cell line can be engineered to carry the mutation in the APC allele. After a test substance is applied to the cells, the neoplastically transformed pheno-type of the cell will be determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant APC alleles, usually from a second animal species, as well as insertion of disrupted homologous genes. Alternatively, the endogenous APC gene(s) of the animals may be disrupted by insertion or deletion mutation. After test substances have been administered to the animals, the growth of tumors must be assessed. If the test substance prevents or suppresses the growth of tumors, then the test substance is a candidate therapeutic agent for the treatment of FAP and/or sporadic cancers.

Polypeptides which have APC activity can be supplied to cells which carry mutant or missing APC alleles. The sequence of the APC protein is disclosed in FIG. 3 or 7 (SEQ ID NO: 2). These two sequences differ slightly and appear to be indicate the existence of two different forms of the APC protein. Protein can be produced by expression of the cDNA sequence in bacteria, for example, using known expression vectors. Alternatively, APC can be extracted from APC-producing mammalian cells such as brain cells. In addition, the techniques of synthetic chemistry can be employed to synthesize APC protein. Any of such techniques can provide the preparation of the present invention which comprises the APC protein. The preparation is substantially free of other human proteins. This is most readily accomplished by synthesis in a microorganism or in vitro.

Active APC molecules can be introduced into cells by microinjection or by use of liposomes, for example. Alternatively, some such active molecules may be taken up by cells, actively or by diffusion. Extracellular application of APC gene product may be sufficient to affect tumor growth. Supply of molecules with APC activity should lead to a partial reversal of the neoplastic state. Other molecules with APC activity may also be used to effect such a reversal, for example peptides, drugs, or organic compounds.

The present invention also provides a preparation of antibodies immunoreactive with a human APC protein. The antibodies may be polyclonal or monoclonal and may be raised against native APC protein, APC fusion proteins, or mutant APC proteins. The antibodies should be immunoreactive with APC epitopes, preferably epitopes not present on other human proteins. In a preferred embodiment of the invention the antibodies will immunoprecipitate APC proteins from solution as well as react with APC protein on Western or immunoblots of polyacrylamide gels. In another preferred embodiment, the antibodies will detect APC proteins in paraffin or frozen tissue sections, using immunocytochemical techniques. Techniques for raising and purifying antibodies are well known in the art and any such techniques may be chosen to achieve the preparation of the invention.

Predisposition to cancers as in FAP and GS can be ascertained by testing any tissue of a human for mutations of the APC gene. For example, a person who has inherited a germline APC mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells, or amniotic fluid for mutations of the APC gene. Alteration of a wild-type APC allele, whether for example, by point mutation or by deletion, can be detected by any of the means discussed above.

Molecules of cDNA according to the present invention are intron-free, APC gene coding molecules. They can be made by reverse transcriptase using the APC mRNA-as a template. These molecules can be propagated in vectors and cell lines as is known in the art. Such molecules have the sequence shown in SEQ ID NO: 7. The cDNA can also be made using the techniques of synthetic chemistry given the sequence disclosed herein.

A short region of homology has been identified between APC and the human m3 muscarinic acetylcholine receptor (mAChR). This homology was largely confined to 29 residues in which 6 out of 7 amino acids (EL(GorA)GLQA) were identical (See FIG. 4 (SEQ ID NO: 9)). Initially, it was not known whether this homology was significant, because many other proteins had higher levels of global homology (though few had six out of seven contiguous amino acids in common). However, a study on the sequence elements controlling G protein activation by mAChR subtypes (Lechleiter et al., EMBO J., p. 4381 (1990)) has shown that a 21 amino acid region from the m3 mAChR completely mediated G protein specificity when substituted for the 21 amino acids of m2 mAChR at the analogous protein position. These 21 residues overlap the 19 amino acid homology between APC and m3 mAChR.

This connection between APC and the G protein activating region of mAChR is intriguing in light of previous investigations relating G proteins to cancer. For example, the RAS oncogenes, which are often mutated in colorectal cancers (Vogelstein, et al., N. Engl. J. Med., Vol. 319, p. 525 (1988); Bos et al., Nature Vol. 327, p. 293 (1987)), are members of the G protein family (Bourne, et al., Nature, Vol. 348, p. 125 (1990)) as is an in vitro transformation suppressor (Noda et al., Proc. Natl. Acad. Sci. USA, Vol. 86, p. 162 (1989)) and genes mutated in hormone producing tumors (Candis et al., Nature, Vol. 340, p. 692 (1989); Lyons et al., Science, Vol. 249, p. 655 (1990)). Additionally, the gene responsible for neurofibromatosis (presumably a tumor suppressor gene) has been shown to activate the GTPase activity of RAS (Xu et al., Cell, Vol. 63, p. 835 (1990); Martin et al., Cell, Vol. 63, p. 843 (1990); Ballester et al., Cell, Vol. 63, p. 851 (1990)). Another interesting link between G proteins and colon cancer involves the drug sulindac. This agent has been shown to inhibit the growth of benign colon tumors in patients with FAP, presumably by virtue of its activity as a cyclooxygenase inhibitor (Waddell et al., J. Surg. Oncology 24(1), 83 (1983); Wadell, et al., Am. J. Surg., 157(1), 175 (1989); Charneau et al., Gastroenterologie Clinique at Biologique 14(2), 153 (1990)). Cyclooxygenase is required to convert arachidonic acid to prostaglandins and other biologically active molecules. G proteins are known to regulate phospholipase A2 activity, which generates arachidonic acid from phospholipids (Role et al., Proc. Natl. Acad. Sci. USA, Vol. 84, p. 3623 (1987); Kurachi et al., Nature, Vol. 337, 12 555 (1989)). Therefore we propose that wild-type APC protein functions by interacting with a G protein and is involved in phospholipid metabolism.

The following are provided for exemplification purposes only and are not intended to limit the scope of the invention which has been described in broad terms above.

EXAMPLE 1

This example demonstrates the isolation of a 5.5 Mb region of human DNA linked to the FAP locus. Six genes are identified in this region, all of which are expressed in normal colon cells and in colorectal, lung, and bladder tumors.

The cosmid markers YN5.64 and YN5.48 have previously been shown to delimit an 8 cM region containing the locus for FAP (Nakamura et al., Am. J. Hum. Genet. Vol. 43, p. 638 (1988)). Further linkage and pulse-field gel electrophoresis (PFGE) analysis with additional markers has shown that the FAP locus is contained within a 4 cM region bordered by cosmids EF5.44 and L5.99. In order to isolate clones representing a significant portion of this locus, a yeast artificial chromosome (YAC) library was screened with various 5q21 markers. Twenty-one YAC clones, distributed within six contigs and including 5.5 Mb from the region between YN5.64 and YN5.48, were obtained (FIG. 1A).

Three contigs encompassing approximately 4 Mb were contained within the central portion of this region. The YAC's constituting these contigs, together with the markers used for their isolation and orientations, are shown In FIG. 1. These YAC contigs were obtained in the following way. To initiate each contig, the sequence of a genomic marker cloned from chromosome 5q21 was determined and used to design primers for PCR. PCR was then carried out on pools of YAC clones distributed in microtiter trays as previously described (Anand et al., Nucleic Acids Research, Vol. 18, p. 1951 (1980)). Individual YAC clones from the positive pools were identified by further PCR or hybridization based assays, and the YAC sizes were determined by PFGE.

To extend the areas covered by the original YAC clones, "chromosomal walking" was performed. For this purpose, YAC termini were isolated by a PCR based method and sequenced (Riley et al., Nucleic Acids Research, Vol. 18, p. 2887 (1990)). PCR primers based on these sequences were then used to rescreen the YAC library. For example, the sequence from an intron of the FER gene (Hao et al., Mol. Cell. Biol., Vol. 9, p. 1587 (1989)) was used to design PCR primers for isolation of the 28EC1 and 5EH8 YACs. The termini of the 28EC1 YAC were sequenced to derive markers RHE28 and LHE28, respectively. The sequences of these two markers were then used to isolate YAC clones 15CH12 (from RHE28) and 40CF1 and 29EF1 (from LHE28). These five YAC's formed a contig encompassing 1200 kb (contig 1, FIG. 1B).

Similarly, contig 2 was initiated using cosmid N5.66 sequences, and contig 3 was initiated using sequences both from the MCC gene and from cosmid EF5.44. A walk in the telomeric direction from YAC 14FH1 and a walk in the opposite direction from YAC 39GG3 allowed connection of the initial contig 3 clones through YAC 37HG4 (FIG. 1B). YAC37HG4 was deposited at the National Collection of Industrial and Marine Bacteria (NCIMB), P.O. Box 31, 23 St. Machar Drive, Aberdeen AB2 1RY, Scotland, under Acession No. 40353 on Dec. 17, 1990.

Multipoint linkage analysis with the various markers used to define the contigs, combined with PFGE analysis, showed that contigs 1 and 2 were centromeric to contig 3. These contigs were used as tools to orient and/or identify genes which might be responsible for FAP. Six genes were found to lie within this cluster of YAC's, as follows:

Contig #1: FER—The FER gene was discovered through its homology to the viral oncogene ABL (Hao et al., supra).

It has an intrinsic tyrosine kinase activity, and in situ hybridization with an FER probe showed that the gene was located at 5q11-23 (Morris et al., Cytogenet. Cell. Genet., Vol. 53, p. 4, (1990)). Because of the potential role of this oncogene-related gene in neoplasia, we decided to evaluate it further with regards to the FAP locus. A human genomic clone from FER was isolated (MF 2.3) and used to define a restriction fragment length polymorphism (RFLP), and the RFLP in turn used to map FER by linkage analysis using a panel of three generation families. This showed that FER was very tightly linked to previously defined polymorphic markers for the FAP locus. The genetic mapping of FER was complemented by physical mapping using the YAC clones derived from FER sequences (FIG. 1B). Analysis of YAC contig 1 showed that FER was within 600 kb of cosmid marker M5.28, which maps to within 1.5 Mb of cosmid L5.99 by PFGE of human genomic DNA. Thus, the YAC mapping results were consistent with the FER linkage data and PFGE analyses.

Contig 2:TB1—TB1 was identified through a cross-hybridization approach. Exons of genes are often evolutionarily conserved while introns and intergenic regions are much less conserved. Thus, if a human probe cross-hybridizes strongly to the DNA from non-primate species, there is a reasonable chance that it contains exon sequences. Subclones of the cosmids shown in FIG. 1 were used to screen Southern blots containing rodent DNA samples. A subclone of cosmid N5.66 (p 5.66-4) was shown to strongly hybridize to rodent DNA, and this clone was used to screen cDNA libraries derived from normal adult colon and fetal liver. The ends of the initial cDNA clones obtained in this screen were then used to extend the cDNA sequence. Eventually, 11 cDNA clones were isolated, covering 2314 bp. The gene detected by these clones was named TB1. Sequence analysis of the overlapping clones revealed an open reading frame (ORF) that extended for 1302 bp starting from the most 5' sequence data obtained (FIG. 2A). If this entire open reading frame were translated, it would encode 434 amino acids (SEQ ID NO: 5). The product of this gene was not globally homologous to any other sequence in the current database but showed two significant local similarities to a family of ADP, ATP carrier/translocator proteins and mitochondrial brown fat uncoupling proteins which are widely distributed from yeast to mammals. These conserved regions of TB1 (underlined in FIG. 2A) may define a predictive motif for this sequence family. In addition, TB1 appeared to contain a signal peptide (or mitochondrial targeting sequence) as well as at least 7 transmembrane domains.

Contig 3: MCC, TB2, SRP and APC—The MCC gene was also discovered through a cross-hybridization approach, as described previously (Kinzler et al., Science Vol. 251, p. 1366 (1991)). The MCC gene was considered a candidate for causing FAP by virtue of its tight genetic linkage to FAP susceptibility and its somatic mutation in sporadic colorectal carcinomas. However, mapping experiments suggested that the coding region of MCC was approximately 50 kb proximal to the centromeric end of a 200 kb deletion found in an FAP patient. MCC cDNA probes detected a 10 kb mRNA transcript on Northern blot analysis of which 4151 bp, including the entire open reading frame, have been cloned. Although the 3' non-translated portion or an alternatively spliced form of MCC might have extended into this deletion, it was possible that the deletion did not affect the MCC gene product. We therefore used MCC sequences to initiate a YAC contig, and subsequently used the YAC clones to identify genes 50 to 250 kb distal to MCC that might be contained within the deletion.

In a first approach, the insert from YAC24ED6 (FIG. 1B) was radiolabelled and hybridized to a cDNA library from normal colon. One of the cDNA clones (YS39) identified in this manner detected a 3.1 kb mRNA transcript when used as a probe for Northern blot hybridization. Sequence analysis of the YS39 clone revealed that it encompassed 2283 nucleotides and contained an ORF that extended for 555 bp from the most 5' sequence data obtained. If all of this ORF were translated, it would encode 185 amino acids (SEQ ID NO: 6) (FIG. 2B). The gene detected by YS39 was named TB2. Searches of nucleotide and protein databases revealed that the TB2 gene was not identical to any previously reported sequences nor were there any striking similarities.

Another clone (YS11) identified through the YAC 24ED6 screen appeared to contain portions of two distinct genes. Sequences from one end of YS11 were identical to at least 180 bp of the signal recognition particle protein SRP19 (Lingelbach et al. Nucleic Acids Research, Vol. 16, p. 9431 (1988). A second ORF, from the opposite end of clone YS11, proved to be identical to 78 bp of a novel gene which was independently identified through a second YAC-based approach. For the latter, DNA from yeast cells containing YAC 14FH1 (FIG. 1B) was digested with EcoRI and subcloned into a plasmid vector. Plasmids that contained human DNA fragments were selected by colony hybridization using total human DNA as a probe. These clones were then used to search for cross-hybridizing sequences as described above for TB1, and the cross-hybridizing clones were subsequently used to screen cDNA libraries. One of the cDNA clones discovered in this way (FH38) contained a long ORF (2496 bp), 78 bp of which were identical to the above-noted sequences in YS11. The ends of the FH38 cDNA clone were then used to initiate cDNA walking to extend the sequence. Eventually, 85 cDNA clones were isolated from normal colon, brain and liver cDNA libraries and found to encompass 8973 nucleotides of contiguous transcript. The gene corresponding to this transcript was named APC. When used as probes for Northern blot analysis, APC cDNA clones hybridized to a single transcript of approximately 9.5 kb, suggesting that the great majority of the gene product was represented in the cDNA clones obtained. Sequences from the 5' end of the APC gene were found in YAC 37HG4 but not in YAC 14FH1. However, the 3' end of the APC gene was found in 14FH1 as well as 37HG4. Analogously, the 5' end of the MCC coding region was found in YAC clones 19AA9 and 26GC3 but not 24ED6 or 14FH1, while the 3' end displayed the opposite pattern. Thus, MCC and APC transcription units pointed in opposite directions, with the direction of transcription going from centromeric to telomeric in the case of MCC, and telomeric to centromeric in the case of APC. PFGE analysis of YAC DNA digested with various restriction endonucleases showed that TB2 and SRP were between MCC and APC, and that the 3' ends of the coding regions of MCC and APC were separated by approximately 150 kb (FIG. 1B).

Sequence analysis of the APC cDNA clones revealed an open reading frame of 8,535 nucleotides. The 5' end of the ORF contained a methionine codon (codon 1) that was preceded by an in-frame stop codon 9 bp upstream, and the 3' end was followed by several in-frame stop codons. The protein produced by initiation at codon 1 would contain 2,842 amino acids (SEQ ID NO: 2) (FIG. 3). The results of database searching with the APC gene product were quite complex due to the presence of large segments with locally biased amino acid compositions. In spite of this, APC could be roughly divided into two domains. The N-terminal 25% of the protein had a high content of leucine residues (12%)

and showed local sequence similarities to myosins, various intermediate filament proteins (e.g., desmin, vimentin, neurofilaments) and Drosophila armadillo/human plakoglobin. The latter protein is a component of adhesive junctions (desmosomes) joining epithelial cells (Franke et al., Proc. Natl. Acad. Sci. U.S.A., Vol. 86, p. 4027 (1989); Perfer et al., Cell, Vol. 63, p. 1167 (1990)) The C-terminal 75% of APC (residues 731–2832) is 17% serine by composition with serine residues more or less uniformly distributed. This large domain also contains local concentrations of charged (mostly acidic) and proline residues. There was no indication of potential signal peptides, transmembrane regions, or nuclear targeting signals in APC, suggesting a cytoplasmic localization.

To detect short similarities to APC, a database search was performed using the PAM-40 matrix (Altschul. J. Mol. Bio., Vol. 219, p. 555 (1991). Potentially interesting matches to several proteins were found. The most suggestive of these involved the ral2 gene product of yeast, which is implicated in the regulation of ras activity (Fukui et al., Mol. Cell. Biol., Vol. 9, p. 5617 (1989)). Little is known about how ral2 might interact with ras but it is interesting to note the positively-charged character of this region in the context of the negatively-charged GAP interaction region of ras. A specific electrostatic interaction between ras and GAP-related proteins has been proposed.

Because of the proximity of the MCC and APC genes, and the fact that both are implicated in colorectal tumorigenesis, we searched for similarities between the two predicted proteins. Bourne has previously noted that MCC has the potential to form alpha helical coiled coils (Nature, Vol. 351, p. 188 (1991). Lupas and colleagues have recently developed a program for predicting coiled coil potential from primary sequence data (Science, Vol. 252, p. 1162 (1991) and we have used their program to analyze both MCC and APC. Analysis of MCC indicated a discontinuous pattern of coiled-coil domains separated by putative "hinge" or "spacer" regions similar to those seen in laminin and other intermediate filament proteins. Analysis of the APC sequence revealed two regions in the N-terminal domain which had strong coiled coil-forming potential, and these regions corresponded to those that showed local similarities with myosin and IF proteins on database searching. In addition, one other putative coiled coil region was identified in the central region of APC. The potential for both APC and MCC to form coiled coils is interesting in that such structures often mediate homo- and hetero-oligomerization.

Finally, it had previously been noted that MCC shared a short similarity with the region of the m8 muscarinic acetylcholine receptor (mAChR) known to regulate specificity of G-protein coupling. The APC gene also contained a local similarity to the region of the m3 mAChR (SEQ ID NO: 9) that overlapped with the MCC similarity (SEQ ID NO: 10(FIG. 4B). Although the similarities to ral2 (SEQ ID NO: 8) (FIG. 4A) and m3 mAChR (SEQ ID NO: 9) (FIG. 4B) were not statistically significant, they were intriguing in light of previous observations relating G-proteins to neoplasia.

Each of the six genes described above was expressed in normal colon mucosa, as indicated by their representation in colon cDNA libraries. To study expression of the genes in neoplastic colorectal epithelium, we employed reverse transcription-polymerase chain reaction (PCR) assays. Primers based on the sequences of FER, TB1, TB2, MCC, and APC were each used to design primers for PCR performed with cDNA templates. Each of these genes was found to be expressed in normal colon, in each of ten cell lines derived from colorectal cancers, and in tumor cell lines derived from lung and bladder tumors. The ten colorectal cancer cell lines included eight from patients with sporadic CRC and two from patients with FAP.

EXAMPLE 2

This example demonstrates a genetic analysis of the role of the FER gene in FAP and sporadic colorectal cancers.

We considered FER as a candidate because of its proximity to the FAP locus as judged by physical and genetic criteria (see Example 1), and its homology to known tyrosine kinases with oncogenic potential. Primers were designed to PCR-amplify the complete coding sequence of FER from the RNA of two colorectal cancer cell lines derived from FAP patients. cDNA was generated from RNA and used as a template for PCR. The primers used were 5'-AGAAGGATCCCTTGTGCAGTGTGGA-3' (SEQ ID NO: 95) and 5'-GACAGGATCCTGAAGCTGAGTTTG-3' (SEQ ID NO: 96). The underlined nucleotides were altered from the true FER sequence to create BamHI sites. The cell lines used were JW and Difi, both derived from colorectal cancers of FAP patients. (C. Paraskeva, B. G. Buckle, D. Sheer, C. B. Wigley, Int. J. Cancer 34, 49 (1984); M. E. Gross et al., Cancer Res. 51, 1452 (1991). The resultant 2554 basepair fragments were cloned and sequenced in their entirety. The PCR products were cloned in the BamHI site of Bluescript SK (Stratagene) and pools of at least 50 clones were sequenced en masse using T7 polymerase, as described in Nigro et al., Nature 342, 705 (1989).

Only a single conservative amino acid change (GTG->CTG, creating a val to leu substitution at codon 439) was observed. The region surrounding this codon was then amplified from the DNA of individuals without FAP and this substitution was found to be a common polymorphism, not specifically associated with FAP. Based on these results, we considered it unlikely (though still possible) the FER gene was responsible for FAP. To amplify the regions surrounding codon 439, the following primers were used: 5'-TCAGAAAGTGCTGAAGAG-3' (SEQ ID NO: 97) and 5'-GGAATAATTAGGTCTCCAA-3' (SEQ ID NO: 98). PCR products were digested with PstI, which yields a 50 bp fragment if codon 439 is leucine, but 26 and 24 bp fragments if it is valine. The primers used for sequencing were chosen from the FER cDNA sequence in Hao et al., supra.

EXAMPLE 3

This example demonstrates the genetic analysis of MCC, TB2, SRP and APC in FAP and sporadic colorectal tumors. Each of these genes is linked and encompassed by contig 3 (see FIG. 1).

Several lines of evidence suggested that this contig was of particular interest. First, at least three of the four genes in this contig were within the deleted region identified in two FAP patients. (See Example 5 infra.) Second, allelic deletions of chromosome 5q21 in sporadic cancers appeared to be centered in this region. (Ashton-Rickardt et al., Oncogene, in press; and Miki et al., Japn. J. Cancer Res., in press.) Some tumors exhibited loss of proximal RFLP markers (up to and potentially including the 5' end of MCC), but no loss of markers distal to MCC. Other tumors exhibited loss of markers distal to and perhaps including the 3' end of MCC, but no loss of sequences proximal to MCC. This suggested either that different ends of MCC were affected by loss in all such cases, or alternatively, that two genes (one proximal to and perhaps including MCC, the other distal to MCC) were separate targets of deletion. Third, clones from each of the six FAP region genes were used as probes on Southern blots containing tumor DNA from patients with sporadic CRC. Only two examples of somatic changes were observed in over 200 tumors studied: a rearrangement/ deletion whose centromeric end was located within the MCC gene (Kinzler et al., supra) and an 800 bp insertion within the APC gene between nucleotides 4424 and 5584. Fourth, point mutations of MCC were observed in two tumors (Kinzler et al.) supra strongly suggesting that MCC was a target of mutation in at least some sporadic colorectal cancers.

Based on these results, we attempted to search for subtle alterations of contig 3 genes in patients with FAP. We chose to examine MCC and APC, rather than TB2 or SRP, because of the somatic mutations in MCC and APC noted above. To facilitate the identification of subtle alterations, the genomic sequences of MCC and APC exons were determined (see Table I, SEQ ID NO: 24–38). These sequences were used to design primers for PCR analysis of constitutional DNA from FAP patients.

We first amplified eight exons and surrounding introns of the MCC gene in affected individuals from 90 different FAP kindreds. The PCR products were analyzed by a ribonuclease (RNase) protein assay. In brief, the PCR products were hybridized to in vitro transcribed RNA probes representing the normal genomic sequences. The hybrids were digested with RNase A, which can cleave at single base pair mismatches within DNA-RNA hybrids, and the cleavage products were visualized following denaturing gel electrophoresis. Two separate RNase protection analyses were performed for each exon, one with the sense and one with the antisense strand. Under these conditions, approximately 40% of all mismatches are detectable. Although some amino acid variants of MCC were observed in FAP patients, all such variants were found in a small percentage of normal individuals. These variants were thus unlikely to be responsible for the inheritance of FAP.

We next examined three exons of the APC gene. The three exons examined included those containing nt 822–930, 931–1309, and the first 300 nt of the most distal exon (nt 1956–2256). PCR and RNase protection analysis were performed as described in Kinzler et al. supra, using the primers underlined in Table I (SEQ ID NO: 24–38). The primers for nt 1956–2256 were 5'-GCAAATCCTAAGAGAGAACAA-3' (SEQ ID NO: 99) and 5'-GATGGCAAGCTTGAGCCAG-3' (SEQ ID NO: 100).

In 90 kindreds, the RNase protection method was used to screen for mutations and in an additional 13 kindreds, the PCR products were cloned and sequenced to search for mutations not detectable by RNase protection. PCR products were cloned into a Bluescript vector modified as described in T. A. Holton and M. W. Graham, Nucleic Acids Res. 19, 1156 (1991). A minimum of 100 clones were pooled and sequenced. Five variants were detected among the 103 kindreds analyzed. Cloning and subsequent DNA sequencing of the PCR product of patient P21 indicated a C to T transition in codon 413 that resulted in a change from arginine to cysteine. This amino acid variant was not observed in any of 200 DNA samples from individuals without FAP. Cloning and sequencing of the PCR product from patients P24 and P34, who demonstrated the same abnormal RNase protection pattern indicated that both had a C to T transition at codon 301 that resulted in a change from arginine (CGA) to a stop codon (TGA). This change was not present in 200 individuals without FAP. As this point mutation resulted in the predicted loss of the recognition site for the enzyme Taq I, appropriate PCR products could be digested with Taq I to detect the mutation. This allowed us to determine that the stop codon co-segregated with disease phenotype in members of the family of P24. The inheritance of this change in affected members of the pedigree provides additional evidence for the importance of the mutation.

Cloning and sequencing of the PCR product from FAP patient P93 indicated a C to G transversion at codon 279, also resulting in a stop codon (change from TCA to TGA). This mutation was not present in 200 individuals without FAP. Finally, one additional mutation resulting in a serine (TCA) to stop codon (TGA) at codon 712 was detected in a single patient with FAP (patient P60).

The five germline mutations identified are summarized in Table IIA, as well as four others discussed in Example 9. In addition to these germline mutations, we identified several somatic mutations of MCC and APC in sporadic CRC's. Seventeen MCC exons were examined in 90 sporadic colorectal cancers by RNase protection analysis. In each case where an abnormal RNase protection pattern was observed, the corresponding PCR products were cloned and sequenced. This led to the identification of six point mutations (two described previously) (Kinzler et al., supra), each of which was not found in the germline of these patients (Table IIB). Four of the mutations resulted in amino acid substitutions and two resulted in the alteration of splice site consensus elements. Mutations at analogous splice site positions in other genes have been shown to alter RNA processing in vivo and in vitro.

Three exons of APC were also evaluated in sporadic tumors. Sixty tumors were screened by RNase protection, and an additional 98 tumors were evaluated by sequencing. The exons examined included nt 822–930, 931–1309, and 1406–1545 (Table I). A total of three mutations were identified, each of which proved to be somatic. Tumor T27 contained a somatic mutation of CGA (arginine) to TGA (stop codon) at codon 33. Tumor T135 contained a GT to GC change at a splice donor site. Tumor T34 contained a 5 bp insertion (CAGCC between codons 288 and 289) resulting in a stop at codon 291 due to a frameshift.

We serendipitously discovered one additional somatic mutation in a colorectal cancer. During our attempt to define the sequences and splice patterns of the MCC and APC gene products in colorectal epithelial cells, we cloned cDNA from the colorectal cancer cell line SW480. The amino acid sequence of the MCC gene from SW480 was identical to that previously found in clones from human brain. The sequence of APC in SW480 cells, however, differed significantly, in that a transition at codon 1338 resulted in a change from glutamine (CAG) to a stop codon (TAG). To determine if this mutation was somatic, we recovered DNA from archival paraffin blocks of the original surgical specimen (T201) from which the tumor cell line was derived 28 years ago.

DNA was purified from paraffin sections as described in S. E. Goelz, S. R. Hamilton, and B. Vogelstein. Biochem. Biophys. Res. Comm. 130, 118 (1985). PCR was performed using the primers 5'-GTTCCAGCAGTGTCACAG-3' (SEQ ID NO: 101) and 5'-GGGAGATTTCGCTCCTGA-3' (SEQ ID NO: 102). A PCR product containing codon 1338 was amplified from the archival DNA and used to show that the stop codon represented a somatic mutation present in the original primary tumor and in cell lines derived from the primary and metastatic tumor sites, but not from normal tissue of the patient.

The ten point mutations in the MCC and APC genes so far discovered in sporadic CRCs are summarized in Table IIB.

Analysis of the number of mutant and wild-type PCR clones obtained from each of these tumors showed that in eight of the ten cases, the wild-type sequence was present in approximately equal proportions to the mutant. This was confirmed by RFLP analysis using flanking markers from chromosome 5q which demonstrated that only two of the ten tumors (T135 and T201) exhibited an allelic deletion on chromosome 5q. These results are consistent with previous observations showing that 20–40% of sporadic colorectal tumors had allelic deletions of chromosome 5q. Moreover, these data suggest that mutations of 5q21 genes are not limited to those colorectal tumors which contain allelic deletions of this chromosome.

EXAMPLE 4

This example characterizes small, nested deletions in DNA from two unrelated FAP patients.

DNA from 40 FAP patients was screened with cosmids that had been mapped into a region near the APC locus to identify small deletions or rearrangements. Two of these cosmids, L5.71 and L5.79, hybridized with a 1200 kb NotI fragment in DNAs from most of the FAP patients screened.

The DNA of one FAP patient, 8214, showed only a 940 kb NotI fragment instead of the expected 1200 kb fragment. DNA was analyzed from four other members of the patient's immediate family; the 940 kb fragment was present in her affected mother (4711), but not in the other, unaffected family members. The mother also carried a normal 1200 kb NotI fragment that was transmitted to her two unaffected offspring. These observations indicated that the mutant polyposis allele is on the same chromosome as the 940 kb NotI fragment. A simple interpretation is that APC patients 3214 and 4711 each carry a 260 kb deletion within the APC locus.

If a deletion were present, then other enzymes might also be expected to produce fragments with altered mobilities. Hybridization of L5.79 to NruI-digested DNAs from both affected members of the family revealed a novel NruI fragment of 1300 kb, in addition to the normal 1200 kb NruI fragment. Furthermore, MluI fragments in patients 3214 and 4711 also showed an increase in size consistent with the deletion of an MluI site. The two chromosome 5 homologs of patient 3214 were segregated in somatic cell hybrid lines; HHW1155 (deletion hybrid) carried the abnormal homolog and HHW1159 (normal hybrid) carried the normal homolog.

Because patient 3214 showed only a 940 kb NotI fragment, she had not inherited the 1200 kb fragment present in the unaffected father's DNA. This observation suggests that he must be heterozygous for, and have transmitted, either a deletion of the L5.79 probe region or a variant NotI fragment too large to resolve on the gel system. As expected, the hybrid cell line HHW1159, which carries the paternal homolog, revealed no resolved Not fragment when probed with L5.79. However, probing of HHW1159 DNA with L5.79 following digestion with other enzymes did reveal restriction fragments, demonstrating the presence of DNA homologous to the probe. The father is, therefore, interpreted as heterozygous for a polymorphism at the NotI site, with one chromosome 5 having a 1200 kb NotI fragment and the other having a fragment too large to resolve consistently on the gel. The latter was transmitted to patient 3214.

When double digests were used to order restriction sites within the 1200 kb NotI fragment, L5.71 and L5.79 were both found to lie on a 550 kb NotI-NruI fragment and, therefore, on the same side of an NruI site in the 1200 kb NotI fragment. To obtain genomic representation of sequences present over the entire 1200 kb NotI fragment, we constructed a library of small-fragment inserts enriched for sequences from this fragment. DNA from the somatic cell hybrid HHW141, which contains about 40% of chromosome 5, was digested with NotI and electrophoresed under pulsed-field gel (PFG) conditions; EcoRI fragments from the 1200 kb region of this gee were cloned into a phage vector. Probe Map30 was isolated from this library. In normal individuals probe Map30 hybridizes to the 1200 kb NotI fragment and to a 200 kb NruI fragment. This latter hybridization places Map30 distal, with respect to the locations of L5.71 and L5.79, to the NruI site of the 550 kb NotI-NruI fragment.

Because Map30 hybridized to the abnormal, 1300 kb NruI fragment of patient 3214, the locus defined by Map30 lies outside the hypothesized deletion. Furthermore, in normal chromosomes Map30 identified a 200 kb NruI fragment and L5.79 identified a 1200 kb NruI fragment; the hypothesized deletion must, therefore, be removing an NruI site, or sites, lying between Map30 and L5.79, and these two probes must flank the hypothesized deletion. A restriction map of the genomic region, showing placement of these probes, is shown in FIG. 5.

A NotI digest of DNA from another FAP patient, 3824, was probed with L5.79. In addition to the 1200 kb normal NotI fragment, a fragment of approximately 1100 kb was observed, consistent with the presence of a 100 kb deletion in one chromosome 5. In this case, however, digestion with NruI and MluI did not reveal abnormal bands, indicating that if a deletion were present, its boundaries must lie distal to the NruI and MluI sites of the fragments identified by L5.79. Consistent with this expectation, hybridization of Map30 to DNA from patient 3824 identified a 760 kb MluI fragment in addition to the expected 860 kb fragment, supporting the interpretation of a 100 kb deletion in this patient. The two chromosome 5 homologs of patient 3824 were segregated in somatic cell hybrid lines; HHW1291 was found to carry only the abnormal homolog and HHW1290 only the normal homolog.

That the 860 kb MluI fragment identified by Map80 is distinct from the 830 kb MluI fragment identified previously by L5.79 was demonstrated by hybridization of Map30 and L5.79 to a NotI-MluI double digest of DNA from the hybrid cell (HHW1159) containing the nondeleted chromosome 5 homolog of patient 3214. As previously indicated, this hybrid is interpreted as missing one of the NotI sites that define the 1200 kb fragment. A 620 kb NotI-MluI fragment was seen with probe L5.79, and an 860 kb fragment was seen with Map30. Therefore, the 830 kb MluI fragment recognized by probe L5.79 must contain a NotI site in HHW1159 DNA; because the 860 kb MluI fragment remains intact, it does not carry this NotI site and must be distinct from the 830 kb MluI fragment.

EXAMPLE 5

This example demonstrates the isolation of human sequences which span the region deleted in the two unrelated FAP patients characterized in Example 4.

A strong prediction of the hypothesis that patients 3214 and 3824 carry deletions is that some sequences present on normal chromosome 5 homologs would be missing from the hypothesized deletion homologs. Therefore, to develop genomic probes that might confirm the deletions, as well as to identify genes from the region, YAC clones from a contig seeded by cosmid L5.79 were localized from a library containing seven haploid human genome equivalents (Albertsen et al., Proc. Natl. Acad. Sci. U.S.A., Vol. 87, pp.

4256–4260 (1990)) with respect to the hypothesized deletions. Three clones, YACs 57B8, 310D8, and 183H12, were found to overlap the deleted region.

Importantly, one end of YAC 57B8 (clone AT57) was found to lie within the patient 3214 deletion. Inverse polymerase chain reaction (PCR) defined the end sequences of the insert of YAC 57B8. PCR primers based on one of these end sequences repeatedly failed to amplify DNA from the somatic cell hybrid (HHW1155) carrying the deleted homolog of patient 3214, but did amplify a product of the expected size from the somatic cell hybrid (HHW1159) carrying the normal chromosome 5 homolog. This result supported the interpretation that the abnormal restriction fragments found in the DNA of patient 3214 result from a deletion.

Additional support for the hypothesis of deletion in DNA from patient 3214 came from subcloned fragments of YAC 183H12, which spans the region in question. Y11, an EcoRI fragment cloned from YAC 183H12, hybridized to the normal, 1200 kb NotI fragment of patient 4711, but failed to hybridize to the abnormal, 940 kb NotI fragment of 4711 or to DNA from deletion cell line HHW1155. This result confirmed the deletion in patient 3214.

Two additional EcoR1 fragments from YAC 183H12, Y10 and Y14, were localized within the patient 3214 deletion by their failure to hybridizie to DNA from HHW1155. Probe Y10 hybridizes to a 150 kb NruI fragment in normal chromosome 5 homologs. Because the 3214 deletion creates the 1300 kb NruI fragment seen with the probes L5.79 and Map30 that flank the deletion, these NruI sites and the 150 kb NruI fragment lying between must be deleted in patient 3214. Furthermore, probe Y10 hybridizes to the same 620 kb NotI-MluI fragment seen with probe L5.79 in normal DNA, indicating its location as L5.79-proximal to the deleted MluI site and placing it between the MluI site and the L5.79-proximal NruI site. The MluI site must, therefore, lie between the NruI sites that define the 150 kb NruI fragment (see FIG. 5).

Probe Y11 also hybridized to the 150 kb NruI fragment in the normal chromosome 5 homolog, but failed to hybridize to the 620 kb NotI-MluI fragment, placing it L5.79-distal to the MluI site, but proximal to the second NruI site. Hybridization to the same (860 kb) MluI fragment as Map30 confirmed the localization of probe Y11 L5.79-distal to the MluI site.

Probe Y14 was shown to be L5.79-distal to both deleted NruI sites by virtue of its hybridization to the same 200 kb NruI fragment of the normal chromosome 5 seen with Map30. Therefore, the order of these EcoRI fragments derived from YAC 183H12 and deleted in patient 3214, with respect to L5.79 and Map30, is L5.79-Y10-Y11-Y14-Map30.

The 100 kb deletion of patient 3824 was confirmed by the failure of aberrant restriction fragments in this DNA to hybridize with probe Y11, combined with positive hybridizations to probes Y10 and/or Y14. Y10 and Y14 each hybridized to the 1100 kb NotI fragment of patient 3824 as well as to the normal 1200 kb NotI fragment, but Y11 hybridized to the 1200 kb fragment only. In the MluI digest, probe Y14 hybridized to the 860 kb and 760 kb fragments of patient 3824 DNA, but probe Y11 hybridized only to the 860 kb fragment. We conclude that the basis for the alteration in fragment size in DNA from patient 3824 is, indeed, a deletion. Furthermore, because probes Y10 and Y14 are missing from the deleted 3214 chromosome, but present on the deleted 3824 chromosome, and they have been shown to flank probe Y11, the deletion in patient 3824 must be nested within the patient 3214 deletion.

Probes Y10, Y11, Y14 and Map30 each hybridized to YAC 310D8, indicating that this YAC spanned the patient 3824 deletion and at a minimum, most of the 3214 deletion. The YAC characterizations, therefore, confirmed the presence of deletions in the patients and provided physical representation of the deleted region.

EXAMPLE 6

This example demonstrates that the MCC coding sequence maps outside of the region deleted in the two FAP patients characterized in Example 4.

An intriguing FAP candidate gene, MCC, recently was ascertained with cosmid L5.71 and was shown to have undergone mutation in colon carcinomas (Kinzler et al., supra). It was therefore of interest to map this gene with respect to the deletions in APC patients. Hybridization of MCC probes with an overlapping series of YAC clones extending in either direction from L5.71 showed that the 3' end of MCC must be oriented toward the region of the two APC deletions.

Therefore, two 3' cDNA clones from MCC were mapped with respect, to the deletions: clone 1CI (bp 2378–4181) and clone 7 (bp 2890–3560). Clone 1CI contains sequences from the C-terminal end of the open reading frame, which stops at nucleotide 2708, as well as 3' untranslated sequence. Clone 7 contains sequence that is entirely 3' to the open reading frame. Importantly, the entire 3' untranslated sequence contained in the cDNA clones consists of a single 2.5 kb exon. These two clones were hybridized to DNAs from the YACs spanning the FAP region. Clone 7 fails to hybridize to YAC 310D8, although it does hybridize to YACs 183H12 and 57B8; the same result was obtained with the cDNA 1CI. Furthermore, these probes did show hybridization to DNAs from both hybrid cell lines (HWW1159 and HWW1155) and the lymphoblastoid cell line from patient 3214, confirming their locations outside the deleted region. Additional mapping experiments suggested that the 3' end of the MCC cDNA clone contig is likely to be located more than 45 kb from the deletion of patient 3214 and, therefore, more than 100 kb from the deletion of patient 3824.

EXAMPLE 7

This example identifies three genes within the deleted region of chromosome 5 in the two unrelated FAP patients characterized in Example 4.

Genomic clones were used to screen cDNA libraries in three separate experiments. One screening was done with a phage clone derived from YAC 310D8 known to span the 260 kb deletion of patient 3214. A large-insert phage library was constructed from this YAC; screening with Y11 identified λ205, which mapped within both deletions. When clone λ205 was used to probe a random-, plus oligo(dT)-, primed fetal brain cDNA library (approximately 300,000 phage), six cDNA clones were isolated and each of them mapped entirely within both deletions. Sequence analysis of these six clones formed a single cDNA contig, but did not reveal an extended open reading frame. One of the six cDNAs was used to isolate more cDNA clones, some of which crossed the L5.71-proximal breakpoint of the 3824 deletion, as indicated by hybridization to both chromosome of this patient. These clones also contained an open reading frame, indicating a transcriptional orientation proximal to distal with respect to L5.71. This gene was named DP1 (deleted in polyposis 1). This gene is identical to TB2 described above.

cDNA walks yielded a cDNA contig of 3.0–3.5 kb, and included two clones containing terminal poly(A) sequences. This size corresponds to the 3.5 kb band seen by Northern analysis. Sequencing of the first 3163 bp of the cDNA contig revealed an open reading frame extending from the first base to nucleotide 631, followed by a 2.5 kb 3' untranslated region. The sequence surrounding the methionine codon at base 77 conforms to the Kozak consensus of an initiation methionine (Kozak, 1984). Failed attempts to walk farther, coupled with the similarity of the lengths of isolated cDNA and mRNA, suggested that the $NH_2$-terminus of the DP1 protein had been reached. Hybridization to a combination of genomic and YAC DNAs cut with various enzymes indicated the genomic coverage of DP1 to be approximately 30 kb.

Two additional probes for the locus, YS-11 and YS-39, which had been ascertained by screening of a cDNA library with an independent YAC probe identified with MCC sequences adjacent to L5.71, were mapped into the deletion region. YS-39 was shown to be a cDNA identical in sequence to DP1. Partial characterization of YS-11 had shown that 200 bp of DNA sequence at one end was identical to sequence coding for the 19 kd protein of the ribosomal signal recognition particle, SRP19 (Lingelbach et al., supra). Hybridization experiments mapped YS-11 within both deletions. The sequence of this clone, however, was found to be complex. Although 454 bp of the 1032 bp sequence of YS-11 were identical to the GenBank entry for the SRP19 gene, another 578 bp appended 5' to the SRP19 sequence was found to consist of previously unreported sequence containing no extended open reading frames. This suggested that YS-11 was either a chimeric clone containing two independent inserts or a clone of an incompletely processed or aberrant message. If YS-11 were a conventional chimeric clone, the independent segments would not be expected to map to the same physical region. The segments resulting from anomalous processing of a continuous transcript, however, would map to a single chromosomal region.

Inverse PCR with primers specific to the two ends of YS-11, the SRP19 end and the unidentified region, verified that both sequences map within the YAC 310D8; therefore, YS-11 is most likely a clone of an immature or anomalous mRNA species. Subsequently, both ends were shown to lie with the deleted region of patient 3824, and YS-11 was used to screen for additional cDNA clones.

Of the 14 cDNA clones selected from the fetal brain library, one clone, V5, was of particular interest in that it contained an open reading frame throughout, although it included only a short identity to the first 78 5' bases of the YS-11 sequence. Following the 78 bp of identical sequence, the two cDNA sequences diverged at an AG. Furthermore, divergence from genomic sequence was also seen after these 78 bp, suggesting the presence of a splice junction, and supporting the view that YS-11 represents an irregular message.

Starting with V5, successive 5' and 3' walks were performed; the resulting cDNA contig consisted of more than 100 clones, which defined a new transcript, DP2. Clones walking in the 5' direction crossed the 3824 deletion breakpoint farthest from L5.71; since its 3' end is closer to this cosmid than its 5' end, the transcriptional orientation of DP2 is opposite to that of MCC and DP1.

The third screening approach relied on hybridization with a 120 kb MluI fragment from YAC 57B8. This fragment hybridizes with probe Y11 and completely spans the 100 kb deletion in patient 3824. the fragment was purified on two preparative PFGs, labeled, and used to screen a fetal brain cDNA library. A number of cDNA clones previously identified in the development of the DP1 and DP2 contigs were reascertained. However, 19 new cDNA clones mapped into the patient 3824 deletion. Analysis indicated that these 19 formed a new contig, DP3, containing a large open reading frame.

A clone from the 5' end of this new cDNA contig hybridized to the same EcoRI fragment as the 3' end of DP2. Subsequently, the DP2 and DP3 contigs were connected by a single 5' walking step from DP3, to form the single contig DP2.5. The complete nucleotide sequence of DP2.5 is shown in FIG. 9.

The consensus cDNA sequence of DP2.5 suggests that the entire coding sequence of DP2.5 has been obtained and is 8532 bp long. The most 5' ATG codon occurs two codons from an in-frame stop and conforms to the Kozak initiation consensus (Kozak, Nucl. Acids. Res., Vol. 12, p. 857–872 1984). The 3' open reading frame breaks down over the final 1.8 kb, giving multiple stops in all frames. A poly(A) sequence was found in one clone approximately 1 kb into the 3' untranslated region, associated with a polyadenylation signal 33 bp upstream (position 9530). The open reading frame is almost identical to that identified as APC above.

An alternatively spliced exon at nucleotide 934 of the DP2.5 transcript is of potential interest. it was first discovered by noting that two classes of cDNA had been isolated. The more abundant cDNA class contains a 303 bp exon not included in the other. The presence in vivo of the two transcripts was verified by an exon connection experiment. Primers flanking the alternatively spliced exon were used to amplify, by PCR, cDNA prepared from various adult tissues. Two PCR products that differed in size by approximately 300 bases were amplified from all the tissues tested; the larger product was always more abundant than the smaller.

EXAMPLE 8

This example demonstrates the primers used to identify subtle mutations in DP1, SRP19, and DP25.

To obtain DNA sequence adjacent to the exons of the genes DP1, DP2.5, and SRP19, sequencing substrate was obtained by inverse PCR amplification of DNAs from two YACs, 310D8 and 183H12, that span the deletions. Ligation at low concentration cyclized the restriction enzyme-digested YAC DNAs. Oligonucleotides with sequencing tails, designed in Inverse orientation at intervals along the cDNAs, primed PCR amplification from the cyclized templates. Comparison of these DNA sequences with the cDNA sequences placed exon boundaries at the divergence points. SRP19 and DP1 were each shown to have five exons. DP2.5 consisted of 15 exons. The sequences of the oligonucleotides synthesized to provide PCR amplification primers for the exons of each of these genes are listed in Table III (SEQ ID NO: 39–94). With the exception of exons 1, 3, 4, 9, and 15 of DP2.5 (see below), the primer sequences were located in intron sequences flanking the exons. The 5' primer of exon 1 is complementary to the cDNA sequence, but extends just into the 5' Kozak consensus sequence for the initiator methionine, allowing a survey of the translated sequences. The 5' primer of exon 3 is actually in the 5' coding sequences of this exon, as three separate intronic primers simply would not amplify. The 5' primer of exon 4 just overlaps the 5' end of this exon, and we thus fail to survey the 19 most 5' bases of this exon. For exon 9, two overlapping primer sets were used, such that each had one end within the exon. For exon 15, the large 3' exon of DP2.5, overlapping primer pairs were placed along the length of the exon; each pair amplified a product of 250-400 bases.

EXAMPLE 9

This example demonstrates the use of single stranded conformation polymorphism (SSCP) analysis as described by Orita et al. Proc. Natl. Acad. Sci. U.S.A., Vol. 86, pp. 2766-70 (1989) and Genomics, Vol. 5, pp. 874-879 (1989) as applied to DP1, SRP19 and DP2.5.

SSCP analysis identifies most single- or multiple-base changes in DNA fragments up to 400 bases in length. Sequence alterations are detected as shifts in electrophoretic mobility of single-stranded DNA on nondenaturing acrylamide gels; the two complementary strands of a DNA segment usually resolve as two SSCP conformers of distinct mobilities. However, if the sample is from an individual heterozygous for a base-pair variant within the amplified segment, often three or more bands are seen. In some cases, even the sample from a homozygous individual will show multiple bands. Base-pair-change variants are identified by differences in pattern among the DNAs of the sample set.

Exons of the candidate genes were amplified by PCR from the DNAs of 61 unrelated FAP patients and a control set of 12 normal individuals. The five exons from DP1 revealed no unique conformers in the FAP patients, although common conformers were observed with exons 2 and 3 in some individuals of both affected and control sets, indicating the presence of DNA sequence polymorphisms. Likewise, none of the five exons of SRP19 revealed unique conformers in DNA from FAP patients in the test panel.

Testing of exons 1 through 14 and primer sets A through N of exon 15, of the DP2.5 gene, however, revealed variant conformers specific to FAP patients in exons 7, 8, 10, 11, and 15. These variants were in the unrelated patients 3746, 3460, 3827, 3712, and 3751, respectively. The PCR-SSCP procedure was repeated for each of these exons in the five affected individuals and in an expanded set of 48 normal controls. The variant bands were reproducible in the FAP patients but were not observed in any of the control DNA samples. Additional variant conformers in exons 11 and 15 of the DP2.5 gene were seen; however, each of these was found in both the affected and control DNA sets. The five sets of conformers unique to the FAP patients were sequenced to determine the nucleotide changes responsible for their altered mobilities. The normal conformers from the host individuals were sequenced also. Bands were cut from the dried acrylamide gels, and the DNA was eluted. PCR amplification of these DNAs provided template for sequencing.

The sequences of the unique conformers from exons 7, 8, 10, and 11 of DP2.5 revealed dramatic mutations in the DP2.5 gene. The sequence of the new mutation creating the exon 7 conformer in patient 3746 was shown to contain a deletion of two adjacent nucleotides, at positions 730 and 731 in the cDNA sequence (FIG. 7, SEQ ID NO: 1). The normal sequence at this splice junction is CAGGGTCA (intronic sequence underlined), with the intron-exon boundary between the two repetitions of AG. The mutant allele in this patient has the sequence CAGGTCA. Although this change is at the 5' splice site, comparison with known consensus sequences of splice junctions would suggest that a functional splice junction is maintained. If this new splice junction were functional, the mutation would introduce a frameshift that creates a stop codon 15 nucleotides downstream. If the new splice junction were not functional, messenger processing would be significantly altered.

To confirm the 2-base deletion, the PCR product from FAP patient 3746 and a control DNA were electrophoresed on an acrylamide-urea denaturing gel, along with the products of a sequencing reaction. The sample from patient 3746 showed two bands differing in size by 2 nucleotides, with the larger band identical in mobility to the control sample; this result was independent confirmation that patient, 3746 is heterozygous for a 2 bp deletion.

The unique conformer found in exon 8 of patient 3460 was found to carry a C-T transition, at position 904 in the cDNA sequence of DP2.5 (shown in FIG. 7), which replaced the normal sequence of CGA with TGA. This point mutation, when read in frame, results in a stop codon replacing the normal arginine codon. This single-base change had occurred within the context of a CG dimer, a potential hot spot for mutation (Barker et al., 1984).

The conformer unique to FAP patient 3827 in exon 10 was found to contain a deletion of one nucleotide (1367, 1368, or 1369) when compared to the normal sequence found in the other bands on the SSCP gel. This deletion, occurring within a set of three T's, changed the sequence from CTTTCA to CTTCA; this 1 base frameshift creates a downstream stop within 30 bases. The PCR product amplified from this patient's DNA also was electrophoresed on an acrylamide-urea denaturing gel, along with the PCR product from a control DNA and products from a sequencing reaction. The patient's PCR product showed two bands differing by 1 bp in length, with the larger identical in mobility to the PCR product from the normal DNA; this result confirmed the presence of a 1 bp deletion in patient 3827.

Sequence analysis of the variant conformer of exon 11 from patient 3712 revealed the substitution of a T by a G at position 1500, changing the normal tyrosine codon to a stop codon.

The pair of conformers observed in exon 15 of the DP2.5 gene for FAP patient 3751 also was sequenced. These conformers were found to carry a nucleotide substitution of C to G at position 5253, the third base of a valine codon. No amino acid change resulted from this substitution, suggesting that this conformer reflects a genetically silent polymorphism.

The observation of distinct inactivating mutations in the DP2.5 gene in four unrelated patients strongly suggested that DP2.5 is the gene involved in FAP. These mutations are summarized in Table IIA.

EXAMPLE 10

This example demonstrates that the mutations identified in the DP2.5 (APC) gene segregate with the FAP phenotype.

Patient 3746, described above as carrying an APC allele with a frameshift mutation, is an affected offspring of two normal parents. Colonoscopy revealed no polyps in either parent nor among the patient's three siblings.

DNA samples from both parents, from the patient's wife, and from their three children were examined. SSCP analysis of DNA from both of the patients parents displayed the normal pattern of conformers for exon 7, as did DNA from the patients's wife and one of his off-spring. The two other children, however, displayed the same new conformers as their affected father. Testing of the patient and his parents with highly polymorphic VNTR (variable number of tandem repeat) markers showed a 99.98% likelihood that they are his biological parents.

These observations confirmed that this novel conformer, known to reflect a 2 bp deletion mutation in the DP2.5 gene, appeared spontaneously with FAP in this pedigree and was transmitted to two of the children of the affected individual.

EXAMPLE 11

This example demonstrates polymorphisms in the APC gene which appear to be unrelated to disease (FAP).

Sequencing of variant conformers found among controls as well as individuals with APC has revealed the following polymorphisms in the APC gene: first, in exon 11, at position 1458, a substitution of T to C creating an RsaI restriction site but no amino acid change; and second, in exon 15, at positions 5037 and 5271, substitutions of A to G and G to T, respectively, neither resulting in amino acid substitutions. These nucleotide polymorphisms in the APC gene sequence may be useful for diagnostic purposes.

EXAMPLE 12

This example shows the structure of the APC gene.

The structure of the APC gene is schematically shown in FIG. 8, with flanking intron sequences indicated (SEQ ID NO: 11–38).

The continuity of the very large (6.5 kb), most 3' exon in DP2.5 was shown in two ways. First, inverse PCR with primers spanning the entire length of this exon revealed no divergence of the cDNA sequence from the genomic sequence. Second, PCR amplification with converging primers placed at intervals along the exon generated products of the same size whether amplified from the originally isolated cDNA, cDNA from various tissues, or genomic template. Two forms of exon 9 were found in DP2.5: one is the complete exon; and the other, labeled exon 9A, is the result of a splice into the interior of the exon that deletes bases 934 to 1236 in the mRNA and removes 101 amino acids from the predicted protein (see FIG. 7, SEQ ID NO: 1 and 2).

EXAMPLE 13

This example demonstrates the mapping of the FAP deletions with respect to the APC exons.

Somatic cell hybrids carrying the segregated chromosomes 5 from the 100 kb (HHW1291) and 260 kb (HHW1155) deletion patients were used to determine the distribution of the APC genes exons across the deletions. DNAs from these cell lines were used as template, along with genomic DNA from a normal control, for PCR-based amplification of the APC exons.

PCR analysis of the hybrids from the 260 kb deletion of patient 3214 showed that all but one (exon 1) of the APC exons are removed by this deletion. PCR analysis of the somatic cell hybrid HHW1291, carrying the chromosome 5 homolog with the 100 kb deletion from patient 3824, revealed that exons 1 through 9 are present but exons 10 through 15 are missing. This result placed the deletion breakpoint either between exons 9 and 10 or within exon 10.

EXAMPLE 14

This example demonstrates the expression of alternately spliced APC messenger in normal tissues and in cancer cell lines.

Tissues that express the APC gene were identified by PCR amplification of cDNA made to mRNA with primers located within adjacent APC exons. In addition, PCR primers that flank the alternatively spliced exon 9 were chosen so that the expression pattern of both splice forms could be assessed. All tissue types tested (brain, lung, aorta, spleen, heart, kidney, liver, stomach, placenta, and colonic mucosa) and cultured cell lines (lymphoblasts, HL60, and choriocarcinoma) expressed both splice forms of the APC gene. We note, however, that expression by lymphocytes normally residing in some tissues, including colon, prevents unequivocal assessment of expression. The large mRNA, containing the complete exon 9 rather than only exon 9A, appears to be the more abundant message.

Northern analysis of poly(A)-selected RNA from lymphoblasts revealed a single band of approximately 10 kb, consistent with the size of the sequenced cDNA.

EXAMPLE 15

This example discusses structural features of the APC protein predicted from the sequence.

The cDNA consensus sequence of APC predicts that the longer, more abundant form of the message codes for a 2842 or 2844 amino acid peptide with a mass of 311.8 kd. This predicted APC peptide was compared with the current data bases of protein and DNA sequences using both Intelligenetics and GCG software packages. No genes with a high degree of amino acid sequence similarity were found. Although many short (approximately 20 amino acid) regions of sequence similarity were uncovered, none was sufficiently strong to reveal which, if any, might represent functional homology. Interestingly, multiple similarities to myosins and keratins did appear. The APC gene also was scanned for sequence motifs of known function; although multiple glycosylation, phosphorylation, and myristoylation sites were seen, their significance is uncertain.

Analysis of the APC peptide sequence did identify features important in considering potential protein structure. Hydropathy plots (Kyte and Doolittle, J. Mol. Biol. Vol. 157, pp. 105–132 (1982)) indicate that the APC protein is notably hydrophilic. No hydrophobic domains suggesting a signal peptide or a membrane-spanning domain were found. Analysis of the first 1000 residues indicates that α-helical rods may form (Cohen and Parry, Trends Biochem, Sci. Vol. 77, pp. 245–248 (1986); there is a scarcity of proline residues and, there are a number of regions containing heptad repeats (apolar-X-X-apolar-X-X-X). Interestingly, in exon 9A, the deleted form of exon 9, two heptad repeat regions, are reconnected in the proper heptad repeat frame, deleting the intervening peptide region. After the first 1000 residues, the high proline content of the remainder of the peptide suggests a compact rather than a rod-like structure.

The most prominent feature of the second 1000 residues is a 20 amino acid repeat that is iterated seven times with semiregular spacing (Table 4). The intervening sequences between the seven repeat regions contained 114, 116, 151, 205, 107, and 58 amino acids, respectively. Finally, residues 2200–24000 contain a 200 amino acid basic domain.

TABLE I

APC EXONS

| EXON NUCLEOTIDES[1] | EXON BOUNDARY SEQUENCE[2] |
|---|---|
| 822 to 930 | catgatgttatctgtatttacctatagtctaaattataccatctataatgtgcttaatttttag/GGTTCA . . . (SEQ ID NO: 24) |
|  | . . . ACCAAG/gtaacagaagattacaaaccctggtcactaatgccatgactactttgctaag (SEQ ID NO: 25) |
| 931 to 1309 | ggatattaaagtcgtaattttgtttctaaactcatttggcccacag/GTGGAA . . . (SEQ ID NO: 26) |
|  | . . . ATCCAA/gtatgttctctatagtgtacatcgtagtgcatg (SEQ ID NO: 27) |
| 1310 to 1405 | catcattgctcttcaaataacaaagcattatggtttatgttgattttattttttcag/TGCCAG . . . (SEQ ID NO: 28) |
|  | . . . AACTAG/gtaagacaaaaatgtttttaatgacatagacaattactggtg (SEQ ID NO: 29) |
| 1406 to 1545 | tagatgattgtcttttcctcttgcccttttttaaattag/GGGGAC . . . (SEQ ID NO: 30) |
|  | . . . AACAAG/gtatgttttataacatgtatttcttaagatagctcaggtatga (SEQ ID NO: 31) |
| 1546 to 1623 | gcttggcttcaagttgtcttttaatgatcctctattctgtatttaatttacag/GCTACG . . . (SEQ ID NO: 32) |
|  | . . . CAGCAG/gtactatttagaatttcacctgtttttcttttctcttttcttttgaggcagggtctcactctg (SEQ ID NO: 33) |
| 1624 to 1740 | gcaactagtatgattttatgtataaattaatctaaaattgattaatttgcag/GTTATT . . . (SEQ ID NO: 34) |
|  | . . . AAAAAG/gtaccttttgaaaacatttagtactataatatgaatttcatgt (SEQ ID NO: 35) |
| 1741 to 1955 | caactctaattagatgaccatattcagaaacttactag/GATCA . . . (SEQ ID NO: 36) |
|  | . . . CCACAG/gtatatatagagtttttatattacttttaaagtacagaattcatactctcaaaaa (SEQ ID NO: 37) |
| 1956 to 8973[3] | tcttgattttattttcag/GCAAAT . . . (SEQ ID NO: 38) |
|  | . . . GGTATTTATGCAAAAAAAAATGTTTTTGT (SEQ ID NO: 1) |

[1] Relative to predicted translation initiation site
[2] Small case letters represent introns, large case letters represent exons
[3] The entire 3' end of the cloned APC cDNA (nt 1956–8973) appeared to be encoded in this exon, as indicated by restriction endonuclease mapping and sequencing of cloned genomic DNA. The ORF ended at nt 8535. The extreme 3' end of the APC transcript has not yet been identified.

TABLE IIA

Germline mutations of the APC gene in FAP and GS Patients

| Patient | Codon | Nucleotide Change | Amino Acid Change | Age | Extracolonic Disease |
|---|---|---|---|---|---|
| 93 | 279 | TCA→TGA | Ser→Stop | 39 | Mandibular Osteoma |
| 24 | 301 | CGA→TGA | Arg→Stop | 46 | None |
| 34 | 301 | CGA→TGA | Arg→Stop | 27 | Desmoid Tumor |
| 21 | 413 | CGC→TGC | Arg→Cys | 24 | Mandibular Osteoma |
| 60 | 712 | TCA→TGA | Ser→Stop | 37 | Mandibular Osteoma |
| 3736 | 243 | CAGAG→AG | splice-junction |  |  |
| 3460 | 301 | CGA→TGA | Arg→stop |  |  |
| 3827 | 456 | CTTTCA→CTTCA | frameshift |  |  |
| 3712 | 500 | T→G | Tyr→Stop |  |  |

*The mutated nucleotides are underlined.

TABLE IIB

Somatic Mutations in Sporadic CRC Patients

| PATIENT | CODON[1] | NUCLEOTIDE CHANGE | AMINO ACID CHANGE |
|---|---|---|---|
| T35 | MCC 12 | GAG/gtaaga→GAG/gtaaaa | (Splice Donor) |
| T16 | MCC 145 | ctcag/GGA→atcag/GGA | (Splice Acceptor) |
| T47 | MCC 267 | CGG→CTG | Arg→Leu |
| T81 | MCC 490 | TCG→TTG | Ser→Leu |
| T35 | MCC 506 | CGG→CAG | Arg→Gln |
| T91 | MCC 698 | GCT→GTT | Ala→Val |
| T34 | APC 288 | CCAGT→CCCAGCCAGT | (Insertion) |
| T27 | APC 331 | CGA→TGA | Arg→Stop |
| T135 | APC 437 | CAA/gtaa→CAA/gcaa | (Splice Donor) |
| T201 | APC 1338 | CAG→TAG | Gln→Stop |

For splice site mutations, the codon nearest to the mutation is listed
The underlined nucleotides were mutant; small can letters represent introns, large case letters represent exons

TABLE III

Sequences of Primers Used for SSCP Analyses

| Exon | Primer 1 | Primer 2 |
|---|---|---|
| | DP1 | |
| | UP-TCCCCGCCTGCCGCTCTC | RP-GCAGCGGCGGCTCCCGTG |
| | UP-GTGAACGGCTCTCATGCTGC | RP-ACGTGCGGGGAGGAATGGA |
| | UP-ATGATATCTTACCAAATGATATAC | RP-TTATTCCTACTTCTTCTATACAG |
| | UP-TACCCATGCTGGCTCTTTTTC | RP-TGGGGCCATCTTGTTCCTGA |
| | UP-ACATTAGGCACAAAGCTTGCAA | RP-ATCAAGCTCCAGTAAGAAGGTA |
| | SRP19 | |
| | UP-TGCGGCTCGTGGGTTGTTG | RP-GCCCCTTCCTTTCTGAGGAC |
| | UP-TTTTCTCCTGCCTCTTACTGC | RP-ATGACACCCCCCATTCCCTC |
| | UP-CCACTTAAAGCACATATATTTAGT | RP-GTATGGAAAATAGTGAAGAACC |
| | UP-TTCTTAAGTCCTGTTTTTCTTTTG | RP-TTTAGAACCTTTTTTGTGTTGTG |
| | UP-CTCAGATTATACACTAAGCCTAAC | RP-CATGTCTCTTACAGTAGTACCA |
| | DP2.5 | |
| | UP-AGGTCCAAGGGTAGCCAAGG* | RP-TAAAAATGGATAAACTACAATTAAAAG |
| | UP-AAATACAGAATCATGTCTTGAAGT | RP-ACACCTAAAGATGACAATTTGAG |
| | UP-TAACTTAGATAGCAGTAATTTCCC* | RP-ACAATAAACTGGAGTACACAAGG |
| | UP-ATAGGTCATTGCTTCTTGCTGAT* | RP-TGAATTTTAATGGATTACCTAGGT |
| | UP-CTTTTTTTGCTTTTACTGATTAACG | RP-TGTAATTCATTTTATTCCTAATACCTC |
| | UP-GGTAGCCATAGTATGATTATTTCT | RP-CTACCTATTTTTATACCCACAAAC |
| | UP-AAGAAAGCCTACACCATTTTTGC | RP-GATCATTCTTAGAACCATCTTGC |
| | UP-ACCTATAGTCTAAATTATACCATC | RP-GTCATGGCATTACTGACCAG |
| | UP-AGTCGTAATTTTGTTTCTAAACTC | RP-TGAAGGACTCCGATTTCACCC* |
| | UP-TCATTCACTCACAGCCTGATGAC* | RP-GCTTTGAAACATGCACTACGAT |
| | UP-AAACATCATTGCTCTTCAAATAAC | RP-TACCATGATTTAAAAATCCACCAG |
| | UP-GATGATTGTCTTTTTCCTCTTGC | RP-CTGAGCTATCTTAAGAAATACATG |
| | UP-TTTTAAATGATCCTCTATTCTGTAT | RP-ACAGAGTCAGACCCTCCCTCAAAG |
| | UP-TTTCTATTCTTACTGCTAGCATT | RP-ATACACAGGTAAGAAATTAGGA |
| | UP-TAGATGACCCATATTCTCTTTC | RP-CAATTAGGTCTTTTTGAGAGTA |
| 3-A | UP-GTTACTGCATACACATTGTGAC | RP-GCTTTTTGTTTCGTAACATGAAG* |
| -B | UP-AGTACAAGGATGCCAATATTATG* | RP-ACTTCTATCTTTTTCAGAACGAG* |
| -C | UP-ATTTGAATACTACAGTGTTACCC* | RP-CTTGTATTCTAATTTGGCATAAGG* |
| -D | UP-CTGCCCATACACATTCAAACAC* | RP-TGTTTGCGTCTTGCCCATCTT* |
| -E | UP-AGTCTTAAATATTCAGATGAGCAG* | RP-GTTTCTCTTCATTATATTTTATGCTA* |
| -F | UP-AAGCCTACCAATTATAGTGAACG* | RP-AGCTGATGACAAAGATGATAATC* |
| -G | UP-AAGAAACAATACAGACTTATTGTG* | RP-ATGAGTGGGGTCTCCTGAAC* |
| -H | UPATCTCCCTCCAAAAGTGGTGC* | RP-TCCATCTGGAGTACTTTCTGTG* |
| -I | UP-AGTAAATGCTGCAGTTCAGAGG* | RP-CCGTGGCATATCATCCCCC* |
| -J | UP-CCCAGACTGCTTCAAAATTACC* | RP-GAGCCTCATCTGTACTTCTGC* |
| -K | UP-CCCTCCAAATGAGTTAGCTGC* | RP-TTGTGGTATAGGTTTTACTGGTG* |
| -L | UP-ACCCAACAAAAATCAGTTAGATG* | RP-GTGGCTGGTAACTTTAGCCTC* |
| -N | UP-ATGATGTTGACCTTTCCAGGG* | RP-ATTGTGTAACTTTTCATCAGTTGC* |
| -M | UP-AAAGACATACCAGACAGAGGG* | RP-CTTTTTTGGCATTGCGGAGCT* |
| -O | UP-AAGATGACCTGTTGCAGGAATG* | RP-GAATCAGACCAAGCTTGTCTAGAT* |
| -P | UP-CAATAGTAAGTAGTTTACATCAAG* | RP-AAACAGGACTTGTACTGTAGGA* |
| -Q | UP-CAGCCCCTTCAAGCAAACATC* | RP-GAGGACTTATTCCATTTCTACC* |
| -R | UP-CAGTCTCCTGGCCGAAACTC* | RP-GTTGACTGGCGTACTAATACAG* |
| -S | UP-TGGTAATGGAGCCAATAAAAAGG* | RP-TGGGACTTTTCGCCATCCAC* |
| -T | UP-TGTCTCTATCCACACATTCGTC* | RP-ATGTTTTTCATCCTCACTTTTTGC* |
| -U | UP-GGAGAAGAACTGGAAGTTCATC* | RP-TTGAATCTTTAATGTTTGGATTTGC* |
| -V | UP-TCTCCCACAGGTAATACTCCC | RP-GCTACAACTGAATGGGGTACG |
| -W | UP-CAGGACAAAATAATCCTGTCCC | RP-ATTTTCTTACTTTCATTCTTCCTC |

All primers are read in the 5' to 3' direction. the first primer in each pair lies 5' of the exon it amplifies: the second primer lies 3' of the exon it amplifies. Primers that lie within the exon are identified by an asterisk. UP represents the - 21M13 universal primer sequence: RP represents the M13 reverse primer sequence.

TABLE IV

Seven Different Versions of the 20-Amino Acid Repeat

| | | | | | | | | | | | | | | | | | | | | |
|---|---|---|---|---|---|---|---|---|---|---|---|---|---|---|---|---|---|---|---|---|
| Consensus: | F | ø | V | E | ø | T | P | ø | C | F | S | R | ø | S | S | L | S | S | L | S |
| 1262: | Y | C | V | E | D | T | P | I | C | F | S | R | C | S | S | L | S | S | L | S |
| 1376: | H | Y | V | Q | E | T | P | L | M | F | S | R | C | T | S | V | S | S | L | D |
| 1492: | F | A | T | E | S | T | P | D | G | F | S | C | S | S | S | L | S | A | L | S |
| 1643: | Y | C | V | E | G | T | P | I | N | F | S | T | A | T | S | L | S | D | L | T |
| 1848: | T | P | I | E | G | T | P | Y | C | F | S | R | N | D | S | L | S | S | L | D |
| 1953: | F | A | I | E | N | T | P | V | C | P | S | H | N | S | L | S | S | L | S |
| 2013: | F | H | V | E | D | T | P | V | C | F | S | R | N | S | S | L | S | S | L | S |

Numbers denote the first amino acid of each repeat. The consensus sequence at the top reflects a majority amino acid at a given position.

5,648,212

SEQUENCE LISTING ( 1 ) GENERAL INFORMATION:

( i i i ) NUMBER OF SEQUENCES: 102

( 2 ) INFORMATION FOR SEQ ID NO:1:

( i ) SEQUENCE CHARACTERISTICS:
        ( A ) LENGTH: 9606 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: DP2.5(APC)

( i x ) FEATURE:
        ( A ) NAME/KEY: CDS
        ( B ) LOCATION: 34..8562

( x i ) SEQUENCE DESCRIPTION: SEQ ID NO:1:

```
GGACTCGGAA ATGAGGTCCA AGGGTAGCCA AGG ATG GCT GCA GCT TCA TAT GAT            54
                                    Met Ala Ala Ala Ser Tyr Asp
                                     1               5

CAG TTG TTA AAG CAA GTT GAG GCA CTG AAG ATG GAG AAC TCA AAT CTT            102
Gln Leu Leu Lys Gln Val Glu Ala Leu Lys Met Glu Asn Ser Asn Leu
         10              15                  20

CGA CAA GAG CTA GAA GAT AAT TCC AAT CAT CTT ACA AAA CTG GAA ACT            150
Arg Gln Glu Leu Glu Asp Asn Ser Asn His Leu Thr Lys Leu Glu Thr
     25              30                  35

GAG GCA TCT AAT ATG AAG GAA GTA CTT AAA CAA CTA CAA GGA AGT ATT            198
Glu Ala Ser Asn Met Lys Glu Val Leu Lys Gln Leu Gln Gly Ser Ile
 40              45                  50                      55

GAA GAT GAA GCT ATG GCT TCT TCT GGA CAG ATT GAT TTA TTA GAG CGT            246
Glu Asp Glu Ala Met Ala Ser Ser Gly Gln Ile Asp Leu Leu Glu Arg
             60                  65                  70

CTT AAA GAG CTT AAC TTA GAT AGC AGT AAT TTC CCT GGA GTA AAA CTG            294
Leu Lys Glu Leu Asn Leu Asp Ser Ser Asn Phe Pro Gly Val Lys Leu
             75                  80                  85

CGG TCA AAA ATG TCC CTC CGT TCT TAT GGA AGC CGG GAA GGA TCT GTA            342
Arg Ser Lys Met Ser Leu Arg Ser Tyr Gly Ser Arg Glu Gly Ser Val
         90                  95                 100

TCA AGC CGT TCT GGA GAG TGC AGT CCT GTT CCT ATG GGT TCA TTT CCA            390
Ser Ser Arg Ser Gly Glu Cys Ser Pro Val Pro Met Gly Ser Phe Pro
105                 110                 115

AGA AGA GGG TTT GTA AAT GGA AGC AGA GAA AGT ACT GGA TAT TTA GAA            438
Arg Arg Gly Phe Val Asn Gly Ser Arg Glu Ser Thr Gly Tyr Leu Glu
120                 125                 130                 135

GAA CTT GAG AAA GAG AGG TCA TTG CTT CTT GCT GAT CTT GAC AAA GAA            486
Glu Leu Glu Lys Glu Arg Ser Leu Leu Leu Ala Asp Leu Asp Lys Glu
                140                 145                 150

GAA AAG GAA AAA GAC TGG TAT TAC GCT CAA CTT CAG AAT CTC ACT AAA            534
Glu Lys Glu Lys Asp Trp Tyr Tyr Ala Gln Leu Gln Asn Leu Thr Lys
                155                 160                 165

AGA ATA GAT AGT CTT CCT TTA ACT GAA AAT TTT TCC TTA CAA ACA GAT            582
Arg Ile Asp Ser Leu Pro Leu Thr Glu Asn Phe Ser Leu Gln Thr Asp
            170                 175                 180

TTG ACC AGA AGG CAA TTG GAA TAT GAA GCA AGG CAA ATC AGA GTT GCG            630
```

```
Leu Thr Arg Arg Gln Leu Glu Tyr Glu Ala Arg Gln Ile Arg Val Ala
    185             190                 195

ATG GAA GAA CAA CTA GGT ACC TGC CAG GAT ATG GAA AAA CGA GCA CAG        678
Met Glu Glu Gln Leu Gly Thr Cys Gln Asp Met Glu Lys Arg Ala Gln
200             205                 210                 215

CGA AGA ATA GCC AGA ATT CAG CAA ATC GAA AAG GAC ATA CTT CGT ATA        726
Arg Arg Ile Ala Arg Ile Gln Gln Ile Glu Lys Asp Ile Leu Arg Ile
                220                 225                 230

CGA CAG CTT TTA CAG TCC CAA GCA ACA GAA GCA GAG AGG TCA TCT CAG        774
Arg Gln Leu Leu Gln Ser Gln Ala Thr Glu Ala Glu Arg Ser Ser Gln
            235                 240                 245

AAC AAG CAT GAA ACC GGC TCA CAT GAT GCT GAG CGG CAG AAT GAA GGT        822
Asn Lys His Glu Thr Gly Ser His Asp Ala Glu Arg Gln Asn Glu Gly
        250                 255                 260

CAA GGA GTG GGA GAA ATC AAC ATG GCA ACT TCT GGT AAT GGT CAG GGT        870
Gln Gly Val Gly Glu Ile Asn Met Ala Thr Ser Gly Asn Gly Gln Gly
265                 270                 275

TCA ACT ACA CGA ATG GAC CAT GAA ACA GCC AGT GTT TTG AGT TCT AGT        918
Ser Thr Thr Arg Met Asp His Glu Thr Ala Ser Val Leu Ser Ser Ser
280                 285                 290                 295

AGC ACA CAC TCT GCA CCT CGA AGG CTG ACA AGT CAT CTG GGA ACC AAG        966
Ser Thr His Ser Ala Pro Arg Arg Leu Thr Ser His Leu Gly Thr Lys
                300                 305                 310

GTG GAA ATG GTG TAT TCA TTG TTG TCA ATG CTT GGT ACT CAT GAT AAG       1014
Val Glu Met Val Tyr Ser Leu Leu Ser Met Leu Gly Thr His Asp Lys
            315                 320                 325

GAT GAT ATG TCG CGA ACT TTG CTA GCT ATG TCT AGC TCC CAA GAC AGC       1062
Asp Asp Met Ser Arg Thr Leu Leu Ala Met Ser Ser Ser Gln Asp Ser
        330                 335                 340

TGT ATA TCC ATG CGA CAG TCT GGA TGT CTT CCT CTC CTC ATC CAG CTT       1110
Cys Ile Ser Met Arg Gln Ser Gly Cys Leu Pro Leu Leu Ile Gln Leu
345                 350                 355

TTA CAT GGC AAT GAC AAA GAC TCT GTA TTG TTG GGA AAT TCC CGG GGC       1158
Leu His Gly Asn Asp Lys Asp Ser Val Leu Leu Gly Asn Ser Arg Gly
360                 365                 370                 375

AGT AAA GAG GCT CGG GCC AGG GCC AGT GCA GCA CTC CAC AAC ATC ATT       1206
Ser Lys Glu Ala Arg Ala Arg Ala Ser Ala Ala Leu His Asn Ile Ile
                380                 385                 390

CAC TCA CAG CCT GAT GAC AAG AGA GGC AGG CGT GAA ATC CGA GTC CTT       1254
His Ser Gln Pro Asp Asp Lys Arg Gly Arg Arg Glu Ile Arg Val Leu
        395                 400                 405

CAT CTT TTG GAA CAG ATA CGC GCT TAC TGT GAA ACC TGT TGG GAG TGG       1302
His Leu Leu Glu Gln Ile Arg Ala Tyr Cys Glu Thr Cys Trp Glu Trp
            410                 415                 420

CAG GAA GCT CAT GAA CCA GGC ATG GAC CAG GAC AAA AAT CCA ATG CCA       1350
Gln Glu Ala His Glu Pro Gly Met Asp Gln Asp Lys Asn Pro Met Pro
425                 430                 435

GCT CCT GTT GAA CAT CAG ATC TGT CCT GCT GTG TGT GTT CTA ATG AAA       1398
Ala Pro Val Glu His Gln Ile Cys Pro Ala Val Cys Val Leu Met Lys
440                 445                 450                 455

CTT TCA TTT GAT GAA GAG CAT AGA CAT GCA ATG AAT GAA CTA GGG GGA       1446
Leu Ser Phe Asp Glu Glu His Arg His Ala Met Asn Glu Leu Gly Gly
                460                 465                 470

CTA CAG GCC ATT GCA GAA TTA TTG CAA GTG GAC TGT GAA ATG TAT GGG       1494
Leu Gln Ala Ile Ala Glu Leu Leu Gln Val Asp Cys Glu Met Tyr Gly
        475                 480                 485

CTT ACT AAT GAC CAC TAC AGT ATT ACA CTA AGA CGA TAT GCT GGA ATG       1542
Leu Thr Asn Asp His Tyr Ser Ile Thr Leu Arg Arg Tyr Ala Gly Met
            490                 495                 500

GCT TTG ACA AAC TTG ACT TTT GGA GAT GTA GCC AAC AAG GCT ACG CTA       1590
Ala Leu Thr Asn Leu Thr Phe Gly Asp Val Ala Asn Lys Ala Thr Leu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Ala | Leu | Thr | Asn | Leu | Thr | Phe | Gly | Asp | Val | Ala | Asn | Lys | Ala | Thr | Leu |      |
| 505 |     |     |     |     | 510 |     |     |     |     | 515 |     |     |     |     |     |      |
| TGC | TCT | ATG | AAA | GGC | TGC | ATG | AGA | GCA | CTT | GTG | GCC | CAA | CTA | AAA | TCT | 1638 |
| Cys | Ser | Met | Lys | Gly | Cys | Met | Arg | Ala | Leu | Val | Ala | Gln | Leu | Lys | Ser |      |
| 520 |     |     |     | 525 |     |     |     |     | 530 |     |     |     |     | 535 |     |      |
| GAA | AGT | GAA | GAC | TTA | CAG | CAG | GTT | ATT | GCA | AGT | GTT | TTG | AGG | AAT | TTG | 1686 |
| Glu | Ser | Glu | Asp | Leu | Gln | Gln | Val | Ile | Ala | Ser | Val | Leu | Arg | Asn | Leu |      |
|     |     |     |     | 540 |     |     |     |     | 545 |     |     |     |     | 550 |     |      |
| TCT | TGG | CGA | GCA | GAT | GTA | AAT | AGT | AAA | AAG | ACG | TTG | CGA | GAA | GTT | GGA | 1734 |
| Ser | Trp | Arg | Ala | Asp | Val | Asn | Ser | Lys | Lys | Thr | Leu | Arg | Glu | Val | Gly |      |
|     |     |     | 555 |     |     |     |     | 560 |     |     |     |     | 565 |     |     |      |
| AGT | GTG | AAA | GCA | TTG | ATG | GAA | TGT | GCT | TTA | GAA | GTT | AAA | AAG | GAA | TCA | 1782 |
| Ser | Val | Lys | Ala | Leu | Met | Glu | Cys | Ala | Leu | Glu | Val | Lys | Lys | Glu | Ser |      |
|     |     | 570 |     |     |     |     | 575 |     |     |     |     | 580 |     |     |     |      |
| ACC | CTC | AAA | AGC | GTA | TTG | AGT | GCC | TTA | TGG | AAT | TTG | TCA | GCA | CAT | TGC | 1830 |
| Thr | Leu | Lys | Ser | Val | Leu | Ser | Ala | Leu | Trp | Asn | Leu | Ser | Ala | His | Cys |      |
|     | 585 |     |     |     |     | 590 |     |     |     |     | 595 |     |     |     |     |      |
| ACT | GAG | AAT | AAA | GCT | GAT | ATA | TGT | GCT | GTA | GAT | GGT | GCA | CTT | GCA | TTT | 1878 |
| Thr | Glu | Asn | Lys | Ala | Asp | Ile | Cys | Ala | Val | Asp | Gly | Ala | Leu | Ala | Phe |      |
| 600 |     |     |     |     | 605 |     |     |     |     | 610 |     |     |     |     | 615 |      |
| TTG | GTT | GGC | ACT | CTT | ACT | TAC | CGG | AGC | CAG | ACA | AAC | ACT | TTA | GCC | ATT | 1926 |
| Leu | Val | Gly | Thr | Leu | Thr | Tyr | Arg | Ser | Gln | Thr | Asn | Thr | Leu | Ala | Ile |      |
|     |     |     |     | 620 |     |     |     |     | 625 |     |     |     |     | 630 |     |      |
| ATT | GAA | AGT | GGA | GGT | GGG | ATA | TTA | CGG | AAT | GTG | TCC | AGC | TTG | ATA | GCT | 1974 |
| Ile | Glu | Ser | Gly | Gly | Gly | Ile | Leu | Arg | Asn | Val | Ser | Ser | Leu | Ile | Ala |      |
|     |     |     | 635 |     |     |     |     | 640 |     |     |     |     | 645 |     |     |      |
| ACA | AAT | GAG | GAC | CAC | AGG | CAA | ATC | CTA | AGA | GAG | AAC | AAC | TGT | CTA | CAA | 2022 |
| Thr | Asn | Glu | Asp | His | Arg | Gln | Ile | Leu | Arg | Glu | Asn | Asn | Cys | Leu | Gln |      |
|     |     | 650 |     |     |     |     | 655 |     |     |     |     | 660 |     |     |     |      |
| ACT | TTA | TTA | CAA | CAC | TTA | AAA | TCT | CAT | AGT | TTG | ACA | ATA | GTC | AGT | AAT | 2070 |
| Thr | Leu | Leu | Gln | His | Leu | Lys | Ser | His | Ser | Leu | Thr | Ile | Val | Ser | Asn |      |
| 665 |     |     |     |     | 670 |     |     |     |     | 675 |     |     |     |     |     |      |
| GCA | TGT | GGA | ACT | TTG | TGG | AAT | CTC | TCA | GCA | AGA | AAT | CCT | AAA | GAC | CAG | 2118 |
| Ala | Cys | Gly | Thr | Leu | Trp | Asn | Leu | Ser | Ala | Arg | Asn | Pro | Lys | Asp | Gln |      |
| 680 |     |     |     |     | 685 |     |     |     |     | 690 |     |     |     |     | 695 |      |
| GAA | GCA | TTA | TGG | GAC | ATG | GGG | GCA | GTT | AGC | ATG | CTC | AAG | AAC | CTC | ATT | 2166 |
| Glu | Ala | Leu | Trp | Asp | Met | Gly | Ala | Val | Ser | Met | Leu | Lys | Asn | Leu | Ile |      |
|     |     |     |     | 700 |     |     |     |     | 705 |     |     |     |     | 710 |     |      |
| CAT | TCA | AAG | CAC | AAA | ATG | ATT | GCT | ATG | GGA | AGT | GCT | GCA | GCT | TTA | AGG | 2214 |
| His | Ser | Lys | His | Lys | Met | Ile | Ala | Met | Gly | Ser | Ala | Ala | Ala | Leu | Arg |      |
|     |     |     | 715 |     |     |     |     | 720 |     |     |     |     | 725 |     |     |      |
| AAT | CTC | ATG | GCA | AAT | AGG | CCT | GCG | AAG | TAC | AAG | GAT | GCC | AAT | ATT | ATG | 2262 |
| Asn | Leu | Met | Ala | Asn | Arg | Pro | Ala | Lys | Tyr | Lys | Asp | Ala | Asn | Ile | Met |      |
|     |     | 730 |     |     |     |     | 735 |     |     |     |     | 740 |     |     |     |      |
| TCT | CCT | GGC | TCA | AGC | TTG | CCA | TCT | CTT | CAT | GTT | AGG | AAA | CAA | AAA | GCC | 2310 |
| Ser | Pro | Gly | Ser | Ser | Leu | Pro | Ser | Leu | His | Val | Arg | Lys | Gln | Lys | Ala |      |
|     | 745 |     |     |     |     | 750 |     |     |     |     | 755 |     |     |     |     |      |
| CTA | GAA | GCA | GAA | TTA | GAT | GCT | CAG | CAC | TTA | TCA | GAA | ACT | TTT | GAC | AAT | 2358 |
| Leu | Glu | Ala | Glu | Leu | Asp | Ala | Gln | His | Leu | Ser | Glu | Thr | Phe | Asp | Asn |      |
| 760 |     |     |     |     | 765 |     |     |     |     | 770 |     |     |     |     | 775 |      |
| ATA | GAC | AAT | TTA | AGT | CCC | AAG | GCA | TCT | CAT | CGT | AGT | AAG | CAG | AGA | CAC | 2406 |
| Ile | Asp | Asn | Leu | Ser | Pro | Lys | Ala | Ser | His | Arg | Ser | Lys | Gln | Arg | His |      |
|     |     |     |     | 780 |     |     |     |     | 785 |     |     |     |     | 790 |     |      |
| AAG | CAA | AGT | CTC | TAT | GGT | GAT | TAT | GTT | TTT | GAC | ACC | AAT | CGA | CAT | GAT | 2454 |
| Lys | Gln | Ser | Leu | Tyr | Gly | Asp | Tyr | Val | Phe | Asp | Thr | Asn | Arg | His | Asp |      |
|     |     |     | 795 |     |     |     |     | 800 |     |     |     |     | 805 |     |     |      |
| GAT | AAT | AGG | TCA | GAC | AAT | TTT | AAT | ACT | GGC | AAC | ATG | ACT | GTC | CTT | TCA | 2502 |
| Asp | Asn | Arg | Ser | Asp | Asn | Phe | Asn | Thr | Gly | Asn | Met | Thr | Val | Leu | Ser |      |
|     |     | 810 |     |     |     |     | 815 |     |     |     |     | 820 |     |     |     |      |
| CCA | TAT | TTG | AAT | ACT | ACA | GTG | TTA | CCC | AGC | TCC | TCT | TCA | TCA | AGA | GGA | 2550 |

|  |  |  |  |  |  |  |  |  |  |  |  |  |  |  |  |  |
|---|---|---|---|---|---|---|---|---|---|---|---|---|---|---|---|---|
| Pro | Tyr | Leu | Asn | Thr | Thr | Val | Leu | Pro | Ser | Ser | Ser | Ser | Ser | Arg | Gly | |
| 825 | | | | | 830 | | | | | 835 | | | | | | |

| AGC | TTA | GAT | AGT | TCT | CGT | TCT | GAA | AAA | GAT | AGA | AGT | TTG | GAG | AGA | GAA | 2598 |
|---|---|---|---|---|---|---|---|---|---|---|---|---|---|---|---|---|
| Ser | Leu | Asp | Ser | Ser | Arg | Ser | Glu | Lys | Asp | Arg | Ser | Leu | Glu | Arg | Glu | |
| 840 | | | | | 845 | | | | | 850 | | | | | 855 | |

| CGC | GGA | ATT | GGT | CTA | GGC | AAC | TAC | CAT | CCA | GCA | ACA | GAA | AAT | CCA | GGA | 2646 |
|---|---|---|---|---|---|---|---|---|---|---|---|---|---|---|---|---|
| Arg | Gly | Ile | Gly | Leu | Gly | Asn | Tyr | His | Pro | Ala | Thr | Glu | Asn | Pro | Gly | |
| | | | | | 860 | | | | | 865 | | | | | 870 | |

| ACT | TCT | TCA | AAG | CGA | GGT | TTG | CAG | ATC | TCC | ACC | ACT | GCA | GCC | CAG | ATT | 2694 |
|---|---|---|---|---|---|---|---|---|---|---|---|---|---|---|---|---|
| Thr | Ser | Ser | Lys | Arg | Gly | Leu | Gln | Ile | Ser | Thr | Thr | Ala | Ala | Gln | Ile | |
| | | | 875 | | | | | 880 | | | | | 885 | | | |

| GCC | AAA | GTC | ATG | GAA | GAA | GTG | TCA | GCC | ATT | CAT | ACC | TCT | CAG | GAA | GAC | 2742 |
|---|---|---|---|---|---|---|---|---|---|---|---|---|---|---|---|---|
| Ala | Lys | Val | Met | Glu | Glu | Val | Ser | Ala | Ile | His | Thr | Ser | Gln | Glu | Asp | |
| | | | 890 | | | | | 895 | | | | | 900 | | | |

| AGA | AGT | TCT | GGG | TCT | ACC | ACT | GAA | TTA | CAT | TGT | GTG | ACA | GAT | GAG | AGA | 2790 |
|---|---|---|---|---|---|---|---|---|---|---|---|---|---|---|---|---|
| Arg | Ser | Ser | Gly | Ser | Thr | Thr | Glu | Leu | His | Cys | Val | Thr | Asp | Glu | Arg | |
| 905 | | | | | 910 | | | | | 915 | | | | | | |

| AAT | GCA | CTT | AGA | AGA | AGC | TCT | GCT | GCC | CAT | ACA | CAT | TCA | AAC | ACT | TAC | 2838 |
|---|---|---|---|---|---|---|---|---|---|---|---|---|---|---|---|---|
| Asn | Ala | Leu | Arg | Arg | Ser | Ser | Ala | Ala | His | Thr | His | Ser | Asn | Thr | Tyr | |
| 920 | | | | | 925 | | | | | 930 | | | | | 935 | |

| AAT | TTC | ACT | AAG | TCG | GAA | AAT | TCA | AAT | AGG | ACA | TGT | TCT | ATG | CCT | TAT | 2886 |
|---|---|---|---|---|---|---|---|---|---|---|---|---|---|---|---|---|
| Asn | Phe | Thr | Lys | Ser | Glu | Asn | Ser | Asn | Arg | Thr | Cys | Ser | Met | Pro | Tyr | |
| | | | | 940 | | | | | 945 | | | | | 950 | | |

| GCC | AAA | TTA | GAA | TAC | AAG | AGA | TCT | TCA | AAT | GAT | AGT | TTA | AAT | AGT | GTC | 2934 |
|---|---|---|---|---|---|---|---|---|---|---|---|---|---|---|---|---|
| Ala | Lys | Leu | Glu | Tyr | Lys | Arg | Ser | Ser | Asn | Asp | Ser | Leu | Asn | Ser | Val | |
| | | | 955 | | | | | 960 | | | | | 965 | | | |

| AGT | AGT | AAT | GAT | GGT | TAT | GGT | AAA | AGA | GGT | CAA | ATG | AAA | CCC | TCG | ATT | 2982 |
|---|---|---|---|---|---|---|---|---|---|---|---|---|---|---|---|---|
| Ser | Ser | Asn | Asp | Gly | Tyr | Gly | Lys | Arg | Gly | Gln | Met | Lys | Pro | Ser | Ile | |
| | | 970 | | | | | 975 | | | | | 980 | | | | |

| GAA | TCC | TAT | TCT | GAA | GAT | GAT | GAA | AGT | AAG | TTT | TGC | AGT | TAT | GGT | CAA | 3030 |
|---|---|---|---|---|---|---|---|---|---|---|---|---|---|---|---|---|
| Glu | Ser | Tyr | Ser | Glu | Asp | Asp | Glu | Ser | Lys | Phe | Cys | Ser | Tyr | Gly | Gln | |
| | 985 | | | | | 990 | | | | | 995 | | | | | |

| TAC | CCA | GCC | GAC | CTA | GCC | CAT | AAA | ATA | CAT | AGT | GCA | AAT | CAT | ATG | GAT | 3078 |
|---|---|---|---|---|---|---|---|---|---|---|---|---|---|---|---|---|
| Tyr | Pro | Ala | Asp | Leu | Ala | His | Lys | Ile | His | Ser | Ala | Asn | His | Met | Asp | |
| 1000 | | | | | 1005 | | | | | 1010 | | | | | 1015 | |

| GAT | AAT | GAT | GGA | GAA | CTA | GAT | ACA | CCA | ATA | AAT | TAT | AGT | CTT | AAA | TAT | 3126 |
|---|---|---|---|---|---|---|---|---|---|---|---|---|---|---|---|---|
| Asp | Asn | Asp | Gly | Glu | Leu | Asp | Thr | Pro | Ile | Asn | Tyr | Ser | Leu | Lys | Tyr | |
| | | | | 1020 | | | | | 1025 | | | | | 1030 | | |

| TCA | GAT | GAG | CAG | TTG | AAC | TCT | GGA | AGG | CAA | AGT | CCT | TCA | CAG | AAT | GAA | 3174 |
|---|---|---|---|---|---|---|---|---|---|---|---|---|---|---|---|---|
| Ser | Asp | Glu | Gln | Leu | Asn | Ser | Gly | Arg | Gln | Ser | Pro | Ser | Gln | Asn | Glu | |
| | | | | 1035 | | | | | 1040 | | | | | 1045 | | |

| AGA | TGG | GCA | AGA | CCC | AAA | CAC | ATA | ATA | GAA | GAT | GAA | ATA | AAA | CAA | AGT | 3222 |
|---|---|---|---|---|---|---|---|---|---|---|---|---|---|---|---|---|
| Arg | Trp | Ala | Arg | Pro | Lys | His | Ile | Ile | Glu | Asp | Glu | Ile | Lys | Gln | Ser | |
| | | 1050 | | | | | 1055 | | | | | 1060 | | | | |

| GAG | CAA | AGA | CAA | TCA | AGG | AAT | CAA | AGT | ACA | ACT | TAT | CCT | GTT | TAT | ACT | 3270 |
|---|---|---|---|---|---|---|---|---|---|---|---|---|---|---|---|---|
| Glu | Gln | Arg | Gln | Ser | Arg | Asn | Gln | Ser | Thr | Thr | Tyr | Pro | Val | Tyr | Thr | |
| | | 1065 | | | | | 1070 | | | | | 1075 | | | | |

| GAG | AGC | ACT | GAT | GAT | AAA | CAC | CTC | AAG | TTC | CAA | CCA | CAT | TTT | GGA | CAG | 3318 |
|---|---|---|---|---|---|---|---|---|---|---|---|---|---|---|---|---|
| Glu | Ser | Thr | Asp | Asp | Lys | His | Leu | Lys | Phe | Gln | Pro | His | Phe | Gly | Gln | |
| 1080 | | | | | 1085 | | | | | 1090 | | | | | 1095 | |

| CAG | GAA | TGT | GTT | TCT | CCA | TAC | AGG | TCA | CGG | GGA | GCC | AAT | GGT | TCA | GAA | 3366 |
|---|---|---|---|---|---|---|---|---|---|---|---|---|---|---|---|---|
| Gln | Glu | Cys | Val | Ser | Pro | Tyr | Arg | Ser | Arg | Gly | Ala | Asn | Gly | Ser | Glu | |
| | | | | 1100 | | | | | 1105 | | | | | 1110 | | |

| ACA | AAT | CGA | GTG | GGT | TCT | AAT | CAT | GGA | ATT | AAT | CAA | AAT | GTA | AGC | CAG | 3414 |
|---|---|---|---|---|---|---|---|---|---|---|---|---|---|---|---|---|
| Thr | Asn | Arg | Val | Gly | Ser | Asn | His | Gly | Ile | Asn | Gln | Asn | Val | Ser | Gln | |
| | | | 1115 | | | | | 1120 | | | | | 1125 | | | |

| TCT | TTG | TGT | CAA | GAA | GAT | GAC | TAT | GAA | GAT | GAT | AAG | CCT | ACC | AAT | TAT | 3462 |
|---|---|---|---|---|---|---|---|---|---|---|---|---|---|---|---|---|
| Ser | Leu | Cys | Gln | Glu | Asp | Asp | Tyr | Glu | Asp | Asp | Lys | Pro | Thr | Asn | Tyr | |
| | | 1130 | | | | | 1135 | | | | | 1140 | | | | |

| AGT | GAA | CGT | TAC | TCT | GAA | GAA | GAA | CAG | CAT | GAA | GAA | GAA | GAG | AGA | CCA | 3510 |

```
     Ser Glu Arg Tyr Ser Glu Glu Glu Gln His Glu Glu Glu Arg Pro
         1145                1150                1155

ACA AAT TAT AGC ATA AAA TAT AAT GAA GAG AAA CGT CAT GTG GAT CAG      3558
Thr Asn Tyr Ser Ile Lys Tyr Asn Glu Glu Lys Arg His Val Asp Gln
1160                1165                1170                1175

CCT ATT GAT TAT AGT TTA AAA TAT GCC ACA GAT ATT CCT TCA TCA CAG      3606
Pro Ile Asp Tyr Ser Leu Lys Tyr Ala Thr Asp Ile Pro Ser Ser Gln
                1180                1185                1190

AAA CAG TCA TTT TCA TTC TCA AAG AGT TCA TCT GGA CAA AGC AGT AAA      3654
Lys Gln Ser Phe Ser Phe Ser Lys Ser Ser Ser Gly Gln Ser Ser Lys
            1195                1200                1205

ACC GAA CAT ATG TCT TCA AGC AGT GAG AAT ACG TCC ACA CCT TCA TCT      3702
Thr Glu His Met Ser Ser Ser Ser Glu Asn Thr Ser Thr Pro Ser Ser
1210                1215                1220

AAT GCC AAG AGG CAG AAT CAG CTC CAT CCA AGT TCT GCA CAG AGT AGA      3750
Asn Ala Lys Arg Gln Asn Gln Leu His Pro Ser Ser Ala Gln Ser Arg
1225                1230                1235

AGT GGT CAG CCT CAA AAG GCT GCC ACT TGC AAA GTT TCT TCT ATT AAC      3798
Ser Gly Gln Pro Gln Lys Ala Ala Thr Cys Lys Val Ser Ser Ile Asn
1240                1245                1250                1255

CAA GAA ACA ATA CAG ACT TAT TGT GTA GAA GAT ACT CCA ATA TGT TTT      3846
Gln Glu Thr Ile Gln Thr Tyr Cys Val Glu Asp Thr Pro Ile Cys Phe
                1260                1265                1270

TCA AGA TGT AGT TCA TTA TCA TCT TTG TCA TCA GCT GAA GAT GAA ATA      3894
Ser Arg Cys Ser Ser Leu Ser Ser Leu Ser Ser Ala Glu Asp Glu Ile
            1275                1280                1285

GGA TGT AAT CAG ACG ACA CAG GAA GCA GAT TCT GCT AAT ACC CTG CAA      3942
Gly Cys Asn Gln Thr Thr Gln Glu Ala Asp Ser Ala Asn Thr Leu Gln
        1290                1295                1300

ATA GCA GAA ATA AAA GGA AAG ATT GGA ACT AGG TCA GCT GAA GAT CCT      3990
Ile Ala Glu Ile Lys Gly Lys Ile Gly Thr Arg Ser Ala Glu Asp Pro
1305                1310                1315

GTG AGC GAA GTT CCA GCA GTG TCA CAG CAC CCT AGA ACC AAA TCC AGC      4038
Val Ser Glu Val Pro Ala Val Ser Gln His Pro Arg Thr Lys Ser Ser
1320                1325                1330                1335

AGA CTG CAG GGT TCT AGT TTA TCT TCA GAA TCA GCC AGG CAC AAA GCT      4086
Arg Leu Gln Gly Ser Ser Leu Ser Ser Glu Ser Ala Arg His Lys Ala
                1340                1345                1350

GTT GAA TTT CCT TCA GGA GCG AAA TCT CCC TCC AAA AGT GGT GCT CAG      4134
Val Glu Phe Pro Ser Gly Ala Lys Ser Pro Ser Lys Ser Gly Ala Gln
            1355                1360                1365

ACA CCC AAA AGT CCA CCT GAA CAC TAT GTT CAG GAG ACC CCA CTC ATG      4182
Thr Pro Lys Ser Pro Pro Glu His Tyr Val Gln Glu Thr Pro Leu Met
        1370                1375                1380

TTT AGC AGA TGT ACT TCT GTC AGT TCA CTT GAT AGT TTT GAG AGT CGT      4230
Phe Ser Arg Cys Thr Ser Val Ser Ser Leu Asp Ser Phe Glu Ser Arg
1385                1390                1395

TCG ATT GCC AGC TCC GTT CAG AGT GAA CCA TGC AGT GGA ATG GTA AGT      4278
Ser Ile Ala Ser Ser Val Gln Ser Glu Pro Cys Ser Gly Met Val Ser
1400                1405                1410                1415

GGC ATT ATA AGC CCC AGT GAT CTT CCA GAT AGC CCT GGA CAA ACC ATG      4326
Gly Ile Ile Ser Pro Ser Asp Leu Pro Asp Ser Pro Gly Gln Thr Met
                1420                1425                1430

CCA CCA AGC AGA AGT AAA ACA CCT CCA CCA CCT CCT CAA ACA GCT CAA      4374
Pro Pro Ser Arg Ser Lys Thr Pro Pro Pro Pro Pro Gln Thr Ala Gln
            1435                1440                1445

ACC AAG CGA GAA GTA CCT AAA AAT AAA GCA CCT ACT GCT GAA AAG AGA      4422
Thr Lys Arg Glu Val Pro Lys Asn Lys Ala Pro Thr Ala Glu Lys Arg
        1450                1455                1460

GAG AGT GGA CCT AAG CAA GCT GCA GTA AAT GCT GCA GTT CAG AGG GTC      4470
```

|  |  |  |  |  |  |  |  |  |  |  |  |  |  |  |  |
|---|---|---|---|---|---|---|---|---|---|---|---|---|---|---|---|
| Glu | Ser | Gly | Pro | Lys | Gln | Ala | Val | Asn | Ala | Ala | Val | Gln | Arg | Val |  |
| 1465 |  |  |  | 1470 |  |  |  |  | 1475 |  |  |  |  |  |  |

| CAG | GTT | CTT | CCA | GAT | GCT | GAT | ACT | TTA | TTA | CAT | TTT | GCC | ACA | GAA | AGT | 4518 |
|---|---|---|---|---|---|---|---|---|---|---|---|---|---|---|---|---|
| Gln | Val | Leu | Pro | Asp | Ala | Asp | Thr | Leu | Leu | His | Phe | Ala | Thr | Glu | Ser |  |
| 1480 |  |  |  |  | 1485 |  |  |  |  | 1490 |  |  |  |  | 1495 |  |

| ACT | CCA | GAT | GGA | TTT | TCT | TGT | TCA | TCC | AGC | CTG | AGT | GCT | CTG | AGC | CTC | 4566 |
|---|---|---|---|---|---|---|---|---|---|---|---|---|---|---|---|---|
| Thr | Pro | Asp | Gly | Phe | Ser | Cys | Ser | Ser | Ser | Leu | Ser | Ala | Leu | Ser | Leu |  |
|  |  |  |  | 1500 |  |  |  |  | 1505 |  |  |  |  | 1510 |  |  |

| GAT | GAG | CCA | TTT | ATA | CAG | AAA | GAT | GTG | GAA | TTA | AGA | ATA | ATG | CCT | CCA | 4614 |
|---|---|---|---|---|---|---|---|---|---|---|---|---|---|---|---|---|
| Asp | Glu | Pro | Phe | Ile | Gln | Lys | Asp | Val | Glu | Leu | Arg | Ile | Met | Pro | Pro |  |
|  |  |  | 1515 |  |  |  |  | 1520 |  |  |  |  | 1525 |  |  |  |

| GTT | CAG | GAA | AAT | GAC | AAT | GGG | AAT | GAA | ACA | GAA | TCA | GAG | CAG | CCT | AAA | 4662 |
|---|---|---|---|---|---|---|---|---|---|---|---|---|---|---|---|---|
| Val | Gln | Glu | Asn | Asp | Asn | Gly | Asn | Glu | Thr | Glu | Ser | Glu | Gln | Pro | Lys |  |
|  |  | 1530 |  |  |  |  | 1535 |  |  |  |  | 1540 |  |  |  |  |

| GAA | TCA | AAT | GAA | AAC | CAA | GAG | AAA | GAG | GCA | GAA | AAA | ACT | ATT | GAT | TCT | 4710 |
|---|---|---|---|---|---|---|---|---|---|---|---|---|---|---|---|---|
| Glu | Ser | Asn | Glu | Asn | Gln | Glu | Lys | Glu | Ala | Glu | Lys | Thr | Ile | Asp | Ser |  |
| 1545 |  |  |  |  | 1550 |  |  |  |  | 1555 |  |  |  |  |  |  |

| GAA | AAG | GAC | CTA | TTA | GAT | GAT | TCA | GAT | GAT | GAT | GAT | ATT | GAA | ATA | CTA | 4758 |
|---|---|---|---|---|---|---|---|---|---|---|---|---|---|---|---|---|
| Glu | Lys | Asp | Leu | Leu | Asp | Asp | Ser | Asp | Asp | Asp | Asp | Ile | Glu | Ile | Leu |  |
| 1560 |  |  |  |  | 1565 |  |  |  |  | 1570 |  |  |  |  | 1575 |  |

| GAA | GAA | TGT | ATT | ATT | TCT | GCC | ATG | CCA | ACA | AAG | TCA | TCA | CGT | AAA | GGC | 4806 |
|---|---|---|---|---|---|---|---|---|---|---|---|---|---|---|---|---|
| Glu | Glu | Cys | Ile | Ile | Ser | Ala | Met | Pro | Thr | Lys | Ser | Ser | Arg | Lys | Gly |  |
|  |  |  |  | 1580 |  |  |  |  | 1585 |  |  |  |  | 1590 |  |  |

| AAA | AAG | CCA | GCC | CAG | ACT | GCT | TCA | AAA | TTA | CCT | CCA | CCT | GTG | GCA | AGG | 4854 |
|---|---|---|---|---|---|---|---|---|---|---|---|---|---|---|---|---|
| Lys | Lys | Pro | Ala | Gln | Thr | Ala | Ser | Lys | Leu | Pro | Pro | Pro | Val | Ala | Arg |  |
|  |  |  |  | 1595 |  |  |  |  | 1600 |  |  |  |  | 1605 |  |  |

| AAA | CCA | AGT | CAG | CTG | CCT | GTG | TAC | AAA | CTT | CTA | CCA | TCA | CAA | AAC | AGG | 4902 |
|---|---|---|---|---|---|---|---|---|---|---|---|---|---|---|---|---|
| Lys | Pro | Ser | Gln | Leu | Pro | Val | Tyr | Lys | Leu | Leu | Pro | Ser | Gln | Asn | Arg |  |
|  |  |  | 1610 |  |  |  |  | 1615 |  |  |  |  | 1620 |  |  |  |

| TTG | CAA | CCC | CAA | AAG | CAT | GTT | AGT | TTT | ACA | CCG | GGG | GAT | GAT | ATG | CCA | 4950 |
|---|---|---|---|---|---|---|---|---|---|---|---|---|---|---|---|---|
| Leu | Gln | Pro | Gln | Lys | His | Val | Ser | Phe | Thr | Pro | Gly | Asp | Asp | Met | Pro |  |
|  |  | 1625 |  |  |  |  | 1630 |  |  |  |  | 1635 |  |  |  |  |

| CGG | GTG | TAT | TGT | GTT | GAA | GGG | ACA | CCT | ATA | AAC | TTT | TCC | ACA | GCT | ACA | 4998 |
|---|---|---|---|---|---|---|---|---|---|---|---|---|---|---|---|---|
| Arg | Val | Tyr | Cys | Val | Glu | Gly | Thr | Pro | Ile | Asn | Phe | Ser | Thr | Ala | Thr |  |
| 1640 |  |  |  |  | 1645 |  |  |  |  | 1650 |  |  |  |  | 1655 |  |

| TCT | CTA | AGT | GAT | CTA | ACA | ATC | GAA | TCC | CCT | CCA | AAT | GAG | TTA | GCT | GCT | 5046 |
|---|---|---|---|---|---|---|---|---|---|---|---|---|---|---|---|---|
| Ser | Leu | Ser | Asp | Leu | Thr | Ile | Glu | Ser | Pro | Pro | Asn | Glu | Leu | Ala | Ala |  |
|  |  |  |  | 1660 |  |  |  |  | 1665 |  |  |  |  | 1670 |  |  |

| GGA | GAA | GGA | GTT | AGA | GGA | GGA | GCA | CAG | TCA | GGT | GAA | TTT | GAA | AAA | CGA | 5094 |
|---|---|---|---|---|---|---|---|---|---|---|---|---|---|---|---|---|
| Gly | Glu | Gly | Val | Arg | Gly | Gly | Ala | Gln | Ser | Gly | Glu | Phe | Glu | Lys | Arg |  |
|  |  |  | 1675 |  |  |  |  | 1680 |  |  |  |  | 1685 |  |  |  |

| GAT | ACC | ATT | CCT | ACA | GAA | GGC | AGA | AGT | ACA | GAT | GAG | GCT | CAA | GGA | GGA | 5142 |
|---|---|---|---|---|---|---|---|---|---|---|---|---|---|---|---|---|
| Asp | Thr | Ile | Pro | Thr | Glu | Gly | Arg | Ser | Thr | Asp | Glu | Ala | Gln | Gly | Gly |  |
|  |  | 1690 |  |  |  |  | 1695 |  |  |  |  | 1700 |  |  |  |  |

| AAA | ACC | TCA | TCT | GTA | ACC | ATA | CCT | GAA | TTG | GAT | GAC | AAT | AAA | GCA | GAG | 5190 |
|---|---|---|---|---|---|---|---|---|---|---|---|---|---|---|---|---|
| Lys | Thr | Ser | Ser | Val | Thr | Ile | Pro | Glu | Leu | Asp | Asp | Asn | Lys | Ala | Glu |  |
| 1705 |  |  |  |  | 1710 |  |  |  |  | 1715 |  |  |  |  |  |  |

| GAA | GGT | GAT | ATT | CTT | GCA | GAA | TGC | ATT | AAT | TCT | GCT | ATG | CCC | AAA | GGG | 5238 |
|---|---|---|---|---|---|---|---|---|---|---|---|---|---|---|---|---|
| Glu | Gly | Asp | Ile | Leu | Ala | Glu | Cys | Ile | Asn | Ser | Ala | Met | Pro | Lys | Gly |  |
| 1720 |  |  |  |  | 1725 |  |  |  |  | 1730 |  |  |  |  | 1735 |  |

| AAA | AGT | CAC | AAG | CCT | TTC | CGT | GTG | AAA | AAG | ATA | ATG | GAC | CAG | GTC | CAG | 5286 |
|---|---|---|---|---|---|---|---|---|---|---|---|---|---|---|---|---|
| Lys | Ser | His | Lys | Pro | Phe | Arg | Val | Lys | Lys | Ile | Met | Asp | Gln | Val | Gln |  |
|  |  |  |  | 1740 |  |  |  |  | 1745 |  |  |  |  | 1750 |  |  |

| CAA | GCA | TCT | GCG | TCG | TCT | TCT | GCA | CCC | AAC | AAA | AAT | CAG | TTA | GAT | GGT | 5334 |
|---|---|---|---|---|---|---|---|---|---|---|---|---|---|---|---|---|
| Gln | Ala | Ser | Ala | Ser | Ser | Ser | Ala | Pro | Asn | Lys | Asn | Gln | Leu | Asp | Gly |  |
|  |  | 1755 |  |  |  |  | 1760 |  |  |  |  | 1765 |  |  |  |  |

| AAG | AAA | AAG | AAA | CCA | ACT | TCA | CCA | GTA | AAA | CCT | ATA | CCA | CAA | AAT | ACT | 5382 |
|---|---|---|---|---|---|---|---|---|---|---|---|---|---|---|---|---|
| Lys | Lys | Lys | Lys | Pro | Thr | Ser | Pro | Val | Lys | Pro | Ile | Pro | Gln | Asn | Thr |  |
|  |  | 1770 |  |  |  |  | 1775 |  |  |  |  | 1780 |  |  |  |  |

| GAA | TAT | AGG | ACA | CGT | GTA | AGA | AAA | AAT | GCA | GAC | TCA | AAA | AAT | AAT | TTA | 5430 |

-continued

```
                Glu Tyr Arg Thr Arg Val Arg Lys Asn Ala Asp Ser Lys Asn Asn Leu
                1785                1790                1795

AAT GCT GAG AGA GTT TTC TCA GAC AAC AAA GAT TCA AAG AAA CAG AAT            5478
Asn Ala Glu Arg Val Phe Ser Asp Asn Lys Asp Ser Lys Lys Gln Asn
1800                1805                1810                1815

TTG AAA AAT AAT TCC AAG GAC TTC AAT GAT AAG CTC CCA AAT AAT GAA            5526
Leu Lys Asn Asn Ser Lys Asp Phe Asn Asp Lys Leu Pro Asn Asn Glu
            1820                1825                1830

GAT AGA GTC AGA GGA AGT TTT GCT TTT GAT TCA CCT CAT CAT TAC ACG            5574
Asp Arg Val Arg Gly Ser Phe Ala Phe Asp Ser Pro His His Tyr Thr
            1835                1840                1845

CCT ATT GAA GGA ACT CCT TAC TGT TTT TCA CGA AAT GAT TCT TTG AGT            5622
Pro Ile Glu Gly Thr Pro Tyr Cys Phe Ser Arg Asn Asp Ser Leu Ser
            1850                1855                1860

TCT CTA GAT TTT GAT GAT GAT GAT GTT GAC CTT TCC AGG GAA AAG GCT            5670
Ser Leu Asp Phe Asp Asp Asp Asp Val Asp Leu Ser Arg Glu Lys Ala
            1865                1870                1875

GAA TTA AGA AAG GCA AAA GAA AAT AAG GAA TCA GAG GCT AAA GTT ACC            5718
Glu Leu Arg Lys Ala Lys Glu Asn Lys Glu Ser Glu Ala Lys Val Thr
1880                1885                1890                1895

AGC CAC ACA GAA CTA ACC TCC AAC CAA CAA TCA GCT AAT AAG ACA CAA            5766
Ser His Thr Glu Leu Thr Ser Asn Gln Gln Ser Ala Asn Lys Thr Gln
            1900                1905                1910

GCT ATT GCA AAG CAG CCA ATA AAT CGA GGT CAG CCT AAA CCC ATA CTT            5814
Ala Ile Ala Lys Gln Pro Ile Asn Arg Gly Gln Pro Lys Pro Ile Leu
            1915                1920                1925

CAG AAA CAA TCC ACT TTT CCC CAG TCA TCC AAA GAC ATA CCA GAC AGA            5862
Gln Lys Gln Ser Thr Phe Pro Gln Ser Ser Lys Asp Ile Pro Asp Arg
            1930                1935                1940

GGG GCA GCA ACT GAT GAA AAG TTA CAG AAT TTT GCT ATT GAA AAT ACT            5910
Gly Ala Ala Thr Asp Glu Lys Leu Gln Asn Phe Ala Ile Glu Asn Thr
            1945                1950                1955

CCA GTT TGC TTT TCT CAT AAT TCC TCT CTG AGT TCT CTC AGT GAC ATT            5958
Pro Val Cys Phe Ser His Asn Ser Ser Leu Ser Ser Leu Ser Asp Ile
1960                1965                1970                1975

GAC CAA GAA AAC AAC AAT AAA GAA AAT GAA CCT ATC AAA GAG ACT GAG            6006
Asp Gln Glu Asn Asn Asn Lys Glu Asn Glu Pro Ile Lys Glu Thr Glu
            1980                1985                1990

CCC CCT GAC TCA CAG GGA GAA CCA AGT AAA CCT CAA GCA TCA GGC TAT            6054
Pro Pro Asp Ser Gln Gly Glu Pro Ser Lys Pro Gln Ala Ser Gly Tyr
            1995                2000                2005

GCT CCT AAA TCA TTT CAT GTT GAA GAT ACC CCA GTT TGT TTC TCA AGA            6102
Ala Pro Lys Ser Phe His Val Glu Asp Thr Pro Val Cys Phe Ser Arg
            2010                2015                2020

AAC AGT TCT CTC AGT TCT CTT AGT ATT GAC TCT GAA GAT GAC CTG TTG            6150
Asn Ser Ser Leu Ser Ser Leu Ser Ile Asp Ser Glu Asp Asp Leu Leu
            2025                2030                2035

CAG GAA TGT ATA AGC TCC GCA ATG CCA AAA AAG AAA AAG CCT TCA AGA            6198
Gln Glu Cys Ile Ser Ser Ala Met Pro Lys Lys Lys Lys Pro Ser Arg
2040                2045                2050                2055

CTC AAG GGT GAT AAT GAA AAA CAT AGT CCC AGA AAT ATG GGT GGC ATA            6246
Leu Lys Gly Asp Asn Glu Lys His Ser Pro Arg Asn Met Gly Gly Ile
            2060                2065                2070

TTA GGT GAA GAT CTG ACA CTT GAT TTG AAA GAT ATA CAG AGA CCA GAT            6294
Leu Gly Glu Asp Leu Thr Leu Asp Leu Lys Asp Ile Gln Arg Pro Asp
            2075                2080                2085

TCA GAA CAT GGT CTA TCC CCT GAT TCA GAA AAT TTT GAT TGG AAA GCT            6342
Ser Glu His Gly Leu Ser Pro Asp Ser Glu Asn Phe Asp Trp Lys Ala
            2090                2095                2100

ATT CAG GAA GGT GCA AAT TCC ATA GTA AGT AGT TTA CAT CAA GCT GCT            6390
```

-continued

```
            Ile Gln Glu Gly Ala Asn Ser Ile Val Ser Ser Leu His Gln Ala Ala
            2105                2110                2115

GCT GCT GCA TGT TTA TCT AGA CAA GCT TCG TCT GAT TCA GAT TCC ATC        6438
Ala Ala Ala Cys Leu Ser Arg Gln Ala Ser Ser Asp Ser Asp Ser Ile
2120                2125                2130                2135

CTT TCC CTG AAA TCA GGA ATC TCT CTG GGA TCA CCA TTT CAT CTT ACA        6486
Leu Ser Leu Lys Ser Gly Ile Ser Leu Gly Ser Pro Phe His Leu Thr
                2140                2145                2150

CCT GAT CAA GAA GAA AAA CCC TTT ACA AGT AAT AAA GGC CCA CGA ATT        6534
Pro Asp Gln Glu Glu Lys Pro Phe Thr Ser Asn Lys Gly Pro Arg Ile
            2155                2160                2165

CTA AAA CCA GGG GAG AAA AGT ACA TTG GAA ACT AAA AAG ATA GAA TCT        6582
Leu Lys Pro Gly Glu Lys Ser Thr Leu Glu Thr Lys Lys Ile Glu Ser
        2170                2175                2180

GAA AGT AAA GGA ATC AAA GGA GGA AAA AAA GTT TAT AAA AGT TTG ATT        6630
Glu Ser Lys Gly Ile Lys Gly Gly Lys Lys Val Tyr Lys Ser Leu Ile
    2185                2190                2195

ACT GGA AAA GTT CGA TCT AAT TCA GAA ATT TCA GGC CAA ATG AAA CAG        6678
Thr Gly Lys Val Arg Ser Asn Ser Glu Ile Ser Gly Gln Met Lys Gln
2200                2205                2210                2215

CCC CTT CAA GCA AAC ATG CCT TCA ATC TCT CGA GGC AGG ACA ATG ATT        6726
Pro Leu Gln Ala Asn Met Pro Ser Ile Ser Arg Gly Arg Thr Met Ile
                2220                2225                2230

CAT ATT CCA GGA GTT CGA AAT AGC TCC TCA AGT ACA AGT CCT GTT TCT        6774
His Ile Pro Gly Val Arg Asn Ser Ser Ser Ser Thr Ser Pro Val Ser
            2235                2240                2245

AAA AAA GGC CCA CCC CTT AAG ACT CCA GCC TCC AAA AGC CCT AGT GAA        6822
Lys Lys Gly Pro Pro Leu Lys Thr Pro Ala Ser Lys Ser Pro Ser Glu
        2250                2255                2260

GGT CAA ACA GCC ACC ACT TCT CCT AGA GGA GCC AAG CCA TCT GTG AAA        6870
Gly Gln Thr Ala Thr Thr Ser Pro Arg Gly Ala Lys Pro Ser Val Lys
    2265                2270                2275

TCA GAA TTA AGC CCT GTT GCC AGG CAG ACA TCC CAA ATA GGT GGG TCA        6918
Ser Glu Leu Ser Pro Val Ala Arg Gln Thr Ser Gln Ile Gly Gly Ser
2280                2285                2290                2295

AGT AAA GCA CCT TCT AGA TCA GGA TCT AGA GAT TCG ACC CCT TCA AGA        6966
Ser Lys Ala Pro Ser Arg Ser Gly Ser Arg Asp Ser Thr Pro Ser Arg
                2300                2305                2310

CCT GCC CAG CAA CCA TTA AGT AGA CCT ATA CAG TCT CCT GGC CGA AAC        7014
Pro Ala Gln Gln Pro Leu Ser Arg Pro Ile Gln Ser Pro Gly Arg Asn
            2315                2320                2325

TCA ATT TCC CCT GGT AGA AAT GGA ATA AGT CCT CCT AAC AAA TTA TCT        7062
Ser Ile Ser Pro Gly Arg Asn Gly Ile Ser Pro Pro Asn Lys Leu Ser
        2330                2335                2340

CAA CTT CCA AGG ACA TCA TCC CCT AGT ACT GCT TCA ACT AAG TCC TCA        7110
Gln Leu Pro Arg Thr Ser Ser Pro Ser Thr Ala Ser Thr Lys Ser Ser
    2345                2350                2355

GGT TCT GGA AAA ATG TCA TAT ACA TCT CCA GGT AGA CAG ATG AGC CAA        7158
Gly Ser Gly Lys Met Ser Tyr Thr Ser Pro Gly Arg Gln Met Ser Gln
2360                2365                2370                2375

CAG AAC CTT ACC AAA CAA ACA GGT TTA TCC AAG AAT GCC AGT AGT ATT        7206
Gln Asn Leu Thr Lys Gln Thr Gly Leu Ser Lys Asn Ala Ser Ser Ile
                2380                2385                2390

CCA AGA AGT GAG TCT GCC TCC AAA GGA CTA AAT CAG ATG AAT AAT GGT        7254
Pro Arg Ser Glu Ser Ala Ser Lys Gly Leu Asn Gln Met Asn Asn Gly
            2395                2400                2405

AAT GGA GCC AAT AAA AAG GTA GAA CTT TCT AGA ATG TCT TCA ACT AAA        7302
Asn Gly Ala Asn Lys Lys Val Glu Leu Ser Arg Met Ser Ser Thr Lys
        2410                2415                2420

TCA AGT GGA AGT GAA TCT GAT AGA TCA GAA AGA CCT GTA TTA GTA CGC        7350
```

```
Ser  Ser  Gly  Ser  Glu  Ser  Asp  Arg  Ser  Glu  Arg  Pro  Val  Leu  Val  Arg
     2425                     2430                     2435

CAG  TCA  ACT  TTC  ATC  AAA  GAA  GCT  CCA  AGC  CCA  ACC  TTA  AGA  AGA  AAA       7398
Gln  Ser  Thr  Phe  Ile  Lys  Glu  Ala  Pro  Ser  Pro  Thr  Leu  Arg  Arg  Lys
2440                     2445                     2450                     2455

TTG  GAG  GAA  TCT  GCT  TCA  TTT  GAA  TCT  CTT  TCT  CCA  TCA  TCT  AGA  CCA       7446
Leu  Glu  Glu  Ser  Ala  Ser  Phe  Glu  Ser  Leu  Ser  Pro  Ser  Ser  Arg  Pro
                         2460                     2465                     2470

GCT  TCT  CCC  ACT  AGG  TCC  CAG  GCA  CAA  ACT  CCA  GTT  TTA  AGT  CCT  TCC       7494
Ala  Ser  Pro  Thr  Arg  Ser  Gln  Ala  Gln  Thr  Pro  Val  Leu  Ser  Pro  Ser
                    2475                     2480                     2485

CTT  CCT  GAT  ATG  TCT  CTA  TCC  ACA  CAT  TCG  TCT  GTT  CAG  GCT  GGT  GGA       7542
Leu  Pro  Asp  Met  Ser  Leu  Ser  Thr  His  Ser  Ser  Val  Gln  Ala  Gly  Gly
          2490                     2495                     2500

TGG  CGA  AAA  CTC  CCA  CCT  AAT  CTC  AGT  CCC  ACT  ATA  GAG  TAT  AAT  GAT       7590
Trp  Arg  Lys  Leu  Pro  Pro  Asn  Leu  Ser  Pro  Thr  Ile  Glu  Tyr  Asn  Asp
     2505                     2510                     2515

GGA  AGA  CCA  GCA  AAG  CGC  CAT  GAT  ATT  GCA  CGG  TCT  CAT  TCT  GAA  AGT       7638
Gly  Arg  Pro  Ala  Lys  Arg  His  Asp  Ile  Ala  Arg  Ser  His  Ser  Glu  Ser
2520                     2525                     2530                     2535

CCT  TCT  AGA  CTT  CCA  ATC  AAT  AGG  TCA  GGA  ACC  TGG  AAA  CGT  GAG  CAC       7686
Pro  Ser  Arg  Leu  Pro  Ile  Asn  Arg  Ser  Gly  Thr  Trp  Lys  Arg  Glu  His
                    2540                     2545                     2550

AGC  AAA  CAT  TCA  TCA  TCC  CTT  CCT  CGA  GTA  AGC  ACT  TGG  AGA  AGA  ACT       7734
Ser  Lys  His  Ser  Ser  Ser  Leu  Pro  Arg  Val  Ser  Thr  Trp  Arg  Arg  Thr
                    2555                     2560                     2565

GGA  AGT  TCA  TCT  TCA  ATT  CTT  TCT  GCT  TCA  TCA  GAA  TCC  AGT  GAA  AAA       7782
Gly  Ser  Ser  Ser  Ser  Ile  Leu  Ser  Ala  Ser  Ser  Glu  Ser  Ser  Glu  Lys
                    2570                     2575                     2580

GCA  AAA  AGT  GAG  GAT  GAA  AAA  CAT  GTG  AAC  TCT  ATT  TCA  GGA  ACC  AAA       7830
Ala  Lys  Ser  Glu  Asp  Glu  Lys  His  Val  Asn  Ser  Ile  Ser  Gly  Thr  Lys
     2585                     2590                     2595

CAA  AGT  AAA  GAA  AAC  CAA  GTA  TCC  GCA  AAA  GGA  ACA  TGG  AGA  AAA  ATA       7878
Gln  Ser  Lys  Glu  Asn  Gln  Val  Ser  Ala  Lys  Gly  Thr  Trp  Arg  Lys  Ile
2600                     2605                     2610                     2615

AAA  GAA  AAT  GAA  TTT  TCT  CCC  ACA  AAT  AGT  ACT  TCT  CAG  ACC  GTT  TCC       7926
Lys  Glu  Asn  Glu  Phe  Ser  Pro  Thr  Asn  Ser  Thr  Ser  Gln  Thr  Val  Ser
                         2620                     2625                     2630

TCA  GGT  GCT  ACA  AAT  GGT  GCT  GAA  TCA  AAG  ACT  CTA  ATT  TAT  CAA  ATG       7974
Ser  Gly  Ala  Thr  Asn  Gly  Ala  Glu  Ser  Lys  Thr  Leu  Ile  Tyr  Gln  Met
                         2635                     2640                     2645

GCA  CCT  GCT  GTT  TCT  AAA  ACA  GAG  GAT  GTT  TGG  GTG  AGA  ATT  GAG  GAC       8022
Ala  Pro  Ala  Val  Ser  Lys  Thr  Glu  Asp  Val  Trp  Val  Arg  Ile  Glu  Asp
                    2650                     2655                     2660

TGT  CCC  ATT  AAC  AAT  CCT  AGA  TCT  GGA  AGA  TCT  CCC  ACA  GGT  AAT  ACT       8070
Cys  Pro  Ile  Asn  Asn  Pro  Arg  Ser  Gly  Arg  Ser  Pro  Thr  Gly  Asn  Thr
                    2665                     2670                     2675

CCC  CCG  GTG  ATT  GAC  AGT  GTT  TCA  GAA  AAG  GCA  AAT  CCA  AAC  ATT  AAA       8118
Pro  Pro  Val  Ile  Asp  Ser  Val  Ser  Glu  Lys  Ala  Asn  Pro  Asn  Ile  Lys
2680                     2685                     2690                     2695

GAT  TCA  AAA  GAT  AAT  CAG  GCA  AAA  CAA  AAT  GTG  GGT  AAT  GGC  AGT  GTT       8166
Asp  Ser  Lys  Asp  Asn  Gln  Ala  Lys  Gln  Asn  Val  Gly  Asn  Gly  Ser  Val
                    2700                     2705                     2710

CCC  ATG  CGT  ACC  GTG  GGT  TTG  GAA  AAT  CGC  CTG  ACC  TCC  TTT  ATT  CAG       8214
Pro  Met  Arg  Thr  Val  Gly  Leu  Glu  Asn  Arg  Leu  Thr  Ser  Phe  Ile  Gln
               2715                     2720                     2725

GTG  GAT  GCC  CCT  GAC  CAA  AAA  GGA  ACT  GAG  ATA  AAA  CCA  GGA  CAA  AAT       8262
Val  Asp  Ala  Pro  Asp  Gln  Lys  Gly  Thr  Glu  Ile  Lys  Pro  Gly  Gln  Asn
          2730                     2735                     2740

AAT  CCT  GTC  CCT  GTA  TCA  GAG  ACT  AAT  GAA  AGT  CCT  ATA  GTG  GAA  CGT       8310
```

| | | | | | | | | | | | | | | |
|---|---|---|---|---|---|---|---|---|---|---|---|---|---|---|
| Asn | Pro | Val | Pro | Val | Ser | Glu | Thr | Asn | Glu | Ser | Pro | Ile | Val | Glu | Arg |
| | 2745 | | | | 2750 | | | | | 2755 | | | | |

```
ACC CCA TTC AGT TCT AGC AGC TCA AGC AAA CAC AGT TCA CCT AGT GGG         8358
Thr Pro Phe Ser Ser Ser Ser Ser Ser Lys His Ser Ser Pro Ser Gly
2760                2765                2770                2775

ACT GTT GCT GCC AGA GTG ACT CCT TTT AAT TAC AAC CCA AGC CCT AGG         8406
Thr Val Ala Ala Arg Val Thr Pro Phe Asn Tyr Asn Pro Ser Pro Arg
                2780                2785                2790

AAA AGC AGC GCA GAT AGC ACT TCA GCT CGG CCA TCT CAG ATC CCA ACT         8454
Lys Ser Ser Ala Asp Ser Thr Ser Ala Arg Pro Ser Gln Ile Pro Thr
            2795                2800                2805

CCA GTG AAT AAC AAC ACA AAG AAG CGA GAT TCC AAA ACT GAC AGC ACA         8502
Pro Val Asn Asn Asn Thr Lys Lys Arg Asp Ser Lys Thr Asp Ser Thr
        2810                2815                2820

GAA TCC AGT GGA ACC CAA AGT CCT AAG CGC CAT TCT GGG TCT TAC CTT         8550
Glu Ser Ser Gly Thr Gln Ser Pro Lys Arg His Ser Gly Ser Tyr Leu
    2825                2830                2835

GTG ACA TCT GTT TAAAAGAGAG GAAGAATGAA ACTAAGAAAA TTCTATGTTA             8602
Val Thr Ser Val
2840

ATTACAACTG CTATATAGAC ATTTTGTTTC AAATGAAACT TTAAAAGACT GAAAAATTTT       8662
GTAAATAGGT TTGATTCTTG TTAGAGGGTT TTTGTTCTGG AAGCCATATT TGATAGTATA       8722
CTTTGTCTTC ACTGGTCTTA TTTTGGGAGG CACTCTTGAT GGTTAGGAAA AAATAGAAAG       8782
CCAAGTATGT TTGTACAGTA TGTTTACAT GTATTTAAAG TAGCATCCCA TCCCAACTTC        8842
CTTAATTATT GCTTGTCTAA AATAATGAAC ACTACAGATA GGAAATATGA TATATTGCTG       8902
TTATCAATCA TTTCTAGATT ATAAACTGAC TAAACTTACA TCAGGGAAA ATTGGTATTT        8962
ATGCAAAAAA AAAATGTTTT TGTCCTTGTG AGTCCATCTA ACATCATAAT TAATCATGTG       9022
GCTGTGAAAT TCACAGTAAT ATGGTTCCCG ATGAACAAGT TTACCCAGCC TGCTTTGCTT       9082
ACTGCATGAA TGAAACTGAT GGTTCAATTT CAGAAGTAAT GATTAACAGT TATGTGGTCA       9142
CATGATGTGC ATAGAGATAG CTACAGTGTA ATAATTTACA CTATTTGTG CTCCAAACAA        9202
AACAAAAATC TGTGTAACTG TAAAACATTG AATGAAACTA TTTTACCTGA ACTAGATTTT       9262
ATCTGAAAGT AGGTAGAATT TTGCTATGC TGTAATTTGT TGTATATTCT GGTATTTGAG        9322
GTGAGATGGC TGCTCTTTAT TAATGAGACA TGAATTGTGT CTCAACAGAA ACTAAATGAA       9382
CATTTCAGAA TAAATTATTG CTGTATGTAA ACTGTTACTG AAATTGGTAT TTGTTTGAAG       9442
GGTTTGTTTC ACATTTGTAT TAATTAATTG TTTAAAATGC CTCTTTTAAA AGCTTATATA      9502
AATTTTTTCT TCAGCTTCTA TGCATTAAGA GTAAAATTCC TCTTACTGTA ATAAAAACAT       9562
TGAAGAAGAC TGTTGCCACT TAACCATTCC ATGCGTTGGC ACTT                       9606
```

( 2 ) INFORMATION FOR SEQ ID NO:2:

( i ) SEQUENCE CHARACTERISTICS:
    ( A ) LENGTH: 2843 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ala | Ala | Ala | Ser | Tyr | Asp | Gln | Leu | Leu | Lys | Gln | Val | Glu | Ala | Leu |
| 1 | | | | 5 | | | | | 10 | | | | | 15 | |
| Lys | Met | Glu | Asn | Ser | Asn | Leu | Arg | Gln | Glu | Leu | Glu | Asp | Asn | Ser | Asn |
| | | | 20 | | | | | 25 | | | | | 30 | | |
| His | Leu | Thr | Lys | Leu | Glu | Thr | Glu | Ala | Ser | Asn | Met | Lys | Glu | Val | Leu |

-continued

|   |   | 35 |   |   |   |   | 40 |   |   |   |   | 45 |   |   |   |
|---|---|---|---|---|---|---|---|---|---|---|---|---|---|---|---|
| Lys | Gln | Leu | Gln | Gly | Ser | Ile | Glu | Asp | Glu | Ala | Met | Ala | Ser | Ser | Gly |
|   | 50 |   |   |   |   | 55 |   |   |   |   | 60 |   |   |   |   |
| Gln | Ile | Asp | Leu | Leu | Glu | Arg | Leu | Lys | Glu | Leu | Asn | Leu | Asp | Ser | Ser |
| 65 |   |   |   |   | 70 |   |   |   |   | 75 |   |   |   |   | 80 |
| Asn | Phe | Pro | Gly | Val | Lys | Leu | Arg | Ser | Lys | Met | Ser | Leu | Arg | Ser | Tyr |
|   |   |   |   | 85 |   |   |   |   | 90 |   |   |   |   | 95 |   |
| Gly | Ser | Arg | Glu | Gly | Ser | Val | Ser | Ser | Arg | Ser | Gly | Glu | Cys | Ser | Pro |
|   |   |   | 100 |   |   |   |   | 105 |   |   |   |   | 110 |   |   |
| Val | Pro | Met | Gly | Ser | Phe | Pro | Arg | Arg | Gly | Phe | Val | Asn | Gly | Ser | Arg |
|   |   | 115 |   |   |   |   | 120 |   |   |   |   | 125 |   |   |   |
| Glu | Ser | Thr | Gly | Tyr | Leu | Glu | Glu | Leu | Glu | Lys | Glu | Arg | Ser | Leu | Leu |
|   | 130 |   |   |   |   | 135 |   |   |   |   | 140 |   |   |   |   |
| Leu | Ala | Asp | Leu | Asp | Lys | Glu | Glu | Lys | Glu | Lys | Asp | Trp | Tyr | Tyr | Ala |
| 145 |   |   |   |   | 150 |   |   |   |   | 155 |   |   |   |   | 160 |
| Gln | Leu | Gln | Asn | Leu | Thr | Lys | Arg | Ile | Asp | Ser | Leu | Pro | Leu | Thr | Glu |
|   |   |   |   | 165 |   |   |   |   | 170 |   |   |   |   | 175 |   |
| Asn | Phe | Ser | Leu | Gln | Thr | Asp | Leu | Thr | Arg | Arg | Gln | Leu | Glu | Tyr | Glu |
|   |   |   | 180 |   |   |   |   | 185 |   |   |   |   | 190 |   |   |
| Ala | Arg | Gln | Ile | Arg | Val | Ala | Met | Glu | Glu | Gln | Leu | Gly | Thr | Cys | Gln |
|   |   | 195 |   |   |   |   | 200 |   |   |   |   | 205 |   |   |   |
| Asp | Met | Glu | Lys | Arg | Ala | Gln | Arg | Arg | Ile | Ala | Arg | Ile | Gln | Gln | Ile |
|   | 210 |   |   |   |   | 215 |   |   |   |   | 220 |   |   |   |   |
| Glu | Lys | Asp | Ile | Leu | Arg | Ile | Arg | Gln | Leu | Leu | Gln | Ser | Gln | Ala | Thr |
| 225 |   |   |   |   | 230 |   |   |   |   | 235 |   |   |   |   | 240 |
| Glu | Ala | Glu | Arg | Ser | Ser | Gln | Asn | Lys | His | Glu | Thr | Gly | Ser | His | Asp |
|   |   |   |   | 245 |   |   |   |   | 250 |   |   |   |   | 255 |   |
| Ala | Glu | Arg | Gln | Asn | Glu | Gly | Gln | Gly | Val | Gly | Glu | Ile | Asn | Met | Ala |
|   |   |   | 260 |   |   |   |   | 265 |   |   |   |   | 270 |   |   |
| Thr | Ser | Gly | Asn | Gly | Gln | Gly | Ser | Thr | Thr | Arg | Met | Asp | His | Glu | Thr |
|   |   | 275 |   |   |   |   | 280 |   |   |   |   | 285 |   |   |   |
| Ala | Ser | Val | Leu | Ser | Ser | Ser | Thr | His | Ser | Ala | Pro | Arg | Arg | Leu |   |
|   | 290 |   |   |   |   | 295 |   |   |   |   | 300 |   |   |   |   |
| Thr | Ser | His | Leu | Gly | Thr | Lys | Val | Glu | Met | Val | Tyr | Ser | Leu | Leu | Ser |
| 305 |   |   |   |   | 310 |   |   |   |   | 315 |   |   |   |   | 320 |
| Met | Leu | Gly | Thr | His | Asp | Lys | Asp | Met | Ser | Arg | Thr | Leu | Leu | Ala |   |
|   |   |   |   | 325 |   |   |   |   | 330 |   |   |   |   | 335 |   |
| Met | Ser | Ser | Ser | Gln | Asp | Ser | Cys | Ile | Ser | Met | Arg | Gln | Ser | Gly | Cys |
|   |   |   | 340 |   |   |   |   | 345 |   |   |   |   | 350 |   |   |
| Leu | Pro | Leu | Leu | Ile | Gln | Leu | Leu | His | Gly | Asn | Asp | Lys | Asp | Ser | Val |
|   |   | 355 |   |   |   |   | 360 |   |   |   |   | 365 |   |   |   |
| Leu | Leu | Gly | Asn | Ser | Arg | Gly | Ser | Lys | Glu | Ala | Arg | Ala | Arg | Ala | Ser |
|   | 370 |   |   |   |   | 375 |   |   |   |   | 380 |   |   |   |   |
| Ala | Ala | Leu | His | Asn | Ile | Ile | His | Ser | Gln | Pro | Asp | Asp | Lys | Arg | Gly |
| 385 |   |   |   |   | 390 |   |   |   |   | 395 |   |   |   |   | 400 |
| Arg | Arg | Glu | Ile | Arg | Val | Leu | His | Leu | Leu | Glu | Gln | Ile | Arg | Ala | Tyr |
|   |   |   |   | 405 |   |   |   |   | 410 |   |   |   |   | 415 |   |
| Cys | Glu | Thr | Cys | Trp | Glu | Trp | Gln | Glu | Ala | His | Glu | Pro | Gly | Met | Asp |
|   |   |   | 420 |   |   |   |   | 425 |   |   |   |   | 430 |   |   |
| Gln | Asp | Lys | Asn | Pro | Met | Pro | Ala | Pro | Val | Glu | His | Gln | Ile | Cys | Pro |
|   |   | 435 |   |   |   |   | 440 |   |   |   |   | 445 |   |   |   |
| Ala | Val | Cys | Val | Leu | Met | Lys | Leu | Ser | Phe | Asp | Glu | Glu | His | Arg | His |
|   | 450 |   |   |   |   | 455 |   |   |   |   | 460 |   |   |   |   |

| Ala | Met | Asn | Glu | Leu | Gly | Gly | Leu | Gln | Ala | Ile | Ala | Glu | Leu | Leu | Gln |
| 465 | | | | 470 | | | | | 475 | | | | | | 480 |
| Val | Asp | Cys | Glu | Met | Tyr | Gly | Leu | Thr | Asn | Asp | His | Tyr | Ser | Ile | Thr |
| | | | | 485 | | | | 490 | | | | | 495 | | |
| Leu | Arg | Arg | Tyr | Ala | Gly | Met | Ala | Leu | Thr | Asn | Leu | Thr | Phe | Gly | Asp |
| | | | 500 | | | | 505 | | | | | 510 | | | |
| Val | Ala | Asn | Lys | Ala | Thr | Leu | Cys | Ser | Met | Lys | Gly | Cys | Met | Arg | Ala |
| | | 515 | | | | 520 | | | | 525 | | | | | |
| Leu | Val | Ala | Gln | Leu | Lys | Ser | Glu | Ser | Glu | Asp | Leu | Gln | Gln | Val | Ile |
| | 530 | | | | 535 | | | | | 540 | | | | | |
| Ala | Ser | Val | Leu | Arg | Asn | Leu | Ser | Trp | Arg | Ala | Asp | Val | Asn | Ser | Lys |
| 545 | | | | 550 | | | | | 555 | | | | | | 560 |
| Lys | Thr | Leu | Arg | Glu | Val | Gly | Ser | Val | Lys | Ala | Leu | Met | Glu | Cys | Ala |
| | | | 565 | | | | 570 | | | | | 575 | | | |
| Leu | Glu | Val | Lys | Lys | Glu | Ser | Thr | Leu | Lys | Ser | Val | Leu | Ser | Ala | Leu |
| | | | 580 | | | | 585 | | | | | 590 | | | |
| Trp | Asn | Leu | Ser | Ala | His | Cys | Thr | Glu | Asn | Lys | Ala | Asp | Ile | Cys | Ala |
| | | 595 | | | | 600 | | | | 605 | | | | | |
| Val | Asp | Gly | Ala | Leu | Ala | Phe | Leu | Val | Gly | Thr | Leu | Thr | Tyr | Arg | Ser |
| | 610 | | | | 615 | | | | | 620 | | | | | |
| Gln | Thr | Asn | Thr | Leu | Ala | Ile | Ile | Glu | Ser | Gly | Gly | Gly | Ile | Leu | Arg |
| 625 | | | | | 630 | | | | | 635 | | | | | 640 |
| Asn | Val | Ser | Ser | Leu | Ile | Ala | Thr | Asn | Glu | Asp | His | Arg | Gln | Ile | Leu |
| | | | | 645 | | | | 650 | | | | | 655 | | |
| Arg | Glu | Asn | Asn | Cys | Leu | Gln | Thr | Leu | Leu | Gln | His | Leu | Lys | Ser | His |
| | | | 660 | | | | 665 | | | | | 670 | | | |
| Ser | Leu | Thr | Ile | Val | Ser | Asn | Ala | Cys | Gly | Thr | Leu | Trp | Asn | Leu | Ser |
| | | 675 | | | | 680 | | | | 685 | | | | | |
| Ala | Arg | Asn | Pro | Lys | Asp | Gln | Glu | Ala | Leu | Trp | Asp | Met | Gly | Ala | Val |
| | 690 | | | | 695 | | | | | 700 | | | | | |
| Ser | Met | Leu | Lys | Asn | Leu | Ile | His | Ser | Lys | His | Lys | Met | Ile | Ala | Met |
| 705 | | | | 710 | | | | | 715 | | | | | | 720 |
| Gly | Ser | Ala | Ala | Ala | Leu | Arg | Asn | Leu | Met | Ala | Asn | Arg | Pro | Ala | Lys |
| | | | | 725 | | | | 730 | | | | | 735 | | |
| Tyr | Lys | Asp | Ala | Asn | Ile | Met | Ser | Pro | Gly | Ser | Ser | Leu | Pro | Ser | Leu |
| | | | 740 | | | | 745 | | | | | 750 | | | |
| His | Val | Arg | Lys | Gln | Lys | Ala | Leu | Glu | Ala | Glu | Leu | Asp | Ala | Gln | His |
| | | 755 | | | | 760 | | | | 765 | | | | | |
| Leu | Ser | Glu | Thr | Phe | Asp | Asn | Ile | Asp | Asn | Leu | Ser | Pro | Lys | Ala | Ser |
| | 770 | | | | 775 | | | | | 780 | | | | | |
| His | Arg | Ser | Lys | Gln | Arg | His | Lys | Gln | Ser | Leu | Tyr | Gly | Asp | Tyr | Val |
| 785 | | | | 790 | | | | | 795 | | | | | | 800 |
| Phe | Asp | Thr | Asn | Arg | His | Asp | Asp | Asn | Arg | Ser | Asp | Asn | Phe | Asn | Thr |
| | | | | 805 | | | | 810 | | | | | 815 | | |
| Gly | Asn | Met | Thr | Val | Leu | Ser | Pro | Tyr | Leu | Asn | Thr | Thr | Val | Leu | Pro |
| | | | 820 | | | | 825 | | | | | 830 | | | |
| Ser | Ser | Ser | Ser | Ser | Arg | Gly | Ser | Leu | Asp | Ser | Ser | Arg | Ser | Glu | Lys |
| | | | 835 | | | | 840 | | | | | 845 | | | |
| Asp | Arg | Ser | Leu | Glu | Arg | Glu | Arg | Gly | Ile | Gly | Leu | Gly | Asn | Tyr | His |
| | 850 | | | | 855 | | | | | 860 | | | | | |
| Pro | Ala | Thr | Glu | Asn | Pro | Gly | Thr | Ser | Ser | Lys | Arg | Gly | Leu | Gln | Ile |
| 865 | | | | | 870 | | | | | 875 | | | | | 880 |
| Ser | Thr | Thr | Ala | Ala | Gln | Ile | Ala | Lys | Val | Met | Glu | Glu | Val | Ser | Ala |
| | | | | 885 | | | | 890 | | | | | 895 | | |

```
Ile His Thr Ser Gln Glu Asp Arg Ser Ser Gly Ser Thr Thr Glu Leu
            900                 905                 910
His Cys Val Thr Asp Glu Arg Asn Ala Leu Arg Arg Ser Ser Ala Ala
            915                 920                 925
His Thr His Ser Asn Thr Tyr Asn Phe Thr Lys Ser Glu Asn Ser Asn
            930                 935                 940
Arg Thr Cys Ser Met Pro Tyr Ala Lys Leu Glu Tyr Lys Arg Ser Ser
945                 950                 955                 960
Asn Asp Ser Leu Asn Ser Val Ser Ser Asn Asp Gly Tyr Gly Lys Arg
                965                 970                 975
Gly Gln Met Lys Pro Ser Ile Glu Ser Tyr Ser Glu Asp Asp Glu Ser
            980                 985                 990
Lys Phe Cys Ser Tyr Gly Gln Tyr Pro Ala Asp Leu Ala His Lys Ile
            995                 1000                1005
His Ser Ala Asn His Met Asp Asp Asn Asp Gly Glu Leu Asp Thr Pro
            1010                1015                1020
Ile Asn Tyr Ser Leu Lys Tyr Ser Asp Glu Gln Leu Asn Ser Gly Arg
1025                1030                1035                1040
Gln Ser Pro Ser Gln Asn Glu Arg Trp Ala Arg Pro Lys His Ile Ile
                1045                1050                1055
Glu Asp Glu Ile Lys Gln Ser Glu Gln Arg Gln Ser Arg Asn Gln Ser
                1060                1065                1070
Thr Thr Tyr Pro Val Tyr Thr Glu Ser Thr Asp Asp Lys His Leu Lys
                1075                1080                1085
Phe Gln Pro His Phe Gly Gln Gln Glu Cys Val Ser Pro Tyr Arg Ser
            1090                1095                1100
Arg Gly Ala Asn Gly Ser Glu Thr Asn Arg Val Gly Ser Asn His Gly
1105                1110                1115                1120
Ile Asn Gln Asn Val Ser Gln Ser Leu Cys Gln Glu Asp Asp Tyr Glu
                1125                1130                1135
Asp Asp Lys Pro Thr Asn Tyr Ser Glu Arg Tyr Ser Glu Glu Glu Gln
                1140                1145                1150
His Glu Glu Glu Glu Arg Pro Thr Asn Tyr Ser Ile Lys Tyr Asn Glu
            1155                1160                1165
Glu Lys Arg His Val Asp Gln Pro Ile Asp Tyr Ser Leu Lys Tyr Ala
            1170                1175                1180
Thr Asp Ile Pro Ser Ser Gln Lys Gln Ser Phe Ser Phe Ser Lys Ser
1185                1190                1195                1200
Ser Ser Gly Gln Ser Ser Lys Thr Glu His Met Ser Ser Ser Ser Glu
                1205                1210                1215
Asn Thr Ser Thr Pro Ser Ser Asn Ala Lys Arg Gln Asn Gln Leu His
            1220                1225                1230
Pro Ser Ser Ala Gln Ser Arg Ser Gly Gln Pro Gln Lys Ala Ala Thr
            1235                1240                1245
Cys Lys Val Ser Ser Ile Asn Gln Glu Thr Ile Gln Thr Tyr Cys Val
            1250                1255                1260
Glu Asp Thr Pro Ile Cys Phe Ser Arg Cys Ser Ser Leu Ser Ser Leu
1265                1270                1275                1280
Ser Ser Ala Glu Asp Glu Ile Gly Cys Asn Gln Thr Thr Gln Glu Ala
            1285                1290                1295
Asp Ser Ala Asn Thr Leu Gln Ile Ala Glu Ile Lys Gly Lys Ile Gly
            1300                1305                1310
Thr Arg Ser Ala Glu Asp Pro Val Ser Glu Val Pro Ala Val Ser Gln
```

```
                    1315                    1320                    1325
His Pro Arg Thr Lys Ser Ser Arg Leu Gln Gly Ser Ser Leu Ser Ser
               1330                    1335                    1340
Glu Ser Ala Arg His Lys Ala Val Glu Phe Pro Ser Gly Ala Lys Ser
1345                    1350                    1355                    1360
Pro Ser Lys Ser Gly Ala Gln Thr Pro Lys Ser Pro Pro Glu His Tyr
                    1365                    1370                    1375
Val Gln Glu Thr Pro Leu Met Phe Ser Arg Cys Thr Ser Val Ser Ser
               1380                    1385                    1390
Leu Asp Ser Phe Glu Ser Arg Ser Ile Ala Ser Ser Val Gln Ser Glu
                    1395                    1400                    1405
Pro Cys Ser Gly Met Val Ser Gly Ile Ile Ser Pro Ser Asp Leu Pro
               1410                    1415                    1420
Asp Ser Pro Gly Gln Thr Met Pro Pro Ser Arg Ser Lys Thr Pro Pro
1425                    1430                    1435                    1440
Pro Pro Pro Gln Thr Ala Gln Thr Lys Arg Glu Val Pro Lys Asn Lys
                    1445                    1450                    1455
Ala Pro Thr Ala Glu Lys Arg Glu Ser Gly Pro Lys Gln Ala Ala Val
               1460                    1465                    1470
Asn Ala Ala Val Gln Arg Val Gln Val Leu Pro Asp Ala Asp Thr Leu
               1475                    1480                    1485
Leu His Phe Ala Thr Glu Ser Thr Pro Asp Gly Phe Ser Cys Ser Ser
               1490                    1495                    1500
Ser Leu Ser Ala Leu Ser Leu Asp Glu Pro Phe Ile Gln Lys Asp Val
1505                    1510                    1515                    1520
Glu Leu Arg Ile Met Pro Pro Val Gln Glu Asn Asp Asn Gly Asn Glu
                    1525                    1530                    1535
Thr Glu Ser Glu Gln Pro Lys Glu Ser Asn Glu Asn Gln Glu Lys Glu
                    1540                    1545                    1550
Ala Glu Lys Thr Ile Asp Ser Glu Lys Asp Leu Leu Asp Asp Ser Asp
               1555                    1560                    1565
Asp Asp Asp Ile Glu Ile Leu Glu Glu Cys Ile Ile Ser Ala Met Pro
               1570                    1575                    1580
Thr Lys Ser Ser Arg Lys Gly Lys Lys Pro Ala Gln Thr Ala Ser Lys
1585                    1590                    1595                    1600
Leu Pro Pro Pro Val Ala Arg Lys Pro Ser Gln Leu Pro Val Tyr Lys
                    1605                    1610                    1615
Leu Leu Pro Ser Gln Asn Arg Leu Gln Pro Gln Lys His Val Ser Phe
                    1620                    1625                    1630
Thr Pro Gly Asp Asp Met Pro Arg Val Tyr Cys Val Glu Gly Thr Pro
               1635                    1640                    1645
Ile Asn Phe Ser Thr Ala Thr Ser Leu Ser Asp Leu Thr Ile Glu Ser
               1650                    1655                    1660
Pro Pro Asn Glu Leu Ala Ala Gly Glu Gly Val Arg Gly Gly Ala Gln
1665                    1670                    1675                    1680
Ser Gly Glu Phe Glu Lys Arg Asp Thr Ile Pro Thr Glu Gly Arg Ser
                    1685                    1690                    1695
Thr Asp Glu Ala Gln Gly Gly Lys Thr Ser Ser Val Thr Ile Pro Glu
               1700                    1705                    1710
Leu Asp Asp Asn Lys Ala Glu Glu Gly Asp Ile Leu Ala Glu Cys Ile
               1715                    1720                    1725
Asn Ser Ala Met Pro Lys Gly Lys Ser His Lys Pro Phe Arg Val Lys
               1730                    1735                    1740
```

-continued

```
Lys Ile Met Asp Gln Val Gln Gln Ala Ser Ala Ser Ser Ser Ala Pro
1745                1750                1755                1760

Asn Lys Asn Gln Leu Asp Gly Lys Lys Lys Lys Pro Thr Ser Pro Val
            1765                1770                1775

Lys Pro Ile Pro Gln Asn Thr Glu Tyr Arg Thr Arg Val Arg Lys Asn
        1780                1785                1790

Ala Asp Ser Lys Asn Asn Leu Asn Ala Glu Arg Val Phe Ser Asp Asn
    1795                1800                1805

Lys Asp Ser Lys Lys Gln Asn Leu Lys Asn Asn Ser Lys Asp Phe Asn
1810                1815                1820

Asp Lys Leu Pro Asn Asn Glu Asp Arg Val Arg Gly Ser Phe Ala Phe
1825                1830                1835                1840

Asp Ser Pro His His Tyr Thr Pro Ile Glu Gly Thr Pro Tyr Cys Phe
            1845                1850                1855

Ser Arg Asn Asp Ser Leu Ser Ser Leu Asp Phe Asp Asp Asp Asp Val
            1860                1865                1870

Asp Leu Ser Arg Glu Lys Ala Glu Leu Arg Lys Ala Lys Glu Asn Lys
        1875                1880                1885

Glu Ser Glu Ala Lys Val Thr Ser His Thr Glu Leu Thr Ser Asn Gln
    1890                1895                1900

Gln Ser Ala Asn Lys Thr Gln Ala Ile Ala Lys Gln Pro Ile Asn Arg
1905                1910                1915                1920

Gly Gln Pro Lys Pro Ile Leu Gln Lys Gln Ser Thr Phe Pro Gln Ser
            1925                1930                1935

Ser Lys Asp Ile Pro Asp Arg Gly Ala Ala Thr Asp Glu Lys Leu Gln
            1940                1945                1950

Asn Phe Ala Ile Glu Asn Thr Pro Val Cys Phe Ser His Asn Ser Ser
        1955                1960                1965

Leu Ser Ser Leu Ser Asp Ile Asp Gln Glu Asn Asn Asn Lys Glu Asn
    1970                1975                1980

Glu Pro Ile Lys Glu Thr Glu Pro Pro Asp Ser Gln Gly Glu Pro Ser
1985                1990                1995                2000

Lys Pro Gln Ala Ser Gly Tyr Ala Pro Lys Ser Phe His Val Glu Asp
            2005                2010                2015

Thr Pro Val Cys Phe Ser Arg Asn Ser Ser Leu Ser Ser Leu Ser Ile
            2020                2025                2030

Asp Ser Glu Asp Asp Leu Leu Gln Glu Cys Ile Ser Ser Ala Met Pro
        2035                2040                2045

Lys Lys Lys Lys Pro Ser Arg Leu Lys Gly Asp Asn Glu Lys His Ser
2050                2055                2060

Pro Arg Asn Met Gly Gly Ile Leu Gly Glu Asp Leu Thr Leu Asp Leu
2065                2070                2075                2080

Lys Asp Ile Gln Arg Pro Asp Ser Glu His Gly Leu Ser Pro Asp Ser
            2085                2090                2095

Glu Asn Phe Asp Trp Lys Ala Ile Gln Glu Gly Ala Asn Ser Ile Val
            2100                2105                2110

Ser Ser Leu His Gln Ala Ala Ala Ala Cys Leu Ser Arg Gln Ala
        2115                2120                2125

Ser Ser Asp Ser Asp Ser Ile Leu Ser Leu Lys Ser Gly Ile Ser Leu
    2130                2135                2140

Gly Ser Pro Phe His Leu Thr Pro Asp Gln Glu Glu Lys Pro Phe Thr
2145                2150                2155                2160

Ser Asn Lys Gly Pro Arg Ile Leu Lys Pro Gly Glu Lys Ser Thr Leu
            2165                2170                2175
```

```
Glu Thr Lys Lys Ile Glu Ser Glu Ser Lys Gly Ile Lys Gly Gly Lys
        2180                2185                2190

Lys Val Tyr Lys Ser Leu Ile Thr Gly Lys Val Arg Ser Asn Ser Glu
        2195                2200            2205

Ile Ser Gly Gln Met Lys Gln Pro Leu Gln Ala Asn Met Pro Ser Ile
        2210                2215                2220

Ser Arg Gly Arg Thr Met Ile His Ile Pro Gly Val Arg Asn Ser Ser
2225                2230            2235                2240

Ser Ser Thr Ser Pro Val Ser Lys Lys Gly Pro Pro Leu Lys Thr Pro
            2245                2250            2255

Ala Ser Lys Ser Pro Ser Glu Gly Gln Thr Ala Thr Thr Ser Pro Arg
        2260                2265            2270

Gly Ala Lys Pro Ser Val Lys Ser Glu Leu Ser Pro Val Ala Arg Gln
        2275                2280            2285

Thr Ser Gln Ile Gly Gly Ser Ser Lys Ala Pro Ser Arg Ser Gly Ser
        2290                2295            2300

Arg Asp Ser Thr Pro Ser Arg Pro Ala Gln Gln Pro Leu Ser Arg Pro
2305                2310            2315                2320

Ile Gln Ser Pro Gly Arg Asn Ser Ile Ser Pro Gly Arg Asn Gly Ile
            2325                2330            2335

Ser Pro Pro Asn Lys Leu Ser Gln Leu Pro Arg Thr Ser Ser Pro Ser
            2340                2345            2350

Thr Ala Ser Thr Lys Ser Ser Gly Ser Gly Lys Met Ser Tyr Thr Ser
        2355                2360            2365

Pro Gly Arg Gln Met Ser Gln Gln Asn Leu Thr Lys Gln Thr Gly Leu
        2370                2375            2380

Ser Lys Asn Ala Ser Ser Ile Pro Arg Ser Glu Ser Ala Ser Lys Gly
2385                2390            2395                2400

Leu Asn Gln Met Asn Asn Gly Asn Gly Ala Asn Lys Lys Val Glu Leu
            2405                2410            2415

Ser Arg Met Ser Ser Thr Lys Ser Ser Gly Ser Glu Ser Asp Arg Ser
            2420                2425            2430

Glu Arg Pro Val Leu Val Arg Gln Ser Thr Phe Ile Lys Glu Ala Pro
            2435                2440            2445

Ser Pro Thr Leu Arg Arg Lys Leu Glu Glu Ser Ala Ser Phe Glu Ser
            2450                2455            2460

Leu Ser Pro Ser Ser Arg Pro Ala Ser Pro Thr Arg Ser Gln Ala Gln
2465                2470            2475                2480

Thr Pro Val Leu Ser Pro Ser Leu Pro Asp Met Ser Leu Ser Thr His
            2485                2490            2495

Ser Ser Val Gln Ala Gly Gly Trp Arg Lys Leu Pro Pro Asn Leu Ser
            2500                2505            2510

Pro Thr Ile Glu Tyr Asn Asp Gly Arg Pro Ala Lys Arg His Asp Ile
            2515                2520            2525

Ala Arg Ser His Ser Glu Ser Pro Ser Arg Leu Pro Ile Asn Arg Ser
            2530                2535            2540

Gly Thr Trp Lys Arg Glu His Ser Lys His Ser Ser Ser Leu Pro Arg
2545                2550            2555                2560

Val Ser Thr Trp Arg Arg Thr Gly Ser Ser Ser Ser Ile Leu Ser Ala
            2565                2570            2575

Ser Ser Glu Ser Ser Glu Lys Ala Lys Ser Glu Asp Glu Lys His Val
            2580                2585            2590

Asn Ser Ile Ser Gly Thr Lys Gln Ser Lys Glu Asn Gln Val Ser Ala
```

-continued

```
                  2595                    2600                    2605
Lys  Gly  Thr  Trp  Arg  Lys  Ile  Lys  Glu  Asn  Glu  Phe  Ser  Pro  Thr  Asn
          2610                    2615                    2620

Ser  Thr  Ser  Gln  Thr  Val  Ser  Ser  Gly  Ala  Thr  Asn  Gly  Ala  Glu  Ser
2625                    2630                    2635                         2640

Lys  Thr  Leu  Ile  Tyr  Gln  Met  Ala  Pro  Ala  Val  Ser  Lys  Thr  Glu  Asp
                    2645                    2650                    2655

Val  Trp  Val  Arg  Ile  Glu  Asp  Cys  Pro  Ile  Asn  Asn  Pro  Arg  Ser  Gly
               2660                    2665                    2670

Arg  Ser  Pro  Thr  Gly  Asn  Thr  Pro  Pro  Val  Ile  Asp  Ser  Val  Ser  Glu
          2675                    2680                    2685

Lys  Ala  Asn  Pro  Asn  Ile  Lys  Asp  Ser  Lys  Asp  Asn  Gln  Ala  Lys  Gln
          2690                    2695                    2700

Asn  Val  Gly  Asn  Gly  Ser  Val  Pro  Met  Arg  Thr  Val  Gly  Leu  Glu  Asn
2705                    2710                    2715                         2720

Arg  Leu  Thr  Ser  Phe  Ile  Gln  Val  Asp  Ala  Pro  Asp  Gln  Lys  Gly  Thr
                    2725                    2730                    2735

Glu  Ile  Lys  Pro  Gly  Gln  Asn  Asn  Pro  Val  Pro  Val  Ser  Glu  Thr  Asn
                    2740                    2745                    2750

Glu  Ser  Pro  Ile  Val  Glu  Arg  Thr  Pro  Phe  Ser  Ser  Ser  Ser  Ser  Ser
          2755                    2760                    2765

Lys  His  Ser  Ser  Pro  Ser  Gly  Thr  Val  Ala  Ala  Arg  Val  Thr  Pro  Phe
          2770                    2775                    2780

Asn  Tyr  Asn  Pro  Ser  Pro  Arg  Lys  Ser  Ser  Ala  Asp  Ser  Thr  Ser  Ala
2785                    2790                    2795                         2800

Arg  Pro  Ser  Gln  Ile  Pro  Thr  Pro  Val  Asn  Asn  Asn  Thr  Lys  Lys  Arg
                    2805                    2810                    2815

Asp  Ser  Lys  Thr  Asp  Ser  Thr  Glu  Ser  Ser  Gly  Thr  Gln  Ser  Pro  Lys
                    2820                    2825                    2830

Arg  His  Ser  Gly  Ser  Tyr  Leu  Val  Thr  Ser  Val
                    2835                    2840
```

( 2 ) INFORMATION FOR SEQ ID NO:3:

( i ) SEQUENCE CHARACTERISTICS:
        ( A ) LENGTH: 3172 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Homo sapiens ( v i i ) IMMEDIATE SOURCE:
        ( B ) CLONE: DP1(TB2)

( i x ) FEATURE:
        ( A ) NAME/KEY: CDS
        ( B ) LOCATION: 1..630

( x i ) SEQUENCE DESCRIPTION: SEQ ID NO:3:

```
GCA  GTC  GCC  GCT  CCA  GTC  TAT  CCG  GCA  CTA  GGA  ACA  GCC  CCG  GGN  GGC     48
Ala  Val  Ala  Ala  Pro  Val  Tyr  Pro  Ala  Leu  Gly  Thr  Ala  Pro  Gly  Gly
 1                     5                        10                      15

GAG  ACG  GTC  CCC  GCC  ATG  TCT  GCG  GCC  ATG  AGG  GAG  AGG  TTC  GAC  CGG     96
Glu  Thr  Val  Pro  Ala  Met  Ser  Ala  Ala  Met  Arg  Glu  Arg  Phe  Asp  Arg
                20                      25                      30

TTC  CTG  CAC  GAG  AAG  AAC  TGC  ATG  ACT  GAC  CTT  CTG  GCC  AAG  CTC  GAG    144
Phe  Leu  His  Glu  Lys  Asn  Cys  Met  Thr  Asp  Leu  Leu  Ala  Lys  Leu  Glu
```

```
                    35                        40                         45
GCC  AAA  ACC  GGC  GTG  AAC  AGG  AGC  TTC  ATC  GCT  CTT  GGT  GTC  ATC  GGA        192
Ala  Lys  Thr  Gly  Val  Asn  Arg  Ser  Phe  Ile  Ala  Leu  Gly  Val  Ile  Gly
     50                       55                      60

CTG  GTG  GCC  TTG  TAC  CTG  GTG  TTC  GGT  TAT  GGA  GCC  TCT  CTC  CTC  TGC        240
Leu  Val  Ala  Leu  Tyr  Leu  Val  Phe  Gly  Tyr  Gly  Ala  Ser  Leu  Leu  Cys
65                       70                      75                            80

AAC  CTG  ATA  GGA  TTT  GGC  TAC  CCA  GCC  TAC  ATC  TCA  ATT  AAA  GCT  ATA        288
Asn  Leu  Ile  Gly  Phe  Gly  Tyr  Pro  Ala  Tyr  Ile  Ser  Ile  Lys  Ala  Ile
                         85                      90                       95

GAG  AGT  CCC  AAC  AAA  GAA  GAT  GAT  ACC  CAG  TGG  CTG  ACC  TAC  TGG  GTA        336
Glu  Ser  Pro  Asn  Lys  Glu  Asp  Asp  Thr  Gln  Trp  Leu  Thr  Tyr  Trp  Val
                    100                      105                      110

GTG  TAT  GGT  GTG  TTC  AGC  ATT  GCT  GAA  TTC  TTC  TCT  GAT  ATC  TTC  CTG        384
Val  Tyr  Gly  Val  Phe  Ser  Ile  Ala  Glu  Phe  Phe  Ser  Asp  Ile  Phe  Leu
               115                      120                      125

TCA  TGG  TTC  CCC  TTC  TAC  TAC  ATG  CTG  AAG  TGT  GGC  TTC  CTG  TTG  TGG        432
Ser  Trp  Phe  Pro  Phe  Tyr  Tyr  Met  Leu  Lys  Cys  Gly  Phe  Leu  Leu  Trp
     130                      135                      140

TGC  ATG  GCC  CCG  AGC  CCT  TCT  AAT  GGG  GCT  GAA  CTG  CTC  TAC  AAG  CGC        480
Cys  Met  Ala  Pro  Ser  Pro  Ser  Asn  Gly  Ala  Glu  Leu  Leu  Tyr  Lys  Arg
145                      150                      155                      160

ATC  ATC  CGT  CCT  TTC  TTC  CTG  AAG  CAC  GAG  TCC  CAG  ATG  GAC  AGT  GTG        528
Ile  Ile  Arg  Pro  Phe  Phe  Leu  Lys  His  Glu  Ser  Gln  Met  Asp  Ser  Val
                         165                      170                      175

GTC  AAG  GAC  CTT  AAA  GAC  AAG  TCC  AAA  GAG  ACT  GCA  GAT  GCC  ATC  ACT        576
Val  Lys  Asp  Leu  Lys  Asp  Lys  Ser  Lys  Glu  Thr  Ala  Asp  Ala  Ile  Thr
                    180                      185                      190

AAA  GAA  GCG  AAG  AAA  GCT  ACC  GTG  AAT  TTA  CTG  GGT  GAA  GAA  AAG  AAG        624
Lys  Glu  Ala  Lys  Lys  Ala  Thr  Val  Asn  Leu  Leu  Gly  Glu  Glu  Lys  Lys
               195                      200                      205

AGC  ACC  TAAACCAGAC  TAAACCAGAC  TGGATGGAAA  CTTCCTGCCC  TCTCTGTACC               680
Ser  Thr
     210

TTCCTACTGG  AGCTTGATGT  TATATTAGGG  ACTGTGGTAT  AATTATTTTA  ATAATGTTGC               740

CTTGGAAACA  TTTTTGAGAT  ATTAAAGATT  GGAATGTGTT  GTAAGTTTCT  TTGCTTACTT               800

TTACTGTCTA  TATATATAGG  GAGCACTTTA  AACTTAATGC  AGTGGGCAGT  GTCCACGTTT               860

TTGGAAAATG  TATTTTGCCT  CTGGGTAGGA  AAAGATGTAT  GTTGCTATCC  TGCAGGAAAT               920

ATAAACTTAA  AATAAAATTA  TATACCCCAC  AGGCTGTGTA  CTTTACTGGG  CTCTCCCTGC               980

ACGSATTTTC  TCTGTAGTTA  CATTTAGGRT  AATCTTTATG  GTTCTACTTC  CTRTAATGTA              1040

CAATTTTATA  TAATTCNGRA  ATGTTTTAA   TGTATTTGTG  CACATGTACA  TATGGAAATG              1100

TTACTGTCTG  ACTACANCAT  GCATCATGCT  CATGGGGAGG  GAGCAGGGGA  AGGTTGTATG              1160

TGTCATTTAT  AACTTCTGTA  CAGTAAGACC  ACCTGCCAAA  AGCTGGAGGA  ACCATTGTGC              1220

TGGTGTGGTC  TACTAAATAA  TACTTTAGGA  AATACGTGAT  TAATATGCAA  GTGAACAAAG              1280

TGAGAAATGA  AATCGAATGG  AGATTGGCCT  GGTTGTTTCC  GTAGTATATG  GCATATGAAT              1340

ACCAGGATAG  CTTTATAAAG  CAGTTAGTTA  GTTAGTTACT  CACTCTAGTG  ATAAATCGGG              1400

AAATTTACAC  ACACACACAC  ACACACACAC  ACACACACAC  ACACACACAC  ACACACACAG              1460

AGTACCCTGT  AACTCTCAAT  TCCCTGAAAA  ACTAGTAATA  CTGTCTTATC  TGCTATAAAC              1520

TTTACATATT  TGTCTATTGT  CAAGATGCTA  CANTGGAMNC  CATTTCTGGT  TTTATCTTCA              1580

NAGSGGAGAN  ACATGTTGAT  TTAGTCTTCT  TTCCCAATCT  TCTTTTTTAA  MCCAGTTTNA              1640

GGMNCTTCTG  RAGATTTG Y C  CACCTCTGAT  TACATGTATG  TTCT Y GTTTG  TATCATKAGC          1700
```

-continued

| | | | | | |
|---|---|---|---|---|---|
| AACAACATGC | TAATGRCGAC | ACCTAGCTCT | RAGMGCAATT | CTGGGAGANT | GARAGGNWGT | 1760
| ATARAGTMNC | CCATAATCTG | CTTGGCAATA | GTTAAGTCAA | TCTATCTTCA | GTTTTTCTCT | 1820
| GGCCTTTAAG | GTCAAACACA | AGAGGCTTCC | CTAGTTTACA | AGTCAGAGTC | ACTTGTAGTC | 1880
| CATTTAAATG | CCCTCATCCG | TATTCTTTGT | GTTGATAAGC | TGCACAKGAC | TACATAGTAA | 1940
| GTACAGANCA | GTAAAGTTAA | NNCGGATGTC | TCCATTGATC | TGCCAANTCG | NTATAGAGAG | 2000
| CAATTTGTCT | GGACTAGAAA | ATCTGAGTTT | TACACCATAC | TGTTAAGAGT | CCTTTTGAAT | 2060
| TAAACTAGAC | TAAAACAAGT | GTATAACTAA | ACTAACAAGA | TTAAATATCC | AGCCAGTACA | 2120
| GTATTTTTA | AGGCAAATAA | AGATGATTAG | CTCACCTTGA | GNTAACAATC | AGGTAAGATC | 2180
| ATNACAATGT | CTCATGATGT | NAANAATATT | AAAGATATCA | ATACTAAGTG | ACAGTATCAC | 2240
| NNCTAATATA | ATATGGATCA | GAGCATTTAT | TTTGGGGAGG | AAAACAGTGG | TGATTACCGG | 2300
| CATTTATTA | AACTTAAAAC | TTTGTAGAAA | GCAAACAAAA | TTGTTCTTGG | GAGAAAATCA | 2360
| ACTTTTAGAT | TAAAAAAATT | TTAAGTAWCT | AGGAGTATTT | AAATCCTTTT | CCCATAAATA | 2420
| AAAGTACAGT | TTTCTTGGTG | GCAGAATGAA | AATCAGCAAC | NTCTAGCATA | TAGACTATAT | 2480
| AATCAGATTG | ACAGCATATA | GAATATATTA | TCAGACAAGA | TGAGGAGGTA | CAAAAGTTAC | 2540
| TATTGCTCAT | AATGACTTAC | AGGCTAAAAN | TAGNTNTAAA | ATACTATATT | AAATTCTGAA | 2600
| TGCAATTTTT | TTTTGTTCCC | TTGAGACCAA | AATTTAAGTT | AACTGTTGCT | GGCAGTCTAA | 2660
| GTGTAAATGT | TAACAGCAGG | AGAAGTTAAG | AATTGAGCAG | TTCTGTTGCA | TGATTTCCCA | 2720
| AATGAAATAC | TGCCTTGGCT | AGAGTTTGAA | AAACTAATTG | AGCCTGTGCC | TGGCTAGAAA | 2780
| ACAAGCGTTT | ATTTGAATGT | GAATAGTGTT | TCAAAGGTAT | GTAGTTACAG | AATTCCTACC | 2840
| AAACAGCTTA | AATTCTTCAA | GAAAGAATTC | CTGCAGCAGT | TATTCCCTTA | CCTGAAGGCT | 2900
| TCAATCATTT | GGATCAACAA | CTGCTACTCT | CGGGAAGACT | CCTCTACTCA | CAGCTGAAGA | 2960
| AAATGAGCAC | ACCCTTCACA | CTGTTATCAC | CTATCCTGAA | GATGTGATAC | ACTGAATGGA | 3020
| AATAAATAGA | TGTAAATAAA | ATTGAGWTCT | CATTTAAAAA | AAACCATGTG | CCCAATGGGA | 3080
| AAATGACCTC | ATGTTGTGGT | TTAAACAGCA | ACTGCACCCA | CTAGCACAGC | CCATTGAGCT | 3140
| ANCCTATATA | TACATCTCTG | TCAGTGCCCC | TC | | | 3172

( 2 ) INFORMATION FOR SEQ ID NO:4:

( i ) SEQUENCE CHARACTERISTICS:
        ( A ) LENGTH: 210 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Ala  Val  Ala  Ala  Pro  Val  Tyr  Pro  Ala  Leu  Gly  Thr  Ala  Pro  Gly  Gly
 1              5                   10                      15

Glu  Thr  Val  Pro  Ala  Met  Ser  Ala  Ala  Met  Arg  Glu  Arg  Phe  Asp  Arg
               20                  25                      30

Phe  Leu  His  Glu  Lys  Asn  Cys  Met  Thr  Asp  Leu  Leu  Ala  Lys  Leu  Glu
          35                  40                      45

Ala  Lys  Thr  Gly  Val  Asn  Arg  Ser  Phe  Ile  Ala  Leu  Gly  Val  Ile  Gly
      50                  55                      60

Leu  Val  Ala  Leu  Tyr  Leu  Val  Phe  Gly  Tyr  Gly  Ala  Ser  Leu  Leu  Cys
 65                  70                      75                          80

Asn  Leu  Ile  Gly  Phe  Gly  Tyr  Pro  Ala  Tyr  Ile  Ser  Ile  Lys  Ala  Ile
                85                      90                      95
```

-continued

| | | | | | | | | | | | | | | |
|---|---|---|---|---|---|---|---|---|---|---|---|---|---|---|
| Glu | Ser | Pro | Asn<br>100 | Lys | Glu | Asp | Asp | Thr | Gln<br>105 | Trp | Leu | Thr | Tyr<br>110 | Trp | Val |
| Val | Tyr | Gly<br>115 | Val | Phe | Ser | Ile | Ala<br>120 | Glu | Phe | Phe | Ser | Asp<br>125 | Ile | Phe | Leu |
| Ser | Trp<br>130 | Phe | Pro | Phe | Tyr | Tyr<br>135 | Met | Leu | Lys | Cys | Gly<br>140 | Phe | Leu | Leu | Trp |
| Cys<br>145 | Met | Ala | Pro | Ser | Pro<br>150 | Ser | Asn | Gly | Ala | Glu<br>155 | Leu | Leu | Tyr | Lys | Arg<br>160 |
| Ile | Ile | Arg | Pro | Phe<br>165 | Phe | Leu | Lys | His | Glu<br>170 | Ser | Gln | Met | Asp | Ser<br>175 | Val |
| Val | Lys | Asp | Leu<br>180 | Lys | Asp | Lys | Ser | Lys<br>185 | Glu | Thr | Ala | Asp | Ala<br>190 | Ile | Thr |
| Lys | Glu | Ala<br>195 | Lys | Lys | Ala | Thr | Val<br>200 | Asn | Leu | Leu | Gly | Glu<br>205 | Glu | Lys | Lys |
| Ser | Thr<br>210 | | | | | | | | | | | | | | |

( 2 ) INFORMATION FOR SEQ ID NO:5:

( i ) SEQUENCE CHARACTERISTICS:
        ( A ) LENGTH: 434 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Homo sapiens ( v i i ) IMMEDIATE SOURCE:
        ( B ) CLONE: TB1

( x i ) SEQUENCE DESCRIPTION: SEQ ID NO:5:

| | | | | | | | | | | | | | | | |
|---|---|---|---|---|---|---|---|---|---|---|---|---|---|---|---|
| Val<br>1 | Ala | Pro | Val | Val<br>5 | Val | Gly | Ser | Gly | Arg<br>10 | Ala | Pro | Arg | His | Pro<br>15 | Ala |
| Pro | Ala | Ala | Met<br>20 | His | Pro | Arg | Arg | Pro<br>25 | Asp | Gly | Phe | Asp | Gly<br>30 | Leu | Gly |
| Tyr | Arg | Gly<br>35 | Gly | Ala | Arg | Asp | Glu<br>40 | Gln | Gly | Phe | Gly | Gly<br>45 | Ala | Phe | Pro |
| Ala | Arg | Ser<br>50 | Phe | Ser | Thr | Gly | Ser<br>55 | Asp | Leu | Gly | His | Trp<br>60 | Val | Thr | Thr |
| Pro<br>65 | Pro | Asp | Ile | Pro | Gly<br>70 | Ser | Arg | Asn | Leu | His<br>75 | Trp | Gly | Glu | Lys | Ser<br>80 |
| Pro | Pro | Tyr | Gly | Val<br>85 | Pro | Thr | Thr | Ser | Thr<br>90 | Pro | Tyr | Glu | Gly | Pro<br>95 | Thr |
| Glu | Glu | Pro | Phe<br>100 | Ser | Ser | Gly | Gly | Gly<br>105 | Gly | Ser | Val | Gln | Gly<br>110 | Gln | Ser |
| Ser | Glu | Gln<br>115 | Leu | Asn | Arg | Phe | Ala<br>120 | Gly | Phe | Gly | Ile | Gly<br>125 | Leu | Ala | Ser |
| Leu | Phe<br>130 | Thr | Glu | Asn | Val | Leu<br>135 | Ala | His | Pro | Cys | Ile<br>140 | Val | Leu | Arg | Arg |
| Gln<br>145 | Cys | Gln | Val | Asn | Tyr<br>150 | His | Ala | Gln | His | Tyr<br>155 | His | Leu | Thr | Pro | Phe<br>160 |
| Thr | Val | Ile | Asn | Ile<br>165 | Met | Tyr | Ser | Phe | Asn<br>170 | Lys | Thr | Gln | Gly | Pro<br>175 | Arg |
| Ala | Leu | Trp | Lys<br>180 | Gly | Met | Gly | Ser | Thr<br>185 | Phe | Ile | Val | Gln | Gly<br>190 | Val | Thr |
| Leu | Gly | Ala | Glu | Gly | Ile | Ile | Ser | Glu | Phe | Thr | Pro | Leu | Pro | Arg | Glu |

|     |     |     |     |     |     |     |     |     |     |     |     |     |     |     |
|-----|-----|-----|-----|-----|-----|-----|-----|-----|-----|-----|-----|-----|-----|-----|
|     |     |     |     | 195 |     |     | 200 |     |     |     | 205 |     |     |     |
| Val | Leu | His | Lys | Trp | Ser | Pro | Lys | Gln | Ile | Gly | Glu | His | Leu | Leu |
|     |     |     | 210 |     |     |     | 215 |     |     |     | 220 |     |     |     |
| Lys | Ser | Leu | Thr | Tyr | Val | Val | Ala | Met | Pro | Phe | Tyr | Ser | Ala | Ser | Leu |
| 225 |     |     |     |     | 230 |     |     |     | 235 |     |     |     |     | 240 |
| Ile | Glu | Thr | Val | Gln | Ser | Glu | Ile | Ile | Arg | Asp | Asn | Thr | Gly | Ile | Leu |
|     |     |     |     | 245 |     |     |     | 250 |     |     |     |     | 255 |     |
| Glu | Cys | Val | Lys | Glu | Gly | Ile | Gly | Arg | Val | Ile | Gly | Met | Gly | Val | Pro |
|     |     |     | 260 |     |     |     |     | 265 |     |     |     |     | 270 |     |
| His | Ser | Lys | Arg | Leu | Leu | Pro | Leu | Leu | Ser | Leu | Ile | Phe | Pro | Thr | Val |
|     |     | 275 |     |     |     |     | 280 |     |     |     |     | 285 |     |     |
| Leu | His | Gly | Val | Leu | His | Tyr | Ile | Ile | Ser | Ser | Val | Ile | Gln | Lys | Phe |
|     | 290 |     |     |     |     | 295 |     |     |     |     | 300 |     |     |     |     |
| Val | Leu | Leu | Ile | Leu | Lys | Arg | Lys | Thr | Tyr | Asn | Ser | His | Leu | Ala | Glu |
| 305 |     |     |     |     | 310 |     |     |     |     | 315 |     |     |     |     | 320 |
| Ser | Thr | Ser | Pro | Val | Gln | Ser | Met | Leu | Asp | Ala | Tyr | Phe | Pro | Glu | Leu |
|     |     |     |     | 325 |     |     |     | 330 |     |     |     |     | 335 |     |
| Ile | Ala | Asn | Phe | Ala | Ala | Ser | Leu | Cys | Ser | Asp | Val | Ile | Leu | Tyr | Pro |
|     |     |     | 340 |     |     |     |     | 345 |     |     |     |     | 350 |     |
| Leu | Glu | Thr | Val | Leu | His | Arg | Leu | His | Ile | Gln | Gly | Thr | Arg | Thr | Ile |
|     |     | 355 |     |     |     |     | 360 |     |     |     |     | 365 |     |     |
| Ile | Asp | Asn | Thr | Asp | Leu | Gly | Tyr | Glu | Val | Leu | Pro | Ile | Asn | Thr | Gln |
|     | 370 |     |     |     |     | 375 |     |     |     |     | 380 |     |     |     |
| Tyr | Glu | Gly | Met | Arg | Asp | Cys | Ile | Asn | Thr | Ile | Arg | Gln | Glu | Glu | Gly |
| 385 |     |     |     |     | 390 |     |     |     |     | 395 |     |     |     |     | 400 |
| Val | Phe | Gly | Phe | Tyr | Lys | Gly | Phe | Gly | Ala | Val | Ile | Ile | Gln | Tyr | Thr |
|     |     |     |     | 405 |     |     |     | 410 |     |     |     |     | 415 |     |
| Leu | His | Ala | Ala | Val | Leu | Gln | Ile | Thr | Lys | Ile | Ile | Tyr | Ser | Thr | Leu |
|     |     |     | 420 |     |     |     |     | 425 |     |     |     |     | 430 |     |
| Leu | Gln |     |     |     |     |     |     |     |     |     |     |     |     |     |

( 2 ) INFORMATION FOR SEQ ID NO:6:

( i ) SEQUENCE CHARACTERISTICS:
        ( A ) LENGTH: 185 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Homo sapiens ( v i i ) IMMEDIATE SOURCE:
        ( B ) CLONE: YS-39(TB2)

( x i ) SEQUENCE DESCRIPTION: SEQ ID NO:6:

|     |     |     |     |     |     |     |     |     |     |     |     |     |     |     |
|-----|-----|-----|-----|-----|-----|-----|-----|-----|-----|-----|-----|-----|-----|-----|
| Glu | Leu | Arg | Arg | Phe | Asp | Arg | Phe | Leu | His | Glu | Lys | Asn | Cys | Met | Thr |
| 1   |     |     |     | 5   |     |     |     |     | 10  |     |     |     |     | 15  |     |
| Asp | Leu | Leu | Ala | Lys | Leu | Glu | Ala | Lys | Thr | Gly | Val | Asn | Arg | Ser | Phe |
|     |     |     | 20  |     |     |     |     | 25  |     |     |     |     | 30  |     |     |
| Ile | Ala | Leu | Gly | Val | Ile | Gly | Leu | Val | Ala | Leu | Tyr | Leu | Val | Phe | Gly |
|     |     | 35  |     |     |     |     | 40  |     |     |     |     | 45  |     |     |     |
| Tyr | Gly | Ala | Ser | Leu | Leu | Cys | Asn | Leu | Ile | Gly | Phe | Gly | Tyr | Pro | Ala |
|     | 50  |     |     |     |     | 55  |     |     |     |     | 60  |     |     |     |     |
| Tyr | Ile | Ser | Ile | Lys | Ala | Ile | Glu | Ser | Pro | Asn | Lys | Glu | Asp | Asp | Thr |
| 65  |     |     |     |     | 70  |     |     |     |     | 75  |     |     |     |     | 80  |

|     |     |     |     |     |     |     |     |     |     |     |     |     |     |     |
| --- | --- | --- | --- | --- | --- | --- | --- | --- | --- | --- | --- | --- | --- | --- |
| Gln | Trp | Leu | Thr | Tyr 85 | Trp | Val | Val | Gly 90 | Val | Phe | Ser | Ile | Ala 95 | Glu |
| Phe | Phe | Ser | Asp 100 | Ile | Phe | Leu | Ser | Trp 105 | Phe | Pro | Phe | Tyr | Tyr 110 | Ile | Leu |
| Lys | Cys | Gly 115 | Phe | Leu | Leu | Trp | Cys 120 | Met | Ala | Pro | Ser | Pro 125 | Ser | Asn | Gly |
| Ala | Glu 130 | Leu | Leu | Tyr | Lys | Arg 135 | Ile | Ile | Arg | Pro | Phe 140 | Phe | Leu | Lys | His |
| Glu 145 | Ser | Gln | Met | Asp | Ser 150 | Val | Val | Lys | Asp | Leu 155 | Lys | Asp | Lys | Ala | Lys 160 |
| Glu | Thr | Ala | Asp | Ala 165 | Ile | Thr | Lys | Glu | Ala 170 | Lys | Lys | Ala | Thr | Val 175 | Asn |
| Leu | Leu | Gly | Glu 180 | Glu | Lys | Lys | Ser | Thr 185 |

( 2 ) INFORMATION FOR SEQ ID NO:7:

( i ) SEQUENCE CHARACTERISTICS:
        ( A ) LENGTH: 2842 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Homo sapiens ( v i i ) IMMEDIATE SOURCE:
        ( B ) CLONE: APC ( x i ) SEQUENCE DESCRIPTION: SEQ ID NO:7:

|     |     |     |     |     |     |     |     |     |     |     |     |     |     |     |     |
| --- | --- | --- | --- | --- | --- | --- | --- | --- | --- | --- | --- | --- | --- | --- | --- |
| Met 1 | Ala | Ala | Ala | Ser 5 | Tyr | Asp | Gln | Leu | Leu 10 | Lys | Gln | Val | Glu | Ala 15 | Leu |
| Lys | Met | Glu | Asn 20 | Ser | Asn | Leu | Arg | Gln 25 | Glu | Leu | Glu | Asp | Asn 30 | Ser | Asn |
| His | Leu | Thr 35 | Lys | Leu | Glu | Thr | Glu 40 | Ala | Ser | Asn | Met | Lys 45 | Glu | Val | Leu |
| Lys | Gln 50 | Leu | Gln | Gly | Ser | Ile 55 | Glu | Asp | Glu | Ala | Met 60 | Ala | Ser | Ser | Gly |
| Gln 65 | Ile | Asp | Leu | Leu | Glu 70 | Arg | Leu | Lys | Glu | Leu 75 | Asn | Leu | Asp | Ser | Ser 80 |
| Asn | Phe | Pro | Gly | Val 85 | Lys | Leu | Arg | Ser | Lys 90 | Met | Ser | Leu | Arg | Ser 95 | Tyr |
| Gly | Ser | Arg | Glu 100 | Gly | Ser | Val | Ser | Ser 105 | Arg | Ser | Gly | Glu | Cys 110 | Ser | Pro |
| Val | Pro | Met 115 | Gly | Ser | Phe | Pro | Arg 120 | Arg | Gly | Phe | Val | Asn 125 | Gly | Ser | Arg |
| Glu | Ser 130 | Thr | Gly | Tyr | Leu | Glu 135 | Glu | Leu | Glu | Lys | Glu 140 | Arg | Ser | Leu | Leu |
| Leu 145 | Ala | Asp | Leu | Asp | Lys 150 | Glu | Glu | Lys | Glu | Lys 155 | Asp | Trp | Tyr | Tyr | Ala 160 |
| Gln | Leu | Gln | Asn | Leu 165 | Thr | Lys | Arg | Ile | Asp 170 | Ser | Leu | Leu | Thr | Glu 175 | Asn |
| Phe | Ser | Leu | Gln 180 | Thr | Asp | Met | Thr | Arg 185 | Arg | Gln | Leu | Glu | Tyr 190 | Glu | Ala |
| Arg | Gln | Ile 195 | Arg | Val | Ala | Met | Glu 200 | Glu | Gln | Leu | Gly | Thr 205 | Cys | Gln | Asp |
| Met | Glu | Lys | Arg | Ala | Gln | Arg | Arg | Ile | Ala | Arg | Ile | Gln | Gln | Ile | Glu |

-continued

|     |     |     |     |     | 210 |     |     |     |     | 215 |     |     |     |     | 220 |
| --- | --- | --- | --- | --- | --- | --- | --- | --- | --- | --- | --- | --- | --- | --- | --- |
| Lys 225 | Asp | Ile | Leu | Arg | Ile 230 | Arg | Gln | Leu | Leu | Gln 235 | Ser | Gln | Ala | Thr | Glu 240 |
| Ala | Glu | Arg | Ser | Ser 245 | Gln | Asn | Lys | His | Glu 250 | Thr | Gly | Ser | His | Asp 255 | Ala |
| Glu | Arg | Gln | Asn 260 | Glu | Gly | Gln | Gly | Val 265 | Gly | Glu | Ile | Asn | Met 270 | Ala | Thr |
| Ser | Gly | Asn 275 | Gly | Gln | Gly | Ser | Thr 280 | Thr | Arg | Met | Asp | His 285 | Glu | Thr | Ala |
| Ser | Val 290 | Leu | Ser | Ser | Ser | Ser 295 | Thr | His | Ser | Ala | Pro 300 | Arg | Arg | Leu | Thr |
| Ser 305 | His | Leu | Gly | Thr | Lys 310 | Val | Glu | Met | Val | Tyr 315 | Ser | Leu | Leu | Ser | Met 320 |
| Leu | Gly | Thr | His | Asp 325 | Lys | Asp | Asp | Met | Ser 330 | Arg | Thr | Leu | Leu | Ala 335 | Met |
| Ser | Ser | Ser | Gln 340 | Asp | Ser | Cys | Ile | Ser 345 | Met | Arg | Gln | Ser | Gly 350 | Cys | Leu |
| Pro | Leu 355 | Leu | Ile | Gln | Leu | Leu 360 | His | Gly | Asn | Asp | Lys 365 | Asp | Ser | Val | Leu |
| Leu | Gly 370 | Asn | Ser | Arg | Gly | Ser 375 | Lys | Glu | Ala | Arg | Ala 380 | Arg | Ala | Ser | Ala |
| Ala 385 | Leu | His | Asn | Ile | Ile 390 | His | Ser | Gln | Pro | Asp 395 | Asp | Lys | Arg | Gly | Arg 400 |
| Arg | Glu | Ile | Arg | Val 405 | Leu | His | Leu | Leu | Glu 410 | Gln | Ile | Arg | Ala | Tyr 415 | Cys |
| Glu | Thr | Cys | Trp 420 | Glu | Trp | Gln | Glu | Ala 425 | His | Glu | Pro | Gly | Met 430 | Asp | Gln |
| Asp | Lys | Asn 435 | Pro | Met | Pro | Ala | Pro 440 | Val | Glu | His | Gln | Ile 445 | Cys | Pro | Ala |
| Val | Cys 450 | Val | Leu | Met | Lys | Leu 455 | Ser | Phe | Asp | Glu | Glu 460 | His | Arg | His | Ala |
| Met 465 | Asn | Glu | Leu | Gly | Gly 470 | Leu | Gln | Ala | Ile | Ala 475 | Glu | Leu | Leu | Gln | Val 480 |
| Asp | Cys | Glu | Met | Tyr 485 | Gly | Leu | Thr | Asn | Asp 490 | His | Tyr | Ser | Ile | Thr 495 | Leu |
| Arg | Arg | Tyr | Ala 500 | Gly | Met | Ala | Leu | Thr 505 | Asn | Leu | Thr | Phe | Gly 510 | Asp | Val |
| Ala | Asn | Lys 515 | Ala | Thr | Leu | Cys | Ser 520 | Met | Lys | Gly | Cys | Met 525 | Arg | Ala | Leu |
| Val | Ala 530 | Gln | Leu | Lys | Ser | Glu 535 | Ser | Glu | Asp | Leu | Gln 540 | Gln | Val | Ile | Ala |
| Ser 545 | Val | Leu | Arg | Asn | Leu 550 | Ser | Trp | Arg | Ala | Asp 555 | Val | Asn | Ser | Lys | Lys 560 |
| Thr | Leu | Arg | Glu | Val 565 | Gly | Ser | Val | Lys | Ala 570 | Leu | Met | Glu | Cys | Ala 575 | Leu |
| Glu | Val | Lys | Lys 580 | Glu | Ser | Thr | Leu | Lys 585 | Ser | Val | Leu | Ser | Ala 590 | Leu | Trp |
| Asn | Leu | Ser 595 | Ala | His | Cys | Thr | Glu 600 | Asn | Lys | Ala | Asp | Ile 605 | Cys | Ala | Val |
| Asp | Gly 610 | Ala | Leu | Ala | Phe | Leu 615 | Val | Gly | Thr | Leu | Thr 620 | Tyr | Arg | Ser | Gln |
| Thr 625 | Asn | Thr | Leu | Ala | Ile 630 | Ile | Glu | Ser | Gly | Gly 635 | Gly | Ile | Leu | Arg | Asn 640 |

```
Val  Ser  Ser  Leu  Ile  Ala  Thr  Asn  Glu  Asp  His  Arg  Gln  Ile  Leu  Arg
               645                      650                      655

Glu  Asn  Asn  Cys  Leu  Gln  Thr  Leu  Leu  Gln  His  Leu  Lys  Ser  His  Ser
660                      665                      670

Leu  Thr  Ile  Val  Ser  Asn  Ala  Cys  Gly  Thr  Leu  Trp  Asn  Leu  Ser  Ala
          675                      680                      685

Arg  Asn  Pro  Lys  Asp  Gln  Glu  Ala  Leu  Trp  Asp  Met  Gly  Ala  Val  Ser
690                      695                      700

Met  Leu  Lys  Asn  Leu  Ile  His  Ser  Lys  His  Lys  Met  Ile  Ala  Met  Gly
705                      710                      715                      720

Ser  Ala  Ala  Ala  Leu  Arg  Asn  Leu  Met  Ala  Asn  Arg  Pro  Ala  Lys  Tyr
                    725                      730                      735

Lys  Asp  Ala  Asn  Ile  Met  Ser  Pro  Gly  Ser  Ser  Leu  Pro  Ser  Leu  His
               740                      745                      750

Val  Arg  Lys  Gln  Lys  Ala  Leu  Glu  Ala  Glu  Leu  Asp  Ala  Gln  His  Leu
          755                      760                      765

Ser  Glu  Thr  Phe  Asp  Asn  Ile  Asp  Asn  Leu  Ser  Pro  Lys  Ala  Ser  His
     770                      775                      780

Arg  Ser  Lys  Gln  Arg  His  Lys  Gln  Ser  Leu  Tyr  Gly  Asp  Tyr  Val  Phe
785                      790                      795                      800

Asp  Thr  Asn  Arg  His  Asp  Asp  Asn  Arg  Ser  Asp  Asn  Phe  Asn  Thr  Gly
                    805                      810                      815

Asn  Met  Thr  Val  Leu  Ser  Pro  Tyr  Leu  Asn  Thr  Thr  Val  Leu  Pro  Ser
               820                      825                      830

Ser  Ser  Ser  Ser  Arg  Gly  Ser  Leu  Asp  Ser  Ser  Arg  Ser  Glu  Lys  Asp
               835                      840                      845

Arg  Ser  Leu  Glu  Arg  Glu  Arg  Gly  Ile  Gly  Leu  Gly  Asn  Tyr  His  Pro
850                      855                      860

Ala  Thr  Glu  Asn  Pro  Gly  Thr  Ser  Ser  Lys  Arg  Gly  Leu  Gln  Ile  Ser
865                      870                      875                      880

Thr  Thr  Ala  Ala  Gln  Ile  Ala  Lys  Val  Met  Glu  Glu  Val  Ser  Ala  Ile
                    885                      890                      895

His  Thr  Ser  Gln  Glu  Asp  Arg  Ser  Ser  Gly  Ser  Thr  Thr  Glu  Leu  His
               900                      905                      910

Cys  Val  Thr  Asp  Glu  Arg  Asn  Ala  Leu  Arg  Arg  Ser  Ser  Ala  Ala  His
          915                      920                      925

Thr  His  Ser  Asn  Thr  Tyr  Asn  Phe  Thr  Lys  Ser  Glu  Asn  Ser  Asn  Arg
     930                      935                      940

Thr  Cys  Ser  Met  Pro  Tyr  Ala  Lys  Leu  Glu  Tyr  Lys  Arg  Ser  Ser  Asn
945                      950                      955                      960

Asp  Ser  Leu  Asn  Ser  Val  Ser  Ser  Ser  Asp  Gly  Tyr  Gly  Lys  Arg  Gly
                    965                      970                      975

Gln  Met  Lys  Pro  Ser  Ile  Glu  Ser  Tyr  Ser  Glu  Asp  Asp  Glu  Ser  Lys
               980                      985                      990

Phe  Cys  Ser  Tyr  Gly  Gln  Tyr  Pro  Ala  Asp  Leu  Ala  His  Lys  Ile  His
          995                      1000                     1005

Ser  Ala  Asn  His  Met  Asp  Asp  Asn  Asp  Gly  Glu  Leu  Asp  Thr  Pro  Ile
     1010                     1015                     1020

Asn  Tyr  Ser  Leu  Lys  Tyr  Ser  Asp  Glu  Gln  Leu  Asn  Ser  Gly  Arg  Gln
1025                     1030                     1035                     1040

Ser  Pro  Ser  Gln  Asn  Glu  Arg  Trp  Ala  Arg  Pro  Lys  His  Ile  Ile  Glu
                    1045                     1050                     1055

Asp  Glu  Ile  Lys  Gln  Ser  Glu  Gln  Arg  Gln  Ser  Arg  Asn  Gln  Ser  Thr
               1060                     1065                     1070
```

```
Thr  Tyr  Pro  Val  Tyr  Thr  Glu  Ser  Thr  Asp  Asp  Lys  His  Leu  Lys  Phe
               1075                1080                1085

Gln  Pro  His  Phe  Gly  Gln  Gln  Glu  Cys  Val  Ser  Pro  Tyr  Arg  Ser  Arg
          1090                1095                1100

Gly  Ala  Asn  Gly  Ser  Glu  Thr  Asn  Arg  Val  Gly  Ser  Asn  His  Gly  Ile
1105                1110                1115                          1120

Asn  Gln  Asn  Val  Ser  Gln  Ser  Leu  Cys  Gln  Glu  Asp  Asp  Tyr  Glu  Asp
                    1125                1130                     1135

Asp  Lys  Pro  Thr  Asn  Tyr  Ser  Glu  Arg  Tyr  Ser  Glu  Glu  Gln  His
               1140                1145                1150

Glu  Glu  Glu  Glu  Arg  Pro  Thr  Asn  Tyr  Ser  Ile  Lys  Tyr  Asn  Glu  Glu
               1155                1160                1165

Lys  Arg  His  Val  Asp  Gln  Pro  Ile  Asp  Tyr  Ser  Leu  Lys  Tyr  Ala  Thr
          1170                1175                1180

Asp  Ile  Pro  Ser  Ser  Gln  Lys  Gln  Ser  Phe  Ser  Phe  Ser  Lys  Ser  Ser
1185                1190                1195                          1200

Ser  Gly  Gln  Ser  Ser  Lys  Thr  Glu  His  Met  Ser  Ser  Ser  Ser  Glu  Asn
                    1205                1210                     1215

Thr  Ser  Thr  Pro  Ser  Ser  Asn  Ala  Lys  Arg  Gln  Asn  Gln  Leu  His  Pro
               1220                1225                1230

Ser  Ser  Ala  Gln  Ser  Arg  Ser  Gly  Gln  Pro  Gln  Lys  Ala  Ala  Thr  Cys
          1235                1240                1245

Lys  Val  Ser  Ser  Ile  Asn  Gln  Glu  Thr  Ile  Gln  Thr  Tyr  Cys  Val  Glu
          1250                1255                1260

Asp  Thr  Pro  Ile  Cys  Phe  Ser  Arg  Cys  Ser  Ser  Leu  Ser  Ser  Leu  Ser
1265                1270                1275                          1280

Ser  Ala  Glu  Asp  Glu  Ile  Gly  Cys  Asn  Gln  Thr  Thr  Gln  Glu  Ala  Asp
               1285                1290                1295

Ser  Ala  Asn  Thr  Leu  Gln  Ile  Ala  Glu  Ile  Lys  Glu  Lys  Ile  Gly  Thr
               1300                1305                1310

Arg  Ser  Ala  Glu  Asp  Pro  Val  Ser  Glu  Val  Pro  Ala  Val  Ser  Gln  His
               1315                1320                1325

Pro  Arg  Thr  Lys  Ser  Ser  Arg  Leu  Gln  Gly  Ser  Ser  Leu  Ser  Ser  Glu
          1330                1335                1340

Ser  Ala  Arg  His  Lys  Ala  Val  Glu  Phe  Ser  Ser  Gly  Ala  Lys  Ser  Pro
1345                1350                1355                          1360

Ser  Lys  Ser  Gly  Ala  Gln  Thr  Pro  Lys  Ser  Pro  Pro  Glu  His  Tyr  Val
                    1365                1370                     1375

Gln  Glu  Thr  Pro  Leu  Met  Phe  Ser  Arg  Cys  Thr  Ser  Val  Ser  Ser  Leu
               1380                1385                1390

Asp  Ser  Phe  Glu  Ser  Arg  Ser  Ile  Ala  Ser  Ser  Val  Gln  Ser  Glu  Pro
               1395                1400                1405

Cys  Ser  Gly  Met  Val  Ser  Gly  Ile  Ile  Ser  Pro  Ser  Asp  Leu  Pro  Asp
          1410                1415                1420

Ser  Pro  Gly  Gln  Thr  Met  Pro  Pro  Ser  Arg  Ser  Lys  Thr  Pro  Pro  Pro
1425                1430                1435                          1440

Pro  Pro  Gln  Thr  Ala  Gln  Thr  Lys  Arg  Glu  Val  Pro  Lys  Asn  Lys  Ala
                    1445                1450                     1455

Pro  Thr  Ala  Glu  Lys  Arg  Glu  Ser  Gly  Pro  Lys  Gln  Ala  Ala  Val  Asn
               1460                1465                1470

Ala  Ala  Val  Gln  Arg  Val  Gln  Val  Leu  Pro  Asp  Ala  Asp  Thr  Leu  Leu
               1475                1480                1485

His  Phe  Ala  Thr  Glu  Ser  Thr  Pro  Asp  Gly  Phe  Ser  Cys  Ser  Ser  Ser
```

```
                    1490                    1495                         1500
Leu  Ser  Ala  Leu  Ser  Leu  Asp  Glu  Pro  Phe  Ile  Gln  Lys  Asp  Val  Glu
1505                     1510                     1515                     1520

Leu  Arg  Ile  Met  Pro  Pro  Val  Gln  Glu  Asn  Asp  Asn  Gly  Asn  Glu  Thr
               1525                     1530                     1535

Glu  Ser  Glu  Gln  Pro  Lys  Glu  Ser  Asn  Glu  Asn  Gln  Glu  Lys  Glu  Ala
                    1540                     1545                     1550

Glu  Lys  Thr  Ile  Asp  Ser  Glu  Lys  Asp  Leu  Leu  Asp  Asp  Ser  Asp  Asp
               1555                     1560                     1565

Asp  Asp  Ile  Glu  Ile  Leu  Glu  Glu  Cys  Ile  Ile  Ser  Ala  Met  Pro  Thr
          1570                     1575                     1580

Lys  Ser  Ser  Arg  Lys  Ala  Lys  Lys  Pro  Ala  Gln  Thr  Ala  Ser  Lys  Leu
1585                     1590                     1595                     1600

Pro  Pro  Pro  Val  Ala  Arg  Lys  Pro  Ser  Gln  Leu  Pro  Val  Tyr  Lys  Leu
                         1605                     1610                     1615

Leu  Pro  Ser  Gln  Asn  Arg  Leu  Gln  Pro  Gln  Lys  His  Val  Ser  Phe  Thr
                    1620                     1625                     1630

Pro  Gly  Asp  Asp  Met  Pro  Arg  Val  Tyr  Cys  Val  Glu  Gly  Thr  Pro  Ile
               1635                     1640                     1645

Asn  Phe  Ser  Thr  Ala  Thr  Ser  Leu  Ser  Asp  Leu  Thr  Ile  Glu  Ser  Pro
          1650                     1655                     1660

Pro  Asn  Glu  Leu  Ala  Ala  Gly  Glu  Gly  Val  Arg  Gly  Gly  Ala  Gln  Ser
1665                     1670                     1675                     1680

Gly  Glu  Phe  Glu  Lys  Arg  Asp  Thr  Ile  Pro  Thr  Glu  Gly  Arg  Ser  Thr
                         1685                     1690                     1695

Asp  Glu  Ala  Gln  Gly  Gly  Lys  Thr  Ser  Ser  Val  Thr  Ile  Pro  Glu  Leu
                    1700                     1705                     1710

Asp  Asp  Asn  Lys  Ala  Glu  Glu  Gly  Asp  Ile  Leu  Ala  Glu  Cys  Ile  Asn
               1715                     1720                     1725

Ser  Ala  Met  Pro  Lys  Gly  Lys  Ser  His  Lys  Pro  Phe  Arg  Val  Lys  Lys
               1730                     1735                     1740

Ile  Met  Asp  Gln  Val  Gln  Gln  Ala  Ser  Ala  Ser  Ser  Ser  Ala  Pro  Asn
1745                     1750                     1755                     1760

Lys  Asn  Gln  Leu  Asp  Gly  Lys  Lys  Lys  Lys  Pro  Thr  Ser  Pro  Val  Lys
                    1765                     1770                     1775

Pro  Ile  Pro  Gln  Asn  Thr  Glu  Tyr  Arg  Thr  Arg  Val  Arg  Lys  Asn  Ala
               1780                     1785                     1790

Asp  Ser  Lys  Asn  Asn  Leu  Asn  Ala  Glu  Arg  Val  Phe  Ser  Asp  Asn  Lys
               1795                     1800                     1805

Asp  Ser  Lys  Lys  Gln  Asn  Leu  Lys  Asn  Asn  Ser  Lys  Asp  Phe  Asn  Asp
               1810                     1815                     1820

Lys  Leu  Pro  Asn  Asn  Glu  Asp  Arg  Val  Arg  Gly  Ser  Phe  Ala  Phe  Asp
1825                     1830                     1835                     1840

Ser  Pro  His  His  Tyr  Thr  Pro  Ile  Glu  Gly  Thr  Pro  Tyr  Cys  Phe  Ser
                    1845                     1850                     1855

Arg  Asn  Asp  Ser  Leu  Ser  Ser  Leu  Asp  Phe  Asp  Asp  Asp  Val  Asp
               1860                     1865                     1870

Leu  Ser  Arg  Glu  Lys  Ala  Glu  Leu  Arg  Lys  Ala  Lys  Glu  Asn  Lys  Glu
               1875                     1880                     1885

Ser  Glu  Ala  Lys  Val  Thr  Ser  His  Thr  Glu  Leu  Thr  Ser  Asn  Gln  Gln
               1890                     1895                     1900

Ser  Ala  Asn  Lys  Thr  Gln  Ala  Ile  Ala  Lys  Gln  Pro  Ile  Asn  Arg  Gly
1905                     1910                     1915                     1920
```

```
Gln Pro Lys Pro Ile Leu Gln Lys Gln Ser Thr Phe Pro Gln Ser Ser
            1925            1930                    1935
Lys Asp Ile Pro Asp Arg Gly Ala Ala Thr Asp Glu Lys Leu Gln Asn
            1940            1945                    1950
Phe Ala Ile Glu Asn Thr Pro Val Cys Phe Ser His Asn Ser Ser Leu
            1955            1960                    1965
Ser Ser Leu Ser Asp Ile Asp Gln Glu Asn Asn Asn Lys Glu Asn Glu
            1970            1975                    1980
Pro Ile Lys Glu Thr Glu Pro Pro Asp Ser Gln Gly Glu Pro Ser Lys
1985            1990            1995                    2000
Pro Gln Ala Ser Gly Tyr Ala Pro Lys Ser Phe His Val Glu Asp Thr
            2005            2010                    2015
Pro Val Cys Phe Ser Arg Asn Ser Ser Leu Ser Ser Leu Ser Ile Asp
            2020            2025                    2030
Ser Glu Asp Asp Leu Leu Gln Glu Cys Ile Ser Ser Ala Met Pro Lys
            2035            2040                    2045
Lys Lys Lys Pro Ser Arg Leu Lys Gly Asp Asn Glu Lys His Ser Pro
2050            2055            2060
Arg Asn Met Gly Gly Ile Leu Gly Glu Asp Leu Thr Leu Asp Leu Lys
2065            2070            2075                    2080
Asp Ile Gln Arg Pro Asp Ser Glu His Gly Leu Ser Pro Asp Ser Glu
            2085            2090                    2095
Asn Phe Asp Trp Lys Ala Ile Gln Glu Gly Ala Asn Ser Ile Val Ser
            2100            2105                    2110
Ser Leu His Gln Ala Ala Ala Ala Ala Cys Leu Ser Arg Gln Ala Ser
            2115            2120                    2125
Ser Asp Ser Asp Ser Ile Leu Ser Leu Lys Ser Gly Ile Ser Leu Gly
            2130            2135                    2140
Ser Pro Phe His Leu Thr Pro Asp Gln Glu Glu Lys Pro Phe Thr Ser
2145            2150            2155                    2160
Asn Lys Gly Pro Arg Ile Leu Lys Pro Gly Glu Lys Ser Thr Leu Glu
            2165            2170                    2175
Thr Lys Lys Ile Glu Ser Glu Ser Lys Gly Ile Lys Gly Gly Lys Lys
            2180            2185                    2190
Val Tyr Lys Ser Leu Ile Thr Gly Lys Val Arg Ser Asn Ser Glu Ile
            2195            2200                    2205
Ser Gly Gln Met Lys Gln Pro Leu Gln Ala Asn Met Pro Ser Ile Ser
            2210            2215                    2220
Arg Gly Arg Thr Met Ile His Ile Pro Gly Val Arg Asn Ser Ser Ser
2225            2230            2235                    2240
Ser Thr Ser Pro Val Ser Lys Lys Gly Pro Pro Leu Lys Thr Pro Ala
            2245            2250                    2255
Ser Lys Ser Pro Ser Glu Gly Gln Thr Ala Thr Thr Ser Pro Arg Gly
            2260            2265                    2270
Ala Lys Pro Ser Val Lys Ser Glu Leu Ser Pro Val Ala Arg Gln Thr
            2275            2280                    2285
Ser Gln Ile Gly Gly Ser Ser Lys Ala Pro Ser Arg Ser Gly Ser Arg
            2290            2295                    2300
Asp Ser Thr Pro Ser Arg Pro Ala Gln Gln Pro Leu Ser Arg Pro Ile
2305            2310            2315                    2320
Gln Ser Pro Gly Arg Asn Ser Ile Ser Pro Gly Arg Asn Gly Ile Ser
            2325            2330                    2335
Pro Pro Asn Lys Leu Ser Gln Leu Pro Arg Thr Ser Ser Pro Ser Thr
            2340            2345                    2350
```

```
Ala  Ser  Thr  Lys  Ser  Ser  Gly  Ser  Gly  Lys  Met  Ser  Tyr  Thr  Ser  Pro
          2355                    2360                    2365

Gly  Arg  Gln  Met  Ser  Gln  Gln  Asn  Leu  Thr  Lys  Gln  Thr  Gly  Leu  Ser
          2370                    2375                    2380

Lys  Asn  Ala  Ser  Ser  Ile  Pro  Arg  Ser  Glu  Ser  Ala  Ser  Lys  Gly  Leu
2385                     2390                    2395                         2400

Asn  Gln  Met  Asn  Asn  Gly  Asn  Gly  Ala  Asn  Lys  Lys  Val  Glu  Leu  Ser
               2405                    2410                    2415

Arg  Met  Ser  Ser  Thr  Lys  Ser  Ser  Gly  Ser  Glu  Ser  Asp  Arg  Ser  Glu
               2420                    2425                    2430

Arg  Pro  Val  Leu  Val  Arg  Gln  Ser  Thr  Phe  Ile  Lys  Glu  Ala  Pro  Ser
          2435                    2440                    2445

Pro  Thr  Leu  Arg  Arg  Lys  Leu  Glu  Glu  Ser  Ala  Ser  Phe  Glu  Ser  Leu
          2450                    2455                    2460

Ser  Pro  Ser  Ser  Arg  Pro  Ala  Ser  Pro  Thr  Arg  Ser  Gln  Ala  Gln  Thr
2465                     2470                    2475                         2480

Pro  Val  Leu  Ser  Pro  Ser  Leu  Pro  Asp  Met  Ser  Leu  Ser  Thr  His  Ser
               2485                    2490                    2495

Ser  Val  Gln  Ala  Gly  Gly  Trp  Arg  Lys  Leu  Pro  Pro  Asn  Leu  Ser  Pro
               2500                    2505                    2510

Thr  Ile  Glu  Tyr  Asn  Asp  Gly  Arg  Pro  Ala  Lys  Arg  His  Asp  Ile  Ala
               2515                    2520                    2525

Arg  Ser  His  Ser  Glu  Ser  Pro  Ser  Arg  Leu  Pro  Ile  Asn  Arg  Ser  Gly
               2530                    2535                    2540

Thr  Trp  Lys  Arg  Glu  His  Ser  Lys  His  Ser  Ser  Ser  Leu  Pro  Arg  Val
2545                     2550                    2555                         2560

Ser  Thr  Trp  Arg  Arg  Thr  Gly  Ser  Ser  Ser  Ser  Ile  Leu  Ser  Ala  Ser
               2565                    2570                    2575

Ser  Glu  Ser  Ser  Glu  Lys  Ala  Lys  Ser  Glu  Asp  Glu  Lys  His  Val  Asn
               2580                    2585                    2590

Ser  Ile  Ser  Gly  Thr  Lys  Gln  Ser  Lys  Glu  Asn  Gln  Val  Ser  Ala  Lys
               2595                    2600                    2605

Gly  Thr  Trp  Arg  Lys  Ile  Lys  Glu  Asn  Glu  Phe  Ser  Pro  Thr  Asn  Ser
               2610                    2615                    2620

Thr  Ser  Gln  Thr  Val  Ser  Ser  Gly  Ala  Thr  Asn  Gly  Ala  Glu  Ser  Lys
2625                     2630                    2635                         2640

Thr  Leu  Ile  Tyr  Gln  Met  Ala  Pro  Ala  Val  Ser  Lys  Thr  Glu  Asp  Val
               2645                    2650                    2655

Trp  Val  Arg  Ile  Glu  Asp  Cys  Pro  Ile  Asn  Asn  Pro  Arg  Ser  Gly  Arg
               2660                    2665                    2670

Ser  Pro  Thr  Gly  Asn  Thr  Pro  Pro  Val  Ile  Asp  Ser  Val  Ser  Glu  Lys
               2675                    2680                    2685

Ala  Asn  Pro  Asn  Ile  Lys  Asp  Ser  Lys  Asp  Asn  Gln  Ala  Lys  Gln  Asn
               2690                    2695                    2700

Val  Gly  Asn  Gly  Ser  Val  Pro  Met  Arg  Thr  Val  Gly  Leu  Glu  Asn  Arg
2705                     2710                    2715                         2720

Leu  Asn  Ser  Phe  Ile  Gln  Val  Asp  Ala  Pro  Asp  Gln  Lys  Gly  Thr  Glu
               2725                    2730                    2735

Ile  Lys  Pro  Gly  Gln  Asn  Asn  Pro  Val  Pro  Val  Ser  Glu  Thr  Asn  Glu
               2740                    2745                    2750

Ser  Ser  Ile  Val  Glu  Arg  Thr  Pro  Phe  Ser  Ser  Ser  Ser  Ser  Ser  Lys
               2755                    2760                    2765

His  Ser  Ser  Pro  Ser  Gly  Thr  Val  Ala  Ala  Arg  Val  Thr  Pro  Phe  Asn
```

|  |
|---|
| 2770 2775 2780 |

Tyr Asn Pro Ser Pro Arg Lys Ser Ser Ala Asp Ser Thr Ser Ala Arg
2785                 2790                2795                 2800

Pro Ser Gln Ile Pro Thr Pro Val Asn Asn Asn Thr Lys Lys Arg Asp
           2805               2810                 2815

Ser Lys Thr Asp Ser Thr Glu Ser Ser Gly Thr Gln Ser Pro Lys Arg
          2820           2825                 2830

His Ser Gly Ser Tyr Leu Val Thr Ser Val
          2835          2840

( 2 ) INFORMATION FOR SEQ ID NO:8:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: ral2(yeast)

( x i ) SEQUENCE DESCRIPTION: SEQ ID NO:8:

Leu Thr Gly Ala Lys Gly Leu Gln Leu Arg Ala Leu Arg Arg Ile Ala
1                5                   10                  15

Arg Ile Glu Gln Gly Gly Thr Ala Ile Ser Pro Thr Ser Pro Leu
            20              25                  30

( 2 ) INFORMATION FOR SEQ ID NO:9:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Homo sapiens ( v i i ) IMMEDIATE SOURCE:
        ( B ) CLONE: m3(mAChR)

( x i ) SEQUENCE DESCRIPTION: SEQ ID NO:9:

Leu Tyr Trp Arg Ile Tyr Lys Glu Thr Glu Lys Arg Thr Lys Glu Leu
1                5                   10                  15

Ala Gly Leu Gln Ala Ser Gly Thr Glu Ala Glu Thr Glu
            20              25

( 2 ) INFORMATION FOR SEQ ID NO:10:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Homo sapiens ( v i i ) IMMEDIATE SOURCE:
        ( B ) CLONE: MCC ( x i ) SEQUENCE DESCRIPTION: SEQ ID NO:10:

```
   Leu  Tyr  Pro  Asn  Leu  Ala  Glu  Glu  Arg  Ser  Arg  Trp  Glu  Lys  Glu  Leu
   1              5                        10                       15

Ala  Gly  Leu  Arg  Glu  Glu  Asn  Glu  Ser  Leu  Thr  Ala  Met
             20                       25
```

( 2 ) INFORMATION FOR SEQ ID NO:11:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:11:

GTATCAAGAC TGTGACTTTT AATTGTAGTT TATCCATTTT                    40

( 2 ) INFORMATION FOR SEQ ID NO:12:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:12:

TTTAGAATTT CATGTTAATA TATTGTGTTC TTTTTAACAG                    40

( 2 ) INFORMATION FOR SEQ ID NO:13:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:13:

GTAGATTTTA AAAGGTGTT TTAAAATAAT TTTTTAAGCT                     40

( 2 ) INFORMATION FOR SEQ ID NO:14:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:14:

AAGCAATTGT TGTATAAAAA CTTGTTTCTA TTTTATTTAG                    40

( 2 ) INFORMATION FOR SEQ ID NO:15:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( i i ) MOLECULE TYPE: cDNA ( v i ) ORIGINAL SOURCE:
  ( A ) ORGANISM: Homo sapiens ( x i ) SEQUENCE DESCRIPTION: SEQ ID NO:15:

GTAACTTTTC TTCATATAGT AAACATTGCC TTGTGTACTC        40

( 2 ) INFORMATION FOR SEQ ID NO:16:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( i i ) MOLECULE TYPE: cDNA ( v i ) ORIGINAL SOURCE:
  ( A ) ORGANISM: Homo sapiens ( x i ) SEQUENCE DESCRIPTION: SEQ ID NO:16:

NNNNNNNNN NNNGTCCCTT TTTTAAAAA AAAAAAATAG         40

( 2 ) INFORMATION FOR SEQ ID NO:17:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( i i ) MOLECULE TYPE: cDNA ( v i ) ORIGINAL SOURCE:
  ( A ) ORGANISM: Homo sapiens ( x i ) SEQUENCE DESCRIPTION: SEQ ID NO:17:

GTAAGTAACT TGGCAGTACA ACTTATTTGA AACTTTAATA        40

( 2 ) INFORMATION FOR SEQ ID NO:18:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( i i ) MOLECULE TYPE: cDNA ( v i ) ORIGINAL SOURCE:
  ( A ) ORGANISM: Homo sapiens ( x i ) SEQUENCE DESCRIPTION: SEQ ID NO:18:

ATACAAGATA TTGATACTTT TTTATTATTT GTGGTTTTAG        40

( 2 ) INFORMATION FOR SEQ ID NO:19:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( i i ) MOLECULE TYPE: cDNA ( v i ) ORIGINAL SOURCE:
 ( A ) ORGANISM: Homo sapiens ( x i ) SEQUENCE DESCRIPTION: SEQ ID NO:19:

GTAAGTTACT TGTTTCTAAG TGATAAAACA G Y GAAGAGCT    40

( 2 ) INFORMATION FOR SEQ ID NO:20:

( i ) SEQUENCE CHARACTERISTICS:
 ( A ) LENGTH: 40 base pairs
 ( B ) TYPE: nucleic acid
 ( C ) STRANDEDNESS: single
 ( D ) TOPOLOGY: linear ( i i ) MOLECULE TYPE: cDNA ( v i ) ORIGINAL SOURCE:
 ( A ) ORGANISM: Homo sapiens ( x i ) SEQUENCE DESCRIPTION: SEQ ID NO:20:

AATAAAAACA TAACTAATTA GGTTCTTGT TTTATTTAG    40

( 2 ) INFORMATION FOR SEQ ID NO:21:

( i ) SEQUENCE CHARACTERISTICS:
 ( A ) LENGTH: 40 base pairs
 ( B ) TYPE: nucleic acid
 ( C ) STRANDEDNESS: single
 ( D ) TOPOLOGY: linear ( i i ) MOLECULE TYPE: cDNA ( v i ) ORIGINAL SOURCE:
 ( A ) ORGANISM: Homo sapiens ( x i ) SEQUENCE DESCRIPTION: SEQ ID NO:21:

GTTAGTAAAT TSCCTTTTTT GTTTGTGGGT ATAAAAATAG    40

( 2 ) INFORMATION FOR SEQ ID NO:22:

( i ) SEQUENCE CHARACTERISTICS:
 ( A ) LENGTH: 40 base pairs
 ( B ) TYPE: nucleic acid
 ( C ) STRANDEDNESS: single
 ( D ) TOPOLOGY: linear ( i i ) MOLECULE TYPE: cDNA ( v i ) ORIGINAL SOURCE:
 ( A ) ORGANISM: Homo sapiens ( x i ) SEQUENCE DESCRIPTION: SEQ ID NO:22:

ACCATTTTTG CATGTACTGA TGTTAACTCC ATCTTAACAG    40

( 2 ) INFORMATION FOR SEQ ID NO:23:

( i ) SEQUENCE CHARACTERISTICS:
 ( A ) LENGTH: 40 base pairs
 ( B ) TYPE: nucleic acid
 ( C ) STRANDEDNESS: single
 ( D ) TOPOLOGY: linear ( i i ) MOLECULE TYPE: cDNA ( v i ) ORIGINAL SOURCE:
 ( A ) ORGANISM: Homo sapiens ( x i ) SEQUENCE DESCRIPTION: SEQ ID NO:23:

GTAAATAAAT TATTTTATCA TATTTTTTAA AATTATTTAA    40

( 2 ) INFORMATION FOR SEQ ID NO:24:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:24:

```
CATGATGTTA TCTGTATTTA CCTATAGTCT AAATTATACC ATCTATAATG TGCTTAATTT        60

TTAG                                                                    64
```

( 2 ) INFORMATION FOR SEQ ID NO:25:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:25:

```
GTAACAGAAG ATTACAAACC CTGGTCACTA ATGCCATGAC TACTTTGCTA AG               52
```

( 2 ) INFORMATION FOR SEQ ID NO:26:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:26:

```
GGATATTAAA GTCGTAATTT TGTTTCTAAA CTCATTTGGC CCACAG                      46
```

( 2 ) INFORMATION FOR SEQ ID NO:27:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:27:

```
GTATGTTCTC TATAGTGTAC ATCGTAGTGC ATGTTTCAAA                             40
```

( 2 ) INFORMATION FOR SEQ ID NO:28:

( i ) SEQUENCE CHARACTERISTICS:
        ( A ) LENGTH: 56 base pairs
        ( B ) TYPE: nucleic acid

```
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:28:

CATCATTGCT  CTTCAAATAA  CAAAGCATTA  TGGTTTATGT  TGATTTTATT  TTTCAG          56

( 2 ) INFORMATION FOR SEQ ID NO:29:

( i ) SEQUENCE CHARACTERISTICS:
            ( A ) LENGTH: 43 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:29:

GTAAGACAAA  AATGTTTTTT  AATGACATAG  ACAATTACTG  GTG                         43

( 2 ) INFORMATION FOR SEQ ID NO:30:

( i ) SEQUENCE CHARACTERISTICS:
            ( A ) LENGTH: 40 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:30:

TTAGATGATT  GTCTTTTCC  TCTTGCCCTT  TTTAAATTAG                               40

( 2 ) INFORMATION FOR SEQ ID NO:31:

( i ) SEQUENCE CHARACTERISTICS:
            ( A ) LENGTH: 44 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:31:

GTATGTTTTT  ATAACATGTA  TTTCTTAAGA  TAGCTCAGGT  ATGA                       44

( 2 ) INFORMATION FOR SEQ ID NO:32:

( i ) SEQUENCE CHARACTERISTICS:
            ( A ) LENGTH: 54 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens
```

( x i ) SEQUENCE DESCRIPTION: SEQ ID NO:32:

GCTTGGCTTC AAGTTGNCTT TTTAATGATC CTCTATTCTG TATTTAATTT ACAG    54

( 2 ) INFORMATION FOR SEQ ID NO:33:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:33:

GTACTATTTA GAATTCACC TGTTTTTCTT TTTTCTCTTT TTCTTTGAGG CAGGGTCTCA    60

CTCTG    65

( 2 ) INFORMATION FOR SEQ ID NO:34:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:34:

GCAACTAGTA TGATTTATG TATAAATTAA TCTAAAATTG ATTAATTTCC AG    52

( 2 ) INFORMATION FOR SEQ ID NO:35:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:35:

GTACCTTTGA AAACATTTAG TACTATAATA TGAATTTCAT GT    42

( 2 ) INFORMATION FOR SEQ ID NO:36:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:36:

CCAACTCNAA TTAGATGACC CATATTCAGA AACTTACTAG    40

( 2 ) INFORMATION FOR SEQ ID NO:37:

( i ) SEQUENCE CHARACTERISTICS:
   ( A ) LENGTH: 54 base pairs
   ( B ) TYPE: nucleic acid
   ( C ) STRANDEDNESS: single
   ( D ) TOPOLOGY: linear ( i i ) MOLECULE TYPE: cDNA ( v i ) ORIGINAL SOURCE:
   ( A ) ORGANISM: Homo sapiens ( x i ) SEQUENCE DESCRIPTION: SEQ ID NO:37:

GTATATATAG AGTTTTATAT TACTTTTAAA GTACAGAATT CATACTCTCA AAAA     54

( 2 ) INFORMATION FOR SEQ ID NO:38:

( i ) SEQUENCE CHARACTERISTICS:
      ( A ) LENGTH: 41 base pairs
      ( B ) TYPE: nucleic acid
      ( C ) STRANDEDNESS: single
      ( D ) TOPOLOGY: linear ( i i ) MOLECULE TYPE: cDNA ( v i ) ORIGINAL SOURCE:
      ( A ) ORGANISM: Homo sapiens ( x i ) SEQUENCE DESCRIPTION: SEQ ID NO:38:

ATTGTGACCT TAATTTGTG ATCTCTTGAT TTTTATTTCA G     41

( 2 ) INFORMATION FOR SEQ ID NO:39:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: cDNA ( v i ) ORIGINAL SOURCE:
      ( A ) ORGANISM: Homo sapiens ( x i ) SEQUENCE DESCRIPTION: SEQ ID NO:39:

TCCCCGCCTG CCGCTCTC     18

( 2 ) INFORMATION FOR SEQ ID NO:40:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: cDNA ( v i ) ORIGINAL SOURCE:
      ( A ) ORGANISM: Homo sapiens ( x i ) SEQUENCE DESCRIPTION: SEQ ID NO:40:

GCAGCGGCGG CTCCCGTG     18

( 2 ) INFORMATION FOR SEQ ID NO:41:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:41:

GTGAACGGCT CTCATGCTGC  20

( 2 ) INFORMATION FOR SEQ ID NO:42:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:42:

ACGTGCGGGG AGGAATGGA  19

( 2 ) INFORMATION FOR SEQ ID NO:43:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:43:

ATGATATCTT ACCAAATGAT ATAC  24

( 2 ) INFORMATION FOR SEQ ID NO:44:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:44:

TTATTCCTAC TTCTTCTATA CAG  23

( 2 ) INFORMATION FOR SEQ ID NO:45:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:45:

TACCCATGCT GGCTCTTTTT C  21

( 2 ) INFORMATION FOR SEQ ID NO:46:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:46:

TGGGGCCATC TTGTTCCTGA                                      20

( 2 ) INFORMATION FOR SEQ ID NO:47:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:47:

ACATTAGGCA CAAAGCTTGC AA                                  22

( 2 ) INFORMATION FOR SEQ ID NO:48:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:48:

ATCAAGCTCC AGTAAGAAGG TA                                  22

( 2 ) INFORMATION FOR SEQ ID NO:49:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:49:

TGCGGCTCCT GGGTTGTTG                                        19

( 2 ) INFORMATION FOR SEQ ID NO:50:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
    ( A ) ORGANISM: Homo sapiens ( x i ) SEQUENCE DESCRIPTION: SEQ ID NO:50:

GCCCCTTCCT TTCTGAGGAC 20

( 2 ) INFORMATION FOR SEQ ID NO:51:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:51:

TTTTCTCCTG CCTCTTACTG C 21

( 2 ) INFORMATION FOR SEQ ID NO:52:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:52:

ATGACACCCC CCATTCCCTC 20

( 2 ) INFORMATION FOR SEQ ID NO:53:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:53:

CCACTTAAAG CACATATATT TAGT 24

( 2 ) INFORMATION FOR SEQ ID NO:54:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:54:

GTATGGAAAA TAGTGAAGAA CC 22

(2) INFORMATION FOR SEQ ID NO:55:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:55:

TTCTTAAGTC CTGTTTTTCT TTTG 24

(2) INFORMATION FOR SEQ ID NO:56:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:56:

TTTAGAACCT TTTTGTGTT GTG 23

(2) INFORMATION FOR SEQ ID NO:57:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:57:

CTCAGATTAT ACACTAAGCC TAAC 24

(2) INFORMATION FOR SEQ ID NO:58:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:58:

CATGTCTCTT ACAGTAGTAC CA 22

(2) INFORMATION FOR SEQ ID NO:59:

(i) SEQUENCE CHARACTERISTICS:
        (A) LENGTH: 20 base pairs
        (B) TYPE: nucleic acid ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:59:

AGGTCCAAGG GTAGCCAAGG                                                                              20

( 2 ) INFORMATION FOR SEQ ID NO:60:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:60:

TAAAAATGGA TAAACTACAA TTAAAAG                                                                      27

( 2 ) INFORMATION FOR SEQ ID NO:61:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:61:

AAATACAGAA TCATGTCTTG AAGT                                                                         24

( 2 ) INFORMATION FOR SEQ ID NO:62:

( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:62:

ACACCTAAAG ATGACAATTT GAG                                                                          23

( 2 ) INFORMATION FOR SEQ ID NO:63:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:63:

TAACTTAGAT AGCAGTAATT TCCC    24

( 2 ) INFORMATION FOR SEQ ID NO:64:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:64:

ACAATAAACT GGAGTACACA AGG    23

( 2 ) INFORMATION FOR SEQ ID NO:65:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:65:

ATAGGTCATT GCTTCTTGCT GAT    23

( 2 ) INFORMATION FOR SEQ ID NO:66:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:66:

TGAATTTTAA TGGATTACCT AGGT    24

( 2 ) INFORMATION FOR SEQ ID NO:67:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:67:

CTTTTTTTGC TTTTACTGAT TAACG    25

( 2 ) INFORMATION FOR SEQ ID NO:68:

( i ) SEQUENCE CHARACTERISTICS:

( A ) LENGTH: 27 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapiens ( x i ) SEQUENCE DESCRIPTION: SEQ ID NO:68:

TGTAATTCAT TTTATTCCTA ATAGCTC  27

( 2 ) INFORMATION FOR SEQ ID NO:69:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapiens ( x i ) SEQUENCE DESCRIPTION: SEQ ID NO:69:

GGTAGCCATA GTATGATTAT TTCT  24

( 2 ) INFORMATION FOR SEQ ID NO:70:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapiens ( x i ) SEQUENCE DESCRIPTION: SEQ ID NO:70:

CTACCTATTT TTATACCCAC AAAC  24

( 2 ) INFORMATION FOR SEQ ID NO:71:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:
( A ) ORGANISM: Homo sapiens ( x i ) SEQUENCE DESCRIPTION: SEQ ID NO:71:

AAGAAAGCCT ACACCATTTT TGC  23

( 2 ) INFORMATION FOR SEQ ID NO:72:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( v i ) ORIGINAL SOURCE:

( A ) ORGANISM: Homo sapiens ( x i ) SEQUENCE DESCRIPTION: SEQ ID NO:72:

GATCATTCTT AGAACCATCT TGC    23

( 2 ) INFORMATION FOR SEQ ID NO:73:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:73:

ACCTATAGTC TAAATTATAC CATC    24

( 2 ) INFORMATION FOR SEQ ID NO:74:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:74:

GTCATGGCAT TAGTGACCAG    20

( 2 ) INFORMATION FOR SEQ ID NO:75:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:75:

AGTCGTAATT TTGTTTCTAA ACTC    24

( 2 ) INFORMATION FOR SEQ ID NO:76:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: cDNA ( v i ) ORIGINAL SOURCE:
            ( A ) ORGANISM: Homo sapiens ( x i ) SEQUENCE DESCRIPTION: SEQ ID NO:76:

TGAAGGACTC GGATTTCACG C    21

( 2 ) INFORMATION FOR SEQ ID NO:77:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:77:

TCATTCACTC ACAGCCTGAT GAC 23

(2) INFORMATION FOR SEQ ID NO:78:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:78:

GCTTTGAAAC ATGCACTACG AT 22

(2) INFORMATION FOR SEQ ID NO:79:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:79:

AAACATCATT GCTCTTCAAA TAAC 24

(2) INFORMATION FOR SEQ ID NO:80:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:80:

TACCATGATT TAAAAATCCA CCAG 24

(2) INFORMATION FOR SEQ ID NO:81:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: cDNA ( v i ) ORIGINAL SOURCE:
    ( A ) ORGANISM: Homo sapiens ( x i ) SEQUENCE DESCRIPTION: SEQ ID NO:81:

GATGATTGTC TTTTCCTCT TGC                                                    23

( 2 ) INFORMATION FOR SEQ ID NO:82:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:82:

CTGAGCTATC TTAAGAAATA CATG                                                  24

( 2 ) INFORMATION FOR SEQ ID NO:83:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:83:

TTTTAAATGA TCCTCTATTC TGTAT                                                 25

( 2 ) INFORMATION FOR SEQ ID NO:84:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:84:

ACAGAGTCAG ACCCTGCCTC AAAG                                                  24

( 2 ) INFORMATION FOR SEQ ID NO:85:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:85:

TTTCTATTCT TACTGCTAGC ATT                                                   23

( 2 ) INFORMATION FOR SEQ ID NO:86:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:86:

ATACACAGGT AAGAAATTAG GA                              22

( 2 ) INFORMATION FOR SEQ ID NO:87:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:87:

TAGATGACCC ATATTCTGTT TC                              22

( 2 ) INFORMATION FOR SEQ ID NO:88:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:88:

CAATTAGGTC TTTTTGAGAG TA                              22

( 2 ) INFORMATION FOR SEQ ID NO:89:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:89:

GTTACTGCAT ACACATTGTG AC                              22

( 2 ) INFORMATION FOR SEQ ID NO:90:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear (ii) MOLECULE TYPE: cDNA (vi) ORIGINAL SOURCE:
    (A) ORGANISM: Homo sapiens (xi) SEQUENCE DESCRIPTION: SEQ ID NO:90:

GCTTTTTGTT TCCTAACATG AAG                                    23

(2) INFORMATION FOR SEQ ID NO:91:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:91:

TCTCCCACAG GTAATACTCC C                                      21

(2) INFORMATION FOR SEQ ID NO:92:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:92:

GCTAGAACTG AATGGGGTAC G                                      21

(2) INFORMATION FOR SEQ ID NO:93:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:93:

CAGGACAAAA TAATCCTGTC CC                                     22

(2) INFORMATION FOR SEQ ID NO:94:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:94:

ATTTTCTTAG TTTCATTCTT CCTC         24

( 2 ) INFORMATION FOR SEQ ID NO:95:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:95:

AGAAGGATCC CTTGTGCAGT GTGGA         25

( 2 ) INFORMATION FOR SEQ ID NO:96:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:96:

GACAGGATCC TGAAGCTGAG TTTG         24

( 2 ) INFORMATION FOR SEQ ID NO:97:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:97:

TCAGAAAGTG CTGAAGAG         18

( 2 ) INFORMATION FOR SEQ ID NO:98:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Homo sapiens ( x i ) SEQUENCE DESCRIPTION: SEQ ID NO:98:

GGAATAATTA GGTCTCCAA         19

( 2 ) INFORMATION FOR SEQ ID NO:99:

( i ) SEQUENCE CHARACTERISTICS:
        ( A ) LENGTH: 21 base pairs
        ( B ) TYPE: nucleic acid (C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:99:

GCAAATCCTA AGAGAGAACA A 21

(2) INFORMATION FOR SEQ ID NO:100:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:100:

GATGGCAAGC TTGAGCCAG 19

(2) INFORMATION FOR SEQ ID NO:101:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:101:

GTTCCAGCAG TGTCACAG 18

(2) INFORMATION FOR SEQ ID NO:102:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Homo sapiens (xi) SEQUENCE DESCRIPTION: SEQ ID NO:102:

GGGAGATTTC GCTCCTGA 18

We claim:

1. A method of diagnosing or prognosing an APC-gene associated neoplastic tissue of a human, comprising:

comparing (1) APC gene coding sequences or APC mRNA in a tumor tissue isolated from a human, to (2) APC gene coding sequences or APC mRNA in a non-neoplastic tissue of the human; a difference in the APC gene coding sequences or APC mRNA between the two tissues indicating an APC-gene associated neoplasia of the tumor tissue.

2. The method of claim 1 wherein mRNA are compared molecules.

3. The method of claim 2 wherein the difference in wild-type APC mRNA is detected by hybridization of mRNA from said tissue to an APC gene probe.

4. The method of claim 1 wherein the difference in wild-type APC gene coding sequences is detected by observing differences in electrophoretic mobility on non-denaturing polyacrylamide gels, between single-stranded DNA isolated from said tumor tissue and single-stranded DNA isolated from a non-neoplastic tissue, wherein a difference in electrophoretic mobility is indicative of neoplasia or a predisposition therefor.

5. The method of claim 1 wherein the difference in APC gene coding sequences is detected by hybridization of an APC gene coding sequence probe to genomic DNA isolated from said tissue.

6. The method of claim 5 further comprising:
subjecting genomic DNA isolated from a non-neoplastic tissue of the human to Southern hybridization with the APC gene coding sequence probe; and
comparing hybridization patterns of the APC gene probe to said tumor and non-neoplastic tissues, wherein a difference in the hybridization patterns is indicative of neoplasia.

7. The method of claim 5 wherein the APC gene probe detects a restriction fragment length polymorphism.

8. The method of claim 5 wherein the APC gene probe hybridizes to an exon selected from the group consisting of: (1) nucleotides 822 to 930; (2) nucleotides 931 to 1309; (3) nucleotides 1406 to 1545; and (4) nucleotides 1956 to 2256, as shown in SEQ ID NO: 1.

9. The method of claim 6 wherein the non-neoplastic tissue isolated from a human is from colonic mucosa.

10. The method of claim 1 wherein the difference in APC gene coding sequences is detected by determining the sequence of all or part of an APC gene in said tissue using a polymerase chain reaction.

11. The method of claim 1 wherein the difference in APC gene coding sequences is detected by identifying a mismatch between (1) an APC gene or APC mRNA isolated from said tissue and (2) a nucleic acid probe complementary to the human wild-type APC gene coding sequence, when molecules (1) and (2) are hybridized to each other to form a duplex.

12. The method of claim 1 wherein the difference in APC gene coding sequences is detected by amplification of APC gene sequences in said tissue and hybridization of the amplified APC sequences to nucleic acid probes which comprise APC sequences.

13. The method of claim 1 wherein the difference in APC gene coding sequences is detected by molecular cloning of the APC genes in said tissue and sequencing all or part of the cloned APC gene.

14. The method of claim 1 wherein the APC gene coding sequences are screened for a deletion mutation.

15. The method of claim 1 wherein the APC gene coding sequences are screened for a point mutation.

16. The method of claim 1 wherein the APC gene coding sequences are screened for an insertion mutation.

17. The method of claim 1 wherein the tumor tissue is a colorectal tissue.

18. The method of claim 1 wherein the APC gene coding sequences are screened for a mutation which creates a stop codon.

19. A method of detecting the presence of a neoplastic tissue in a human, comprising:
comparing (1) APC gene coding sequences or APC mRNA in a body sample isolated from a human to (2) wild-type APC gene coding sequences or wild-type APC mRNA, a difference in the APC gene coding sequences or APC mRNA between the body sample and wild-type indicating the presence of a neoplastic tissue in the human.

20. The method of claim 19 wherein said body sample is selected from the group consisting of serum, stool, urine and sputum.

21. A method of detecting genetic predisposition to cancer, in a human comprising:
comparing (1) wild-type APC gene coding sequences or wild-type APC mRNA to (2) APC gene coding sequences or APC mRNA in a human sample selected from the group consisting of blood and fetal tissue, a difference between the wild-type and the sample APC gene coding sequences or APC mRNA indicating predisposition to cancer of the human.

22. The method of claim 21 wherein mRNA molecules are compared.

23. The method of claim 22 wherein the difference in APC mRNA is detected by hybridization of mRNA from said tissue to an APC gene probe.

24. The method of claim 21 wherein difference in APC gene coding sequences is detected by observing differences in electrophoretic mobility on non-denaturing polyacrylamide gels between single-stranded DNA isolated from said sample and single-stranded DNA of said wild-type APC gene, wherein a difference in electrophoretic mobility is indicative of said predisposition.

25. The method of claim 21 wherein the difference in APC gene coding sequences is detected by hybridization of an APC gene coding sequence probe to genomic DNA isolated from said tissue.

26. The method of claim 25 wherein the APC gene coding sequence probe detects a restriction fragment length polymorphism.

27. The method of claim 25 wherein the APC gene probe hybridizes to an exon selected from the group consisting of: (1) nucleotides 822 to 930; (2) nucleotides 931 to 1309; (3) nucleotides 1406 to 1545 and (4) nucleotides 1956 to 2256, as shown in SEQ ID NO: 1.

28. The method of claim 21 wherein the difference in APC gene coding sequences is detected by determining the sequence of all or part of an APC gene in said tissue using a polymerase chain reaction, and the wild type APC sequence compared is the sequence of FIG. 7.

29. The method of claim 21 wherein the difference in APC gene coding sequences is detected by identifying a mismatch between (1) an APC gene or APC mRNA isolated from said tissue and (2) a nucleic acid probe complementary to the human wild-type APC gene coding sequence, when molecules (1) and (2) are hybridized to each other to form a duplex.

30. The method of claim 21 wherein the difference in APC gene coding sequences is detected by amplification of APC gene sequences in said tissue and hybridization of the amplified APC sequences to nucleic acid probes which comprise APC gene coding sequences.

31. The method of claim 21 wherein the difference in wild-type APC gene coding sequences is detected by molecular cloning of the APC genes in said tissue and sequencing all or part of the cloned APC gene.

32. The method of claim 21 wherein the APC gene coding sequences are screened for a deletion mutation.

33. The method of claim 21 wherein the APC gene coding sequences are screened for a point mutation.

34. The method of claim 21 wherein the APC gene coding sequences are screened for an insertion mutation.

35. The method of claim 21 wherein the APC gene coding sequences are screened for a mutation which creates a stop codon.

36. A method of screening for genetic predisposition to cancer, in a human comprising:
detecting among kindred persons the presence of a DNA polymorphism which is linked to a mutant APC allele in an individual having said genetic predisposition, said kindred being genetically related to the individual, the presence of said polymorphism suggesting said predisposition.

* * * * *